US012715935B2

(12) United States Patent
Dessain et al.

(10) Patent No.: US 12,715,935 B2
(45) **Date of Patent: *Aug. 25, 2026**

(54) METHODS AND COMPOSITIONS FOR INDUCIBLE EXTRACELLULAR MEMBRANE CAPTURE OF MONOCLONAL IMMUNOGLOBULINS SECRETED BY HYBRIDOMAS

(71) Applicant: Lankenau Institute for Medical Research, Wynnewood, PA (US)

(72) Inventors: Scott K. Dessain, Wynnewood, PA (US); Rama Devudu Puligedda, Secane, PA (US)

(73) Assignee: Lankenau Institute for Medical Research, Wynnewood, PA (US)

( * ) Notice: Subject to any disclaimer, the term of this patent is extended or adjusted under 35 U.S.C. 154(b) by 199 days.

This patent is subject to a terminal disclaimer.

(21) Appl. No.: 18/443,701

(22) Filed: Feb. 16, 2024

(65) Prior Publication Data

US 2024/0191207 A1 Jun. 13, 2024

Related U.S. Application Data

(63) Continuation of application No. 16/495,552, filed as application No. PCT/US2018/024073 on Mar. 23, 2018, now Pat. No. 11,946,074.

(60) Provisional application No. 62/526,608, filed on Jun. 29, 2017, provisional application No. 62/476,599, filed on Mar. 24, 2017.

(51) Int. Cl.

| | |
|---|---|
| ***C07K 16/42*** | (2006.01) |
| ***C07K 16/10*** | (2026.01) |
| ***C12N 5/16*** | (2006.01) |
| ***C12N 15/10*** | (2006.01) |
| ***G01N 33/569*** | (2006.01) |

(52) U.S. Cl.

CPC .......... *C07K 16/4283* (2013.01); *C07K 16/10* (2013.01); *C12N 5/163* (2013.01); *C12N 15/1034* (2013.01); *G01N 33/56966* (2013.01); *C07K 2317/14* (2013.01); *C07K 2317/21* (2013.01)

(58) Field of Classification Search

None

See application file for complete search history.

(56) References Cited

U.S. PATENT DOCUMENTS

| | | | |
|---|---|---|---|
| 6,919,183 B2 | 7/2005 | Fandl et al. | |
| 7,435,553 B2 | 10/2008 | Fandl et al. | |
| 7,906,111 B2 | 3/2011 | Wilson et al. | |
| 8,557,575 B2 | 10/2013 | Dessain et al. | |
| 8,663,985 B2 | 3/2014 | Miltneyi et al. | |
| 8,912,385 B2 | 12/2014 | Meagher | |
| 9,389,236 B2 | 7/2016 | Fandl et al. | |
| 11,946,074 B2 * | 4/2024 | Dessain | C12N 5/163 |
| 2002/0168629 A1 | 11/2002 | Burton et al. | |
| 2011/0269152 A1 | 11/2011 | Miltneyi et al. | |
| 2016/0033530 A1 | 2/2016 | Fandl et al. | |
| 2016/0258952 A1 | 9/2016 | Lai | |

FOREIGN PATENT DOCUMENTS

| | | |
|---|---|---|
| EP | 2304029 | 4/2011 |
| WO | WO 2000/042176 | 7/2000 |
| WO | WO 2002/057423 | 7/2002 |
| WO | WO 2002/057423 A2 | 7/2002 |
| WO | WO 2010/069913 | 6/2010 |
| WO | WO 2011/100566 | 8/2011 |
| WO | WO 2014/078475 A2 | 5/2014 |

OTHER PUBLICATIONS

Kim et al. 'CHO cells in biotechnology for production of recombinant proteins: current state and further potential.' Appl Microbiol Biotechnol (2012) 93:917-930.*

Rakestraw, J.A. et al. Secretion-and-capture cell-surface display for selection of target-binding proteins. Protein Eng Des Sel. Jun. 2011;24(6):525-30. Epub Mar. 14, 2011.

Akamatsu, Y. et al. Whole IgG surface display on mammalian cells: application to isolation of neutralizing chicken monoclonal anti-IL-12 antibodies. J Immunol Methods. Oct. 31, 2007;327(1-2):40-52. Epub Aug. 2, 2007.

Carroll, S. et al. ACSD labelling and magnetic cell separation: a rapid method of separating antibody secreting cells from non-secreting cells. J Immunol Methods. Jan. 2005;296(1-2):171-8. Epub Dec. 8, 2004.

Kenney, J.S., et al. Production of Monoclonal Antibodies Using a Secretion Capture Report Web. Biotechnology (N Y). Aug. 1995; 13(8):787-90.

Rhiel, L. et al. REAL-Select: Full-length Antibody Display and Library Screening by Surface Capture on Yeast Cells. PLoS One. Dec. 12, 2014;9(12):e114887. eCollection 2014.

anz, R. et al. Analysis and sorting of live cells according to secreted molecules relocated to a cell-surface affinity matrix. Proc Natl Acad Sci U S A. Mar. 14, 1995;92(6):1921-5.

Kida, A. et al. Cell Surface-Fluorescence Immunosorbent Assay for Real-Time Detection of Hybridomas with Efficient Antibody Secretion at the Single-Cell Level. Anal Chem. Feb. 5, 2013;85(3):1753-9. Epub Jan. 18, 2013.

Li, X. et al. A Rapid Method for Antigen-Specific Hybridoma clone Isolation. Anal Chem. Feb. 6, 2018;90(3):2224-2229. Epub Jan. 17, 2018.

Chen, Z. et al. Cross-neutralizing human anti-poliovirus antibodies bind the recognition site for cellular receptor. Proc Natl Acad Sci U S A. Dec. 10, 2013;110(50):20242-7. doi: 10.1073/pnas.1320041110. Epub Nov. 25, 2013.

(Continued)

*Primary Examiner* — Nora M Rooney

(74) *Attorney, Agent, or Firm* — Howson & Howson LLP; Colleen M. Schaller

(57) ABSTRACT

Compositions and methods are provided for making and using a cell having expressed on its outer plasma membrane surface an Anchor designed to form a first complex with a selected Linker. The Linker is designed to form a second complex with a target protein that is not recognized by the Anchor. These cells can be primary cells or immortalized cells, and can function as fusion partners to create hybridoma cells.

18 Claims, 19 Drawing Sheets

Specification includes a Sequence Listing.

(56) References Cited

OTHER PUBLICATIONS

Sommer, J. Constitutively Active Mutant gp130 Receptor Protein from Inflammatory Hepatocellular Adenoma is Inhibited by an Anti-gp130 Antibody That Specifically Neutralizes Interleukin 11 Signaling. J Biol Chem. Apr. 20, 2012;287(17):13743-51.
Puligedda, R. et al. Capture and display of antibodies secreted by hybridoma cells enables fluorescent on-cell screening11, MABS, vol. 11, No. 3, Feb. 22, 2019 (Feb. 22, 2019), pp. 546-558, XP055752162.
Zhou, C et al. Development of a novel mammalian cell surface antibody display platform, mAbs (Sep./Oct. 2010), 2:5, 508-518.
Mckinney, KL et al., Manipulation of Heterogeneous Hybridoma Cultures for Overproduction of Monoclonal Antibodies. Biotechnol Prog. (Sep./Oct. 1991), 7(5):445-54.
Price et al., Engineered cell surface expression of membrane immunoglobulin as a means to identify monoclonal antibody-secreting hybridomas. J Immunol Methods. Mar. 31, 2009;343(1):28-41. doi: 10.1016/j.jim.2009.01.005. Epub Jan. 31, 2009.
Kumar, N et al. Flow-cytometry and cell sorting: an efficient approach to investigate productivity and cell physiology in mammalian cell factories. Methods. Mar. 2012;56(3):366-74.
Dobson, L et al. The human transmembrane proteome. Biol Direct. May 28, 2015;10:31.
Khan, KH. Gene Expression in Mammalian Cells and its Applications. Adv Pharm Bull. 2013;3(2):257-63.
Manjunath, N et al. Lentiviral delivery of short hairpin RNAs. Adv Drug Deliv Rev. Jul. 25, 2009;61(9):732-45.
Mattiazzi Usaj, M et al. High-Content Screening for Quantitative Cell Biology. Trends Cell Biol. Aug. 2016;26(8):598-611.
Tiscornia, G et al. Production and purification of lentiviral vectors. Nat Protoc. 2006;1(1):241-5.
Dessain, SK et al., High efficiency creation of human monoclonal antibody-producing hybridomas. J Immunol Methods. Aug. 2004;291(1-2):109-22.
Vitale, LA et al., Development of a human monoclonal antibody for potential therapy of CD27-expressing lymphoma and leukemia. Clin Cancer Res. Jul. 15, 2012;18(14):3812-21.
Walker, C et al. T cell activation by cross-linking anti-CD3 antibodies with second anti-T cell antibodies: dual antibody cross-linking mimics physical monocyte interaction. Eur J Immunol. Nov. 1987;17(11):1611-8.
Merle, NS et al. Complement System Part I—Molecular Mechanisms of Activation and Regulation. Front Immunol. Jun. 2, 2015;6:262.
Taylor, RP et al. The role of complement in mAb-based therapies of cancer. Methods. Jan. 1, 2014;65(1):18-27.
Puligedda, RD et al., Human monoclonal antibodies that neutralize vaccine and wild-type poliovirus strains. Antiviral Res. Aug. 2014;108:36-43.
Adekar, SP et al., Hybridoma populations enriched for affinity-matured human IgGs yield high-affinity antibodies specific for botulinum neurotoxins. J Immunol Methods. Apr. 20, 2008;333(1-2):156-66.
Yu, X et al. An optimized electrofusion-based protocol for generating virus-specific human monoclonal antibodies. Immunol Methods. Jul. 31, 2008;336(2):142-51.
Mompo, SM et al., Antigen-specific human monoclonal antibodies from transgenic mice. Methods Mol Biol. 2014;1060:245-76.
Spieker-Polet, H et al. Rabbit monoclonal antibodies: generating a fusion partner to produce rabbit-rabbit hybridomas. Proc Natl Acad Sci U S A. Sep. 26, 1995;92(20):9348-52.
Hoehn, KB et al. The Diversity and Molecular Evolution of B-Cell Receptors during Infection. Mol Biol Evol. May 2016;33(5):1147-57.
Ravetch, JV et al. IgG Fc receptors. Annu Rev Immunol (2001) 19:275-290.
Chattopadhyay, PK et al. Live-cell assay to detect antigen-specific CD4+ T-cell responses by CD154 expression. Nat Protoc. 2006;1(1):1-6.
Kohler, G and Milstein C. Continuous cultures of fused cells secreting antibody of predefined specificity. Nature. Aug. 7, 1975;256(5517):495-7.
Zhu, Y, et al. Improved fusion partners transfected with DNA fragment encoding IL-11 on generation of human B lymphocyte hybridomas. Hum Antibodies. 1999;9(1):1-7.
Feldhaus, MJ et al. Flow-cytometric isolation of human antibodies from a nonimmune *Saccharomyces cerevisiae* surface display library. Nat Biotechnol. Feb. 2003;21(2):163-70.
Harris, JF et al. Increased frequency of both total and specific monoclonal antibody producing hybridomas using a fusion partner that constitutively expresses recombinant IL-6. J Immunol Methods. Apr. 8, 1992;148(1-2):199-207.
Flyak AI, et al. Mechanism of human antibody-mediated neutralization of Marburg virus. Cell. Feb. 26, 2015;160(5):893-903.
Jin, Y et al. Human monoclonal antibodies as candidate therapeutics against emerging viruses. Front Med. Dec. 2017;11(4):462-470.
Dessain, SK et al. Exploring the native human antibody repertoire to create antiviral therapeutics. Curr Top Microbiol Immunol. 2008;317:155-83.
Tiller, T et al. Efficient generation of monoclonal antibodies from single human B cells by single cell RT-PCR and expression vector cloning. J Immunol Methods. Jan. 1, 2008;329(1-2):112-24.
Smith, SA, Crowe JE, Jr. Use of Human Hybridoma Technology to Isolate Human Monoclonal Antibodies. Microbiology spectrum. Microbiol Spectr. Feb. 2015;3(1):AID-0027-2014.
Bowers, PM, et al. Mammalian cell display for the discovery and optimization of antibody therapeutics. Methods. Jan. 1, 2014;65(1):44-56.
Pavri, R, Nussenzweig MC. AID targeting in antibody diversity. Adv Immunol. 2011;110:1-26.
Romanti, B, et al. Antibody production by in vivo RNA transfection. Sci Rep. Sep. 7, 2017;7(1):10863.
Lorenz, CM, et al. The effect of low intensity ultraviolet-C light on monoclonal antibodies. Biotechnol Prog. Mar.-Apr. 2009;25(2):476-82.
Gaborit, N, et al. Time-resolved fluorescence resonance energy transfer (TRFRET) to analyze the disruption of EGFR/HER2 dimers: a new method to evaluate the efficiency of targeted therapy using monoclonal antibodies. J Biol Chem. Apr. 1, 2011;286(13):11337-45.
Lee, SS, et al. Development of a micro-neutralization assay for ebolaviruses using a replication-competent vesicular stomatitis hybrid virus and a quantitative PCR readout. Vaccine. Oct. 4, 2017;35(41):5481-5486.
Mcfadden, G, et al. Cytokine determinants of viral tropism. Nat Rev Immunol. Sep. 2009;9(9):645-55.
Mendelsohn, CL, et al. Cellular receptor for poliovirus: molecular cloning, nucleotide sequence, and expression of a new member of the immunoglobulin superfamily. Cell. Mar. 10, 1989;56(5):855-65.
Puligedda, RD, et al. Characterization of human monoclonal antibodies that neutralize multiple poliovirus serotypes. Vaccine. Oct. 4, 2017;35(41):5455-5462.
Doi, T, et al. The C-terminal region of activation-induced cytidine deaminase is responsible for a recombination function other than DNA cleavage in class switch recombination. Proc Natl Acad Sci U S A. Feb. 24, 2009; 106(8):2758-63.
Yousefzadeh, MJ et al. Mechanism of suppression of chromosomal instability by DNA polymerase POLQ. PLoS Genet. Oct. 2, 2014;10(10):e1004654.
Spencer, S et al. Solubility evaluation of murine hybridoma antibodies. MAbs. May-Jun. 2012;4(3):319-25.
Rossant, C.J. et al. Phage display and hybridoma generation of antibodies to human CXCR2 yields antibodies with distinct mechanisms and epitopes. MAbs. Nov.-Dec. 2014;6(6):1425-38.
Layton, D et al. Design and operation of an automated high-throughput monoclonal antibody facility. Biophys Rev. Mar. 2013;5(1):47-55.
Yokoyama, W.M., et al. (2013), Production of Monoclonal Antibodies. Current Protocols in Immunology, 102: 2.5.1-2.5.29.
Weaver, J.C. et al. Gel microdrop technology for rapid isolation of rare and high producer cells. Nat Med. May 1997;3(5):583-5.

(56) References Cited

OTHER PUBLICATIONS

El Debs, B., Utharala, R., Balyasnikova, I. V., Griffiths, A.D. & Merten, C.A. Functional single-cell hybridoma screening using droplet-based microfluidics. Proc Natl Acad Sci U S A. Jul. 17, 2012;109(29):11570-5.

Shen, Z. et al. Engineered recombinant single-chain fragment variable antibody for immunosensors. Anal Chem. Nov. 1, 2005;77(21):6834-42.

Ho, M. & Pastan, I. Display and selection of scFv antibodies on HEK-293T cells. Methods Mol Biol. 2009;562:99-113.

Foltz, I.N., et al. Discovery and bio-optimization of human antibody therapeutics using the XenoMouse® transgenic mouse platform. Immunol Rev. Mar. 2016;270(1):51-64.

Kreye, J. et al. Human cerebrospinal fluid monoclonal N-methyl-D-aspartate receptor autoantibodies are sufficient for encephalitis pathogenesis. Brain. Oct. 2016;139(Pt 10):2641-2652.

Dalmau, J. et al. Anti-NMDA-receptor encephalitis: case series and analysis of the effects of antibodies. Lancet Neurol. Dec. 2008; 7(12):1091-8.

Gleichman, A.J., et al. Anti-NMDA receptor encephalitis antibody binding is dependent on amino acid identity of a small region within the GluN1 amino terminal domain. J Neurosci. Aug. 8, 2012;32(32):11082-94.

Sharma, R. et al. Membrane-bound and soluble forms of an NMDA receptor extracellular domain retain epitopes targeted in auto-immune encephalitis. BMC Biotechnol. Jun. 27, 2018;18(1):41.

Sharma, R. et al. Monoclonal antibodies from a patient with anti-NMDA receptor encephalitis. Ann Clin Transl Neurol. Jul. 5, 2018;5(8):935-951.

Chao, G. et al. Isolating and engineering human antibodies using yeast surface display. Nat Protoc. 2006;1(2):755-68.

Wang, B. et al. Functional interrogation and mining of natively paired human VH:VL antibody repertoires. Nat Biotechnol. Feb. 2018;36(2):152-155.

Wrammert, J et al. Rapid cloning of high-affinity human monoclonal antibodies against influenza virus. Nature. May 29, 2008;453(7195):667-71.

Liao, HX et al. High-throughput isolation of immunoglobulin genes from single human B cells and expression as monoclonal antibodies. J Virol Methods. Jun. 2009;158(1-2):171-9.

Berman, HM et al. The protein data bank. Nucleic Acids Res. Jan. 1, 2000;28(1):235-42.

Malviya, M et al. NMDAR encephalitis: passive transfer from man to mouse by a recombinant antibody. Ann Clin Transl Neurol. Oct. 3, 2017;4(11):768-783.

Adekar, SP et al. A human monoclonal antibody that binds serotype A botulinum neurotoxin. Hybridoma (Larchmt). Feb. 2008;27(1):11-7.

Tillotson, BJ et al. Engineering an anti-transferrin receptor ScFv for pH-sensitive binding leads to increased intracellular accumulation. PLoS One. Dec. 29, 2015;10(12):e0145820.

Puri, V et al., Highly efficient selection of epitope specific antibody through competitive yeast display library sorting. MAbs. Jul.-Aug. 2013;5(4):533-9.

Priola, JJ et al. High-throughput screening and selection of mammalian cells for enhanced protein production. Biotechnol J. Jul. 2016;11(7):853-65.

Carroll, S. et al. Mouse x human heterohybridomas as fusion partners with human B cell tumors. J Immunol Methods. May 1, 1986;89(1):61-72.

Naviaux, RK et al. The pCL vector system: rapid production of helper-free, high-titer, recombinant retroviruses. J Virol. Aug. 1996;70(8):5701-5.

Machida, K et al. Hepatitis C virus induces a mutator phenotype: enhanced mutations of immunoglobulin and protooncogenes. Proc Natl Acad Sci U S A. Mar. 23, 2004;101(12):4262-7.

Saphire, EO et al. Crystal structure of a neutralizing human IGG against HIV-1: a template for vaccine design. Science. Aug. 10, 2001;293(5532):1155-9.

Freitag, S. Structural studies of the streptavidin binding loop. Protein Sci. Jun. 1997;6(6):1157-66.

Filman, DJ et al. Structural factors that control conformational transitions and serotype specificity in type 3 poliovirus. EMBO J. May 1989;8(5):1567-79.

Pulligedda et al., Human IgA Monoclonal Antibodies That Neutralize Poliovirus, Produced by Hybridomas and Recombinant Expression. Antibodies (Basel). Feb. 28, 2020;9(1):5.

International Search Report and Written Opinion, dated Jul. 30, 2018 in corresponding International Patent Application PCT/US2018/024073, filed Mar. 23, 2018.

European Search Report, dated Mar. 12, 2020 in corresponding European Patent Application No. 18771562.8 filed Sep. 26, 2019.

Office Action dated Feb. 2, 2022 issued in corresponding Japanese Application No. 2020-501430 (including translation provided by local agent).

Applicant's Response in European Patent Application No. 18771562.8, filed Apr. 21, 2020.

Examination Report in European Patent Application No. 18771562.8, dated Oct. 26, 2023.

Office Action dated Apr. 27, 2023 issued in Israeli Patent Application No. 269472 (including translation provided by local agent).

Applicant's Response to Office Action in Israeli Patent Application No. 269472, filed Nov. 23, 2023.

Notice of Allowance dated Dec. 18, 2023 issued in U.S. Appl. No. 16/495,552.

Office Action dated Feb. 15, 2024 issued in Canadian Patent Application No. 3056249.

Non-Final Office Action dated Apr. 20, 2023 issued in U.S. Appl. No. 16/495,552, and Response filed Jul. 19, 2023.

Non-Final Office Action dated Oct. 27, 2023 issued in U.S. Appl. No. 16/495,552, and Response filed Nov. 17, 2023.

* cited by examiner

BGS -

BGS +

APC-H

B5-6T

BGS -

BGS +

APC-H

LCX hIgG - hIgG +

FITC-H

B5-6T BGS

LCX BGS

B5-6T BGS

LCX BGS

B5-6T

LCX mAb -
mAb +
A12 mAb mAb -
mAb +
1B8 mAb

RABV
BoNT
B5-6T BGS

RABV
BoNT
LCX BGS

FIG. 9A
FIG. 9B
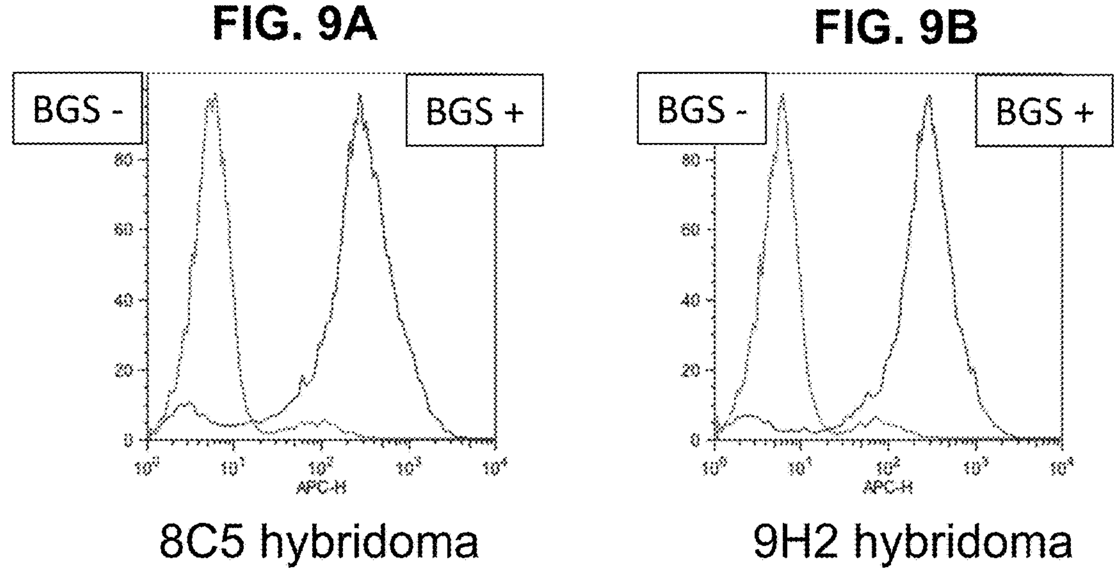
8C5 hybridoma
9H2 hybridoma
FIG. 10A
FIG. 10B
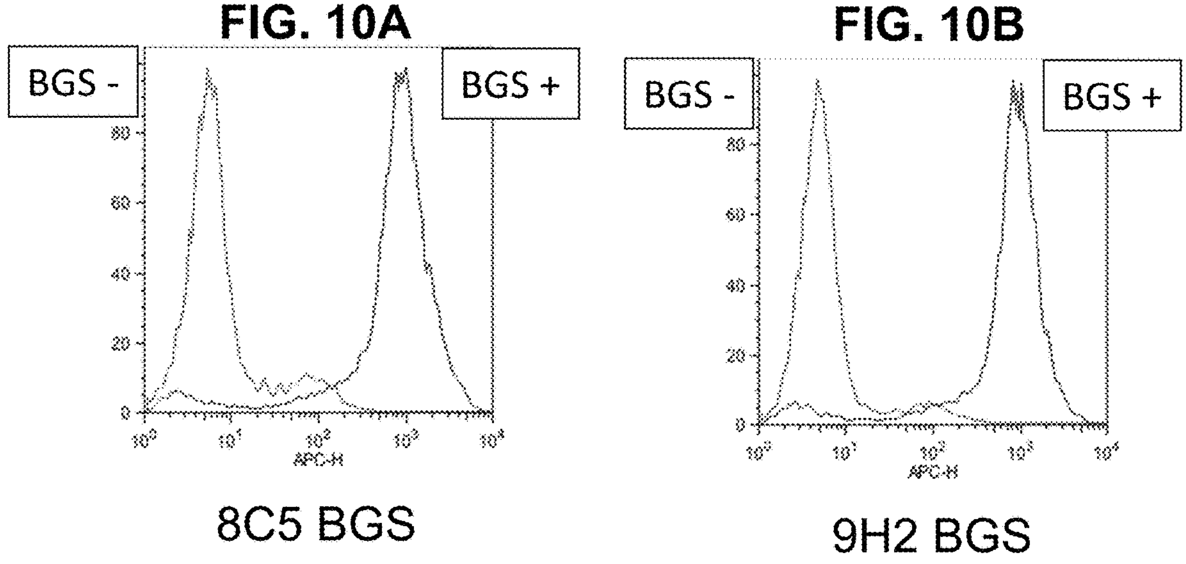
8C5 BGS
9H2 BGS

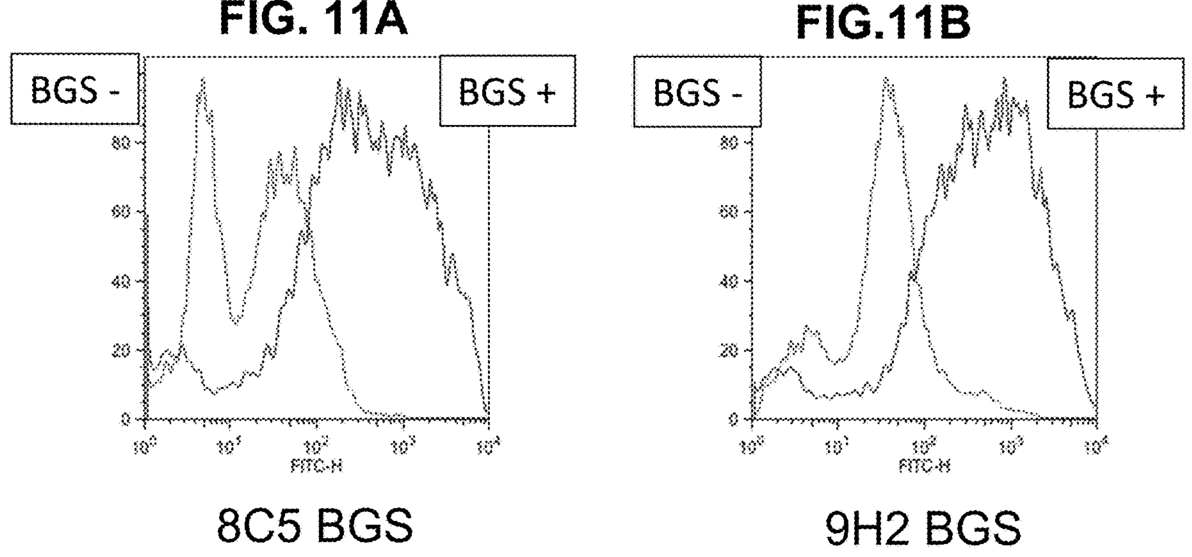
FIG. 11A
BGS -
BGS +
FITC-H
8C5 BGS
FIG.11B
BGS -
BGS +
FITC-H
9H2 BGS
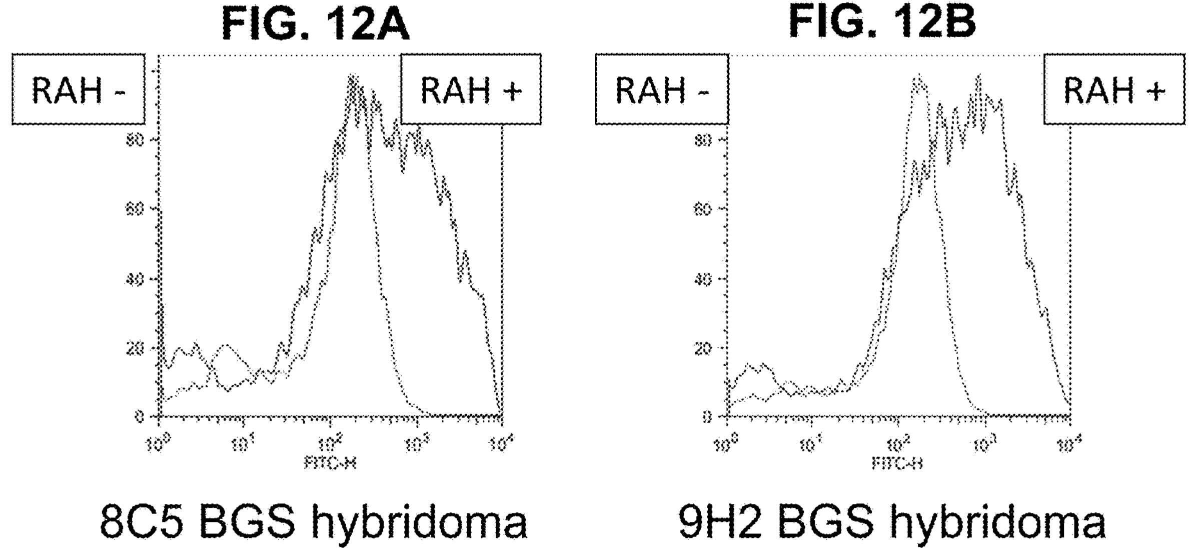
FIG. 12A
RAH -
RAH +
FITC-H
8C5 BGS hybridoma
FIG. 12B
RAH -
RAH +
FITC-H
9H2 BGS hybridoma Red: B5-6T BGS
Blue: 8C5
Green: 8C5 BGS Red: K6H6/B5
Blue: LCX Red: K6H6/B5
Blue: LCX BGS

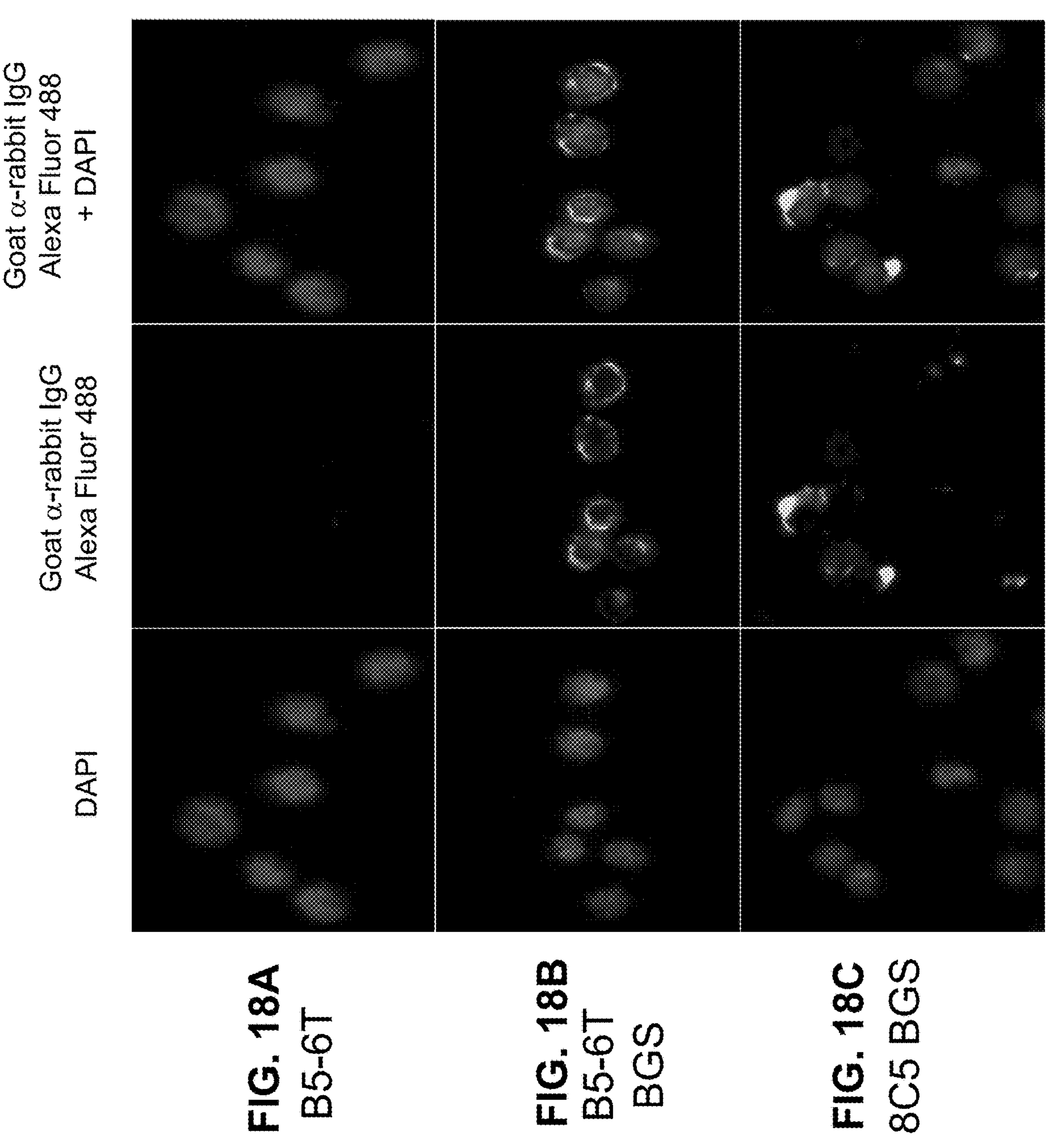
FIG. 18A B5-6T
FIG. 18B B5-6T BGS
FIG. 18C 8C5 BGS

293T OCMS With RAH

293T OCMS With Human IgG

SEQUENCE LISTING

```
Sequence total quantity: 2
SEQ ID NO: 1              moltype = DNA  length = 1781
FEATURE                   Location/Qualifiers
source                    1..1781
                          mol_type = other DNA
                          organism = synthetic construct
misc_feature              1..12
                          note = 5' restriction domain
misc_feature              13..75
                          note = leader sequence
exon                      13..1767
                          note = capture protein construct coding sequence
misc_feature              76..432
                          note = scFv heavy chain
misc_feature              433..477
                          note = spacer sequence
misc_feature              478..807
                          note = scFv light chain sequence
misc_feature              808..852
                          note = spacer sequence
misc_feature              853..1209
                          note = scFv heavy chain sequence
misc_feature              1210..1254
                          note = spacer sequence
misc_feature              1255..1584
                          note = scFv light chain sequence
misc_feature              1585..1614
                          note = c-Myc tag
misc_feature              1615..1764
                          note = PDGF receptor TM domain
misc_feature              1765..1767
                          note = stop codon
misc_feature              1768..1781
                          note = 3' restriction domain
SEQUENCE: 1
gaattcgccg ccatggaaac cgatactctc ctcctctggg tcctcctcct ctgggtgccc  60
ggctctacag gggatcaggt gcagctccag cagtctggga ccgaggtggt gaagcccggc  120
gcctctgtga agctgagctg caaggcttcc ggatacatct tcacctccta cgacatcgat  180
tgggtgcggc agacacctga gcagggcctg gagtggatcg gatggatctt cccaggcgag  240
ggatccacag agtacaacga gaagtttaag ggccgcgcca ccctgtctgt ggacaagagc  300
tcctctacag cttacatgga gctgaccagg ctgacatccg aggattctgc cgtgtacttc  360
tgcgctagag gcgactacta caggagatac tttgatctgt ggggccaggg aaccacagtg  420
accgtgagct ccggaggagg aggatctgga ggaggaggaa gcggaggagg aggatccgac  480
atcgagctga cccagtctcc cacaatcatg tctgccagcc ctggcgagag ggtgaccatg  540
acatgtagcg ccagcagcag catcagatac atctactggt accagcagaa gcccggctct  600
agccctaggc tgctgatcta cgacacctct aacgtggcca gcggagtgcc atccagattc  660
tccggctctg gaagcggcac ctcctactct ctgacaatca accggatgga ggctgaggat  720
gccgctacat actactgcca ggagtggagc ggctacccct acacctttgg cggaggcaca  780
aagctggagc tgaagcaggc cgctgccggc ggcggaggat ctggaggcgg aggcagcggc  840
ggaggaggct cccaggtgca gctgcagcag tccggaaccg aggtggtgaa gcctggagct  900
tccgtgaagc tgagctgtaa ggcttccggc tacatcttca cctcttatga tattgactgg  960
gtgcggcaga ccccagaaca gggcctggag tggattggat ggatcttccc tggagagggc  1020
tctaccgaat ataatgaaaa gtttaagggc agagccaccc tgtccgtgga caagtcctct  1080
agcaccgcct acatggagct gacccggctg acaagcgagg attccgccgt gtacttttgt  1140
gctcgcggcg actactaccg gcgctacttt gatctgtggg gacagggcac cacagtgacc  1200
gtgtcctctg gcggtggcgg ctccggcggc ggcggctctg gcggcggcgg ctctgatatc  1260
gagctgaccc agtccccaac aatcatgagc gcctccccag gagaaagagt gaccatgaca  1320
tgttctgcta gctcctctat ccgctatatc tactggtatc agcagaagcc aggcagctcc  1380
ccaagactcc tcatctacga tacatccaac gtggcttctg gagtgccttc caggttctct  1440
ggaagcggct ccggaacctc ttacagcctg acaatcaaca gaatggaggc cgaggatgct  1500
gccacatact actgtcagga gtggtccggc tacccataca cctttggagg cggaaccaaa  1560
ctggagctga agcaggctgc cgctgagcag aagctgatca gcgaggagga cctgaacgct  1620
gtgggacagg atacccagga agtgatcgtg gtgcctcact ctctgccctt caaggtggtg  1680
gtcatcagcg ccatcctggc tctggtggtc ctgaccatta tctcactcat tatcctgatt  1740
atgctgtggc agaagaaacc aaggtaactc gaggcggccg c                        1781

SEQ ID NO: 2              moltype = AA  length = 584
FEATURE                   Location/Qualifiers
source                    1..584
                          mol_type = protein
                          organism = synthetic construct
SEQUENCE: 2
METDTLLLWV LLLWVPGSTG DQVQLQQSGT EVVKPGASVK LSCKASGYIF TSYDIDWVRQ  60
```

-continued

```
TPEQGLEWIG WIFPGEGSTE YNEKFKGRAT LSVDKSSSTA YMELTRLTSE DSAVYFCARG  120
DYYRRYFDLW GQGTTVTVSS GGGGSGGGGS GGGGSDIELT QSPTIMSASP GERVTMTCSA  180
SSSIRYIYWY QQKPGSSPRL LIYDTSNVAS GVPSRFSGSG SGTSYSLTIN RMEAEDAATY  240
YCQEWSGYPY TFGGGTKLEL KQAAAGGGGS GGGGSGGGGS QVQLQQSGTE VVKPGASVKL  300
SCKASGYIFT SYDIDWVRQT PEQGLEWIGW IFPGEGSTEY NEKFKGRATL SVDKSSSTAY  360
MELTRLTSED SAVYFCARGD YYRRYFDLWG QGTTVTVSSG GGGSGGGGSG GGGSDIELTQ  420
SPTIMSASPG ERVTMTCSAS SSIRYIYWYQ QKPGSSPRLL IYDTSNVASG VPSRFSGSGS  480
GTSYSLTINR MEAEDAATYY CQEWSGYPYT FGGGTKLELK QAAAEQKLIS EEDLNAVGQD  540
TQEVIVVPHS LPFKVVVISA ILALVVLTII SLIILIMLWQ KKPR                  584
```

METHODS AND COMPOSITIONS FOR INDUCIBLE EXTRACELLULAR MEMBRANE CAPTURE OF MONOCLONAL IMMUNOGLOBULINS SECRETED BY HYBRIDOMAS

RELATED PATENT APPLICATIONS

This application is a continuation of U.S. patent application Ser. No. 16/495,552, filed Sep. 19, 2019, now U.S. Pat. No. 11,946,074, issued Apr. 2, 2024, which is a national stage of International Patent Application No. PCT/US2018/024073, filed Mar. 23, 2018, which claims the benefit of the priority of U.S. Provisional Patent Application No. 62/476,599, filed Mar. 24, 2017, and U.S. Provisional Patent Application No. 62/526,608, filed Jun. 29, 2017, which applications are incorporated herein by reference.

DEPOSITED BIOLOGICAL MATERIAL

The following cell lines were deposited under the Budapest Treaty on the International Recognition of the Deposit of Material for the Purposes of Patent Procedure on Mar. 24, 2017 with the American Type Culture Collection, 10801 University Boulevard, Manassas, Virginia, 20110, USA:

(a) Accession No. PTS-124063—Cell line LCX (LCX 03.06.17), which is a cell line which is derived from the K6H6/B5 cell line, through ectopic expression of a human telomerase catalytic subunit and a constitutively active gp130 deletion mutant cytokine receptor protein, as described herein; and (b) Accession No. PTS-124062—Fusion partner cell line LCX-BGS, which is derived from the K6H6/B5 cell line, through ectopic expression of a human telomerase catalytic subunit and a constitutively active gp130 deletion mutant cytokine receptor protein, and which expresses on its surface the tandem scoff anchor protein, BGS, as described herein.

INCORPORATION-BY-REFERENCE OF MATERIAL SUBMITTED IN ELECTRONIC FORM

Applicant hereby incorporates by reference the Sequence Listing material filed in electronic form herewith. This file is labeled "MLH-101.US.D1.xml", was created Feb. 16, 2024 and is 10,604 bytes.

BACKGROUND OF THE INVENTION

In hybridoma methods, B cells are fused to a fusion partner cell line, in order to create stable, laboratory-adapted cell lines that secrete antibodies derived from the B cells. This method has been used for decades to create high value mAbs that have had enormous utility and commercial potential. Despite its successes, it is important to consider that B cells producing such high value antibodies are often represented at very low frequency in an immune repertoire. Therefore, the hybridoma mAb cloning procedure is generally undertaken with thousands or millions of cells, in order to create polyclonal pools of cell lines that express a diversity of antibody structures. The task then is to identify which of those cells is secreting an antibody that has the desired specificity.

In the current state of the art, hybridoma cells must be kept separately from each other, to prevent cross contamination or cell overgrowth, while cell culture supernatants containing the antibodies produced by each hybridoma are analyzed. In order to be able to relate the findings of the antibody analysis to the cells that secreted them, i.e. if there is an antibody with desirable features and the objective is to identify the hybridoma that made it for sub-cloning and additional study, then supernatants also need to be kept separately from each other. Methods for this typically involve arranging the antibodies in an array format that reflects the arrays in which the hybridomas are being maintained. As a result, a large number of irrelevant hybridomas must be maintained in single or oligoclonal cultures while the antibodies are analyzed. Only when a hybridoma can be identified that secretes the antibody of interest (at that point, a "monoclonal antibody", or mAb) can the large number of irrelevant hybridomas be abandoned.

In addition, any hybridoma that secretes an antibody of the desired binding specificity must undergo additional steps of single cell cloning in order to identify progeny cell lines that stably maintain mAb secretion, which in itself requires the maintenance of hundreds of individual cells as well as individual assessments of mAb production.

These practical obstacles place severe limitations on the throughput of the hybridoma process, as hybridomas need individual care and feeding, supernatants must be obtained and analyzed individually (as well as replenished). As a result of limitations on the numbers of hybridomas that can be analyzed, valuable but rare mAbs may be practically impossible to generate. Furthermore, the expense of adapting hybridoma methods to high throughput can require substantial investments in robotics and automated liquid handling.

Further methods for the recombinant production of desirable proteins in yeast, *E. coli,* 293T cells, for example, require recombinant gene library construction and are generally displayed as immunoglobulin (Ig) fragments. An existing mammalian Ig cell display method that expresses full-length Igs on the surface of cells is described.[1] However, the need to interpose a gene isolation, cloning and expression step between the isolation of B cells from a mammalian host and the performance of assays to assess the binding and functional characteristics of the Ig molecules expressed by those B cells, and therefore to identify and isolate mAbs with desired activities, presents a substantial barrier to the generation of useful mAbs.

Hybridoma cells generated from B cells sometimes express Ig on their outer plasma membrane, yet these levels are generally low, unpredictable, and inconstant.[2] Methods to increase the amount of surface Ig expressed by hybridomas are known in which a fusion partner cell line that expresses B-cell receptor components is used to generate hybridoma cells that have enhanced surface Ig expression.[3] Yet, such methods constitutively trap Ig on the hybridoma cell surface at fixed levels, and therefore do not enable control of the timing and extent of Ig adherence the cell surface.

Association of Ig with hybridoma cells has been achieved by a variety of isolation methods, for example, Gel Microdrop (GMD) and Affinity Capture Surface Display (ACSD) methods.[4] In GMD methods, hybridoma cells are individually encapsulated in gel microdroplets that capture secreted Ig. In ASCD, hybridoma cells are labeled with biotin, which is used to adhere to the cell either an avidin-labeled capture antibody or an avidin bridge bound to a biotinylated capture antibody, which in turn can capture the secreted Ig. These methods require specialized equipment for processing and analysis, as well as multiple cell/droplet incubation and washing steps that add time and expense to the analysis.

These methods also require exposing the cells to stressful conditions and toxic reagents that may compromise cell viability and experimental yields.

Military, medical and other personnel who risk exposure to unfamiliar or unknown pathogens are frequently vulnerable to emerging and epidemic viral illnesses, and few anti-viral therapies are available to protect them from exposure. A critical obstacle to an effective anti-viral strategy is that it is hard to predict which viruses will be encountered. Another is that drug development can require years, once the pathogen has been identified[33]. Methods and compositions are needed to permit generation of new anti-viral drugs at a pace that allows real-time protection (i.e., counted in weeks, rather than years) of such personnel upon exposure to a new viral threat in the field. Patients who survive a viral infection produce antibodies that have potent and specific anti-viral activities[34,35]. These antibodies can be isolated as mAbs that can protect others exposed to the same pathogen, and are likely to be safe as drugs because of their fully human origin. But, most human mAb discovery methods require isolation and expression of antibody genes, a labor-intensive, technical process that requires substantial expertise and infrastructure[36]. Furthermore, conventional mAb discovery requires that viral antigens be fully characterized and adapted to virus-specific mAb binding assays. Thus, anti-viral mAb projects start with transporting patient blood and viral antigens out of the relevant field and into a non-epidemic area. This presents substantial practical, institutional, and regulatory barriers, which must be overcome before mAb discovery can even begin. Streamlined, efficient models of human mAb discovery are necessary that can overcome these obstacles and enable real-time discovery of therapeutic anti-viral mAbs.

The limitations on the rapid screening and obtaining of new mAbs and hybridomas also impacts recombinant production of proteins. Thus, compositions and methods are needed for more efficient identification of cells and their secreted proteins for diagnostic, therapeutic and research applications.

SUMMARY OF THE INVENTION

In one aspect, a composition comprises a nucleic acid molecule encoding an Anchor in operative association with regulatory sequences that direct expression of the Anchor on the surface of a cell containing the nucleic acid molecule. The Anchor is designed to form a first complex with a selected Linker. The Linker is designed to form a second complex with a target protein that is not recognized by the Anchor.

In another aspect, a recombinant vector is provided that comprises nucleic acid molecules as described herein.

In still a further aspect, a cell is provided having expressed on its outer plasma membrane surface an Anchor designed to form a first complex with a selected Linker. The Linker is designed to form a second complex with a target protein that is not recognized by the Anchor. This cell enables the target protein to be adhered to the cells upon secretion and binding to the Anchor-Linker complex. In certain embodiments, the cell may be a primary cell, a B lineage cell or an immortalized cell. The cell may further contain a nucleic acid molecule or vector as described herein.

In another aspect, a recombinant mammalian cell that expresses and secretes a selected target protein is characterized by having expressed on its outer plasma membrane surface an Anchor designed to form a first complex with a selected Linker. However, the Anchor is also designed so that it does not recognize, bind or form an complex with the target protein. The Linker is designed to form a second complex with the secreted target protein. This cell enables the target protein to be adhered to the cells upon secretion and binding to the Anchor-Linker complex.

In still another aspect, a hybridoma cell comprises anchored on its outer plasma membrane an Anchor designed to form a first complex with a selected Linker. The Linker is designed to form a second complex with a monoclonal antibody secreted by the cell, which monoclonal antibody is not recognized by the Anchor. This hybridoma cell enables its secreted monoclonal antibody to be adhered to the cell upon secretion and binding to the Anchor-Linker complex.

In yet another aspect, a method of making a cell comprises stably delivering to a selected cell a nucleic acid molecule or vector as described herein.

In a further aspect, a method of making a hybridoma cell comprises fusing a B lineage cell with an immortalized cell having expressed on its outer plasma membrane surface an Anchor designed to form an complex with a selected Linker. The Linker is designed to bind the antibody secreted by the B cell or a cell derived from a B cell, which antibody is not recognized by the Anchor.

In another aspect, a method of detecting or measuring a characteristic of a target protein, e.g., an antibody or a monoclonal antibody, secreted by a cell employs the nucleic acid molecules, vectors and cells described herein. A population of cells is provided wherein each cell of the population has expressed on its outer plasma membrane surface an Anchor designed to form a first complex with a Linker. The population is contacted with the Linker which is also designed to form a second complex with a target protein that is not recognized by the Anchor. The contacting step permits the Linker to adhere to the outer plasma membrane of the cells by binding in the first complex with the Anchor. These resulting cells are maintained in the presence of the Linker under conditions in which the cells secrete the target protein and the target protein binds to the cell-adhered Anchor-Linker first complex via formation a second complex with the Linker, thereby anchoring the target protein to the cell. Thereafter, certain characteristics of the target protein bound to the cell can be evaluated.

In still other aspects, a method is described for inducibly capturing a secreted mAb, in the form of an immune complex anchored by an Ig specific for the secreted mAb that is itself anchored to the surface of the hybridoma cell by a heterologous Ig moiety, on the surface of the cell that secretes it.

In another aspect, a method for identifying a monoclonal antibody that binds to a viral antigen comprises providing a population of hybridoma cells, each hybridoma cell comprising anchored on its outer plasma membrane an Anchor designed to form a first complex with a selected Linker; the Linker designed to form a second complex with a monoclonal antibody secreted by the cell, which monoclonal antibody is not recognized by the Anchor. The population is contacted with a multivalent Viral Antigen for a time sufficient for said viral antigen to bind to the cell-bound Anchor-Linker-mAb complex, resulting in a cell-bound Anchor-Linker-mAb-Viral Antigen complex. Additional immunoglobulins (Ig) secreted by the cell population are allowed to bind to other binding sites on the bound multivalent Viral Antigen, thereby forming a detectable immune complex of Anchor-Linker-mAb-Viral Antigen-Ig, which is structurally and functionally distinct from an immune complex that forms in the absence of a multivalent Viral Antigen.

Cells having bound thereto the Anchor-Linker-mAb-Viral Antigen-Ig complex are then identified based upon size, conformation, composition, and/or position or location of said complex on the cell surface.

Other aspects and variations of these compositions and methods are described further in the following detailed description of the preferred embodiments thereof.

BRIEF DESCRIPTION OF THE DRAWINGS

FIG. 2A shows that B5-6T cells after transfection successfully express the tandem murine scFv (BGS) on the cell surface. FIG. 2B shows that LCX cells after transfection successfully express the tandem murine scFv (BGS) on the cell surface.

FIG. 3A shows that B5-6T BGS fusion partner cells bind to rabbit IgG, whereas the B5-6T cells do not. FIG. 3B shows that LCX BGS fusion partner cells bind to rabbit IgG, whereas the LCX cells do not.

FIG. 4A shows that B5-6T BGS fusion partner cells bound to RAH bind to human IgG. FIG. 4B shows that LCX BGS fusion partner cells bound to RAH bind to human IgG.

FIG. 5A shows that B5-6T BGS fusion partner cells bind to human IgG (target protein) only in the presence of RAH (Linker) and not when RAH not present. FIG. 5B shows that LCX BGS fusion partner cells bind to human IgG (target protein) only in the presence of RAH (Linker) and not when RAH not present.

FIG. 6A shows that B5-6T BGS cells capture human IgG in the presence of RAH, whereas B5-6T cells do not. FIG. 6B shows that LCX BGS cells capture human IgG in the presence of RAH, whereas LCX cells do not.

FIG. 8A shows that B5-6T BGS fusion partner cells bound to the 6A human mAb via RAH as a Linker capture BoNT antigen but not RABV antigen. FIG. 8B shows that LCX BGS fusion partner cells bound to the 6A human mAb via RAH as a Linker capture BoNT antigen but not RABV GP.

FIGS. 9A and 9B are graphs of flow cytometry demonstrating expression of tandem murine scFv (BGS) on the surface of the 8C5 (FIG. 9A) and 9H2 (FIG. 9B) hybridomas, which secrete human IgG, as described in Example 4.

FIGS. 10A and 10B are graphs of flow cytometry showing that tandem murine scFv (BGS) mediates binding of rabbit IgG (Linker) to mAb secreting hybridomas 8C5 (FIG. 10A) and 9H2 (FIG. 10B) respectively as described in Example 4.

FIGS. 11A and 11B are graphs of flow cytometry showing that the expression of tandem murine scFv (BGS), in the presence of RAH as Linker, increases adherence of human IgG (target protein) to mAb secreting hybridomas 8C5 (FIG. 11A) and 9H2 (FIG. 11B).

FIGS. 12A and 12B are graphs of flow cytometry showing that RAH enhances capture of secreted human IgG (target protein) by hybridoma cell lines that express the tandem murine scFv (BGS). FIG. 12A shows that RAH as a Linker enhances capture of secreted monoclonal human IgG by 8C5 secreting hybridomas. FIG. 12B shows that RAH as a Linker enhances capture of secreted monoclonal human IgG by 9H2 secreting hybridomas.

FIG. 17A is an image of 8C5 BGS, stained with Alexa 488 (RABV). Many of the cells in the image have on their surface an immune complex that incorporates the Alexa 488-labeled RABV GP. Examination of the intensity and pattern of RABV GP staining on the 8C5 BGS cells reveals that the cells have different levels of signal, and that even many cells that are adjacent to each other have different levels of signal. FIG. 17B is an image of 8C5 BGS, stained with Alexa 488 and merged with the blue DAPI (nuclear) stained image. FIG. 17C is an image of B5-6T BGS stained with Alexa 488 (RABV). FIG. 17D is an image of B5-6T BGS, stained with Alexa 488 and merged with the blue DAPI stained image. Many of the 8C5 BGS cells show a fluorescent signal indicating the adherence of the RABV GP, whereas the B5-6T BGS cells do not. This correlates with the fact that the 8C5 BGS cells are secreting a mAb specific for RABV GP, whereas the B5-6T BGS cells are not secreting any mAb. This corroborates the flow cytometry data, indicating the presence of the three immune complex components formed on the surface of the cell and that mAb complex containing an antibody can be analyzed for its antigen-binding specificity, which is information that in turn can be cross-referenced with the cell that secretes it.

FIGS. 18A through 18C are three series of fluorescence photomicrographs. FIG. 18A shows B5-6T stained with DAPI (left panel); the cells cultured with RAH and an Alexa 488-labeled goat anti-rabbit IgG secondary antibody (middle panel); and the two images merged (right panel). FIG. 18B shows B5-6T BGS stained with DAPI (left panel); the cells cultured with RAH and an Alexa 488-labeled goat anti-rabbit IgG secondary antibody (middle panel); and the two images merged (right panel). FIG. 18C shows 8C5 BGS stained with DAPI (left panel); the cells cultured with RAH and an Alexa 488-labeled goat anti-rabbit IgG secondary antibody (middle panel); and the two images merged (right panel). This experiment was done to determine whether there are differences in the amount of functional Anchor protein expression by the cell lines, as indicated by its ability to bind RAH. The amount and distribution of the Alexa 488 label on the B5-6T BGS cells is essentially the same on every cell, demonstrating consistent expression of functional RAH on these cells. This result that is consistent with the flow cytometry data that demonstrates homogeneity of Anchor expression on the B5-6T BGS cell line. The distribution of the RAH on the surface of the 8C5 BGS cell lines shows how the presence of human IgG (secreted by the 8C5 BGS cells) can induce the formation of a RAH-containing immune complex on the surface of the cells that is structurally distinct from what forms in the absence of the human mAb (target).

As seen in FIG. 22B, the 293T BGS transfected was detected as the rightmost curve extended to a lower peak on the left, while the untransfected 293T BGS cells were detected as the higher leftmost curve.

DETAILED DESCRIPTION

Figures 1, 2A, 2B:
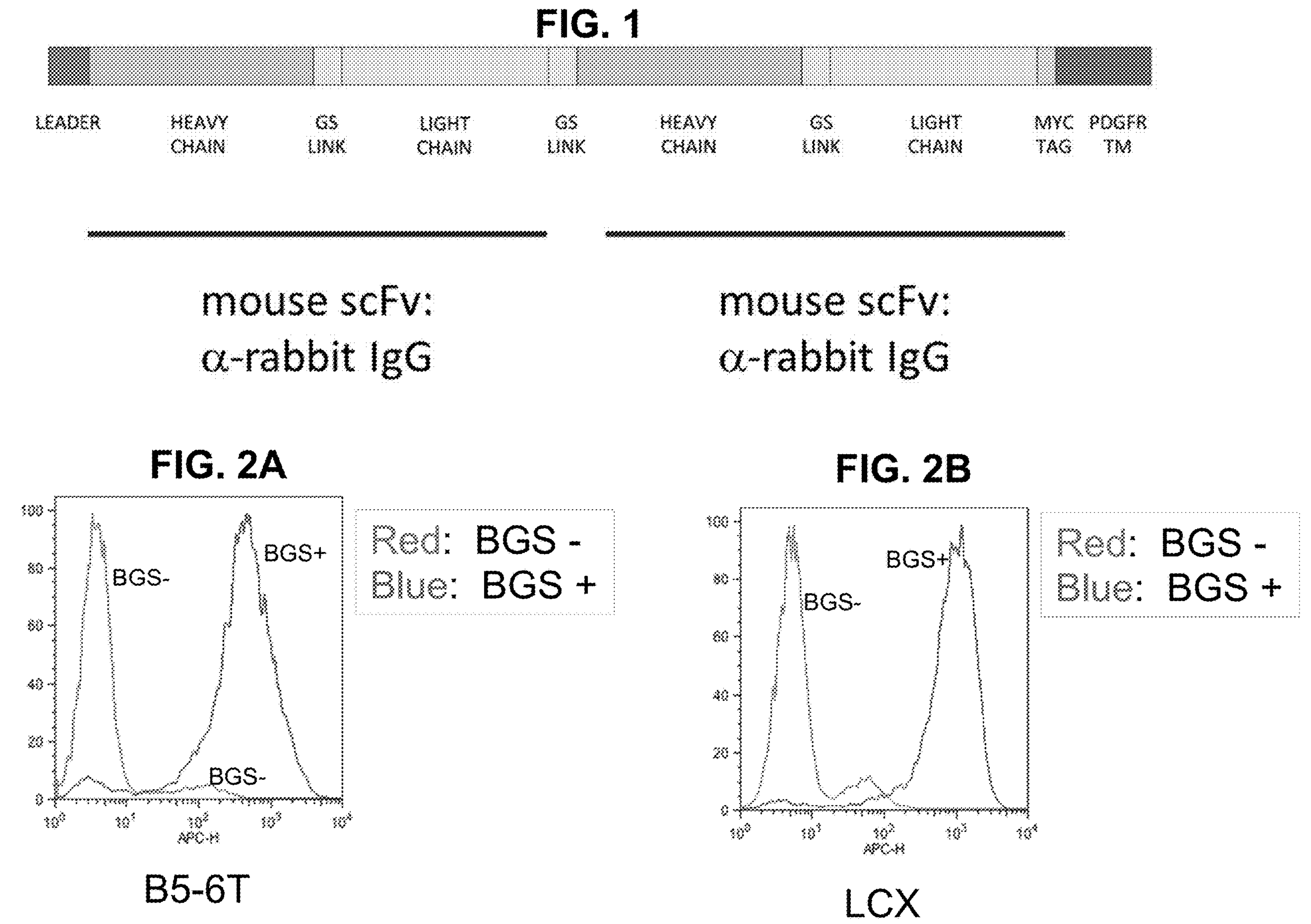
FIG. 1 is a schematic graph showing the gene map of a membrane Anchor comprising tandem murine anti-rabbit scFv linked by Gly-Ser linking amino acids (spacers), a PDGF receptor (PDGFR) transmembrane (TM) domain, a Myc tag and a leader sequence as described in Example 1.
FIGS. 2A and 2B are graphs of flow cytometry demonstrating that tandem murine scFv (which is an example of a B-cell Globulin Scaffold or BGS) was observed on the surface of the B5-6T and LCX fusion partner cell lines as described in Example 3.

The compositions and methods described herein provide for methods and compositions useful in the rapid screening and obtaining of new monoclonal antibodies (mAbs) and hybridomas, as well as the recombinant production of proteins. These compositions and methods permit more efficient identification of cells and their secreted proteins for diagnostic, therapeutic and research applications.

Disclosed herein are nucleic acid constructs and molecules, vectors of various types carrying the nucleic acid constructs or molecules, cells, cell lines, and methods that confer a variety of advantages on the production and identification of hybridoma cells and their secreted monoclonal antibodies. The compositions and methods eliminate the need to culture hybridomas individually, and reduce the barriers to maintaining and screening large numbers of cells. These compositions and methods enable the discovery of rare antibodies, while accelerating the rate of the mAb cloning process to isolate and characterize those with desirable characteristics. In addition, the methods and compositions reduce personnel and infrastructure costs. Further advantages of the methods and compositions described in detail herein include providing an extracellular mAb display for Ig screening, and enabling high throughput screening of polyclonal hybridoma populations by antigen-driven sorting methods (i.e., the mAb is physically associated with the cell that makes it). These methods and compositions are useful for phage display, yeast display, and mammalian display, which require recombinant mAb expression. These methods and compositions are useful to streamline hybridoma subcloning methods for optimizing Ig expression and stability and facilitating the identification of mAbs with rare binding specificities.

In one aspect, a method for human anti-viral mAb discovery as described herein is referred to as On-Cell mAb Screening (OCMS™). As described in greater detail herein, in one embodiment, the OCMS method is a hybridoma method. In conventional hybridoma methods, human B cells (which make the antibodies generated in response to e.g., a viral infection) are fused to fusion partner cells, which creates hybridoma cells that can grow in the laboratory. Each hybridoma secretes a single monoclonal antibody (mAb)[37]. Conventional mAb discovery requires testing thousands to millions of cells to find the one that makes the perfect mAb. In contrast, in the OCMS method, secreted mAbs are specifically adhered to the surfaces of the cells that produce the mAbs. Thus cells (e.g., hybridoma cells) that produce anti-viral antigen-specific mAbs can be identified and screened easily, simply by adding virus or viral antigens, because the mAbs on their surface will capture the virus. This streamlined work flow, from a subject's B cells to mAb screening and clone isolation, does not require gene cloning and expression, i.e., individual culture of each hybridoma cell generated and functional screening thereof. In one embodiment, the OCMS method can produce validated human mAbs in 6-8 weeks. This results in part from the fact that OCMS hybridomas are genetically stabilized for mAb secretion[22]. In another embodiment, the OCMS cells may be engineered for use in screening their mAbs for viral neutralization, in addition to virus binding. Using the OCMS method, the inventors have cloned human mAbs specific for poliovirus (PV) and the human NMDA receptor.

In another embodiment, the OCMS method is useful to discover mAbs using whole, unlabeled virus. As described in detail below, the OCMS method was used to create a universal assay for anti-viral mAb discovery. See Example 16 below. Briefly described, when hybridomas expressing anti-viral mAbs come into contact with the virus, tell-tale immune complexes form on the surface of the hybridomas. These complexes can be detected for high-throughput screening using High-Content Imaging (essentially, confocal microscopy accompanied by powerful image analysis software). Other conventional methods, e.g., flow cytometry, cell sorting, might also be used to detect these complexes and to enrich the mAb-expressing hybridoma.

In still other embodiments as described below, OCMS method may be used in recombinant cells that are not hybridomas.

Still other methods and compositions are described in detail below.

I. COMPONENTS AND DEFINITIONS USED IN THE COMPOSITIONS AND METHODS

In the descriptions of the compositions and methods discussed herein, the various components can be defined by use of technical and scientific terms having the same meaning as commonly understood by one of ordinary skill in the art to which this invention belongs and by reference to published texts. Such texts provide one skilled in the art with a general guide to many of the terms used in the present application. The definitions contained in this specification are provided for clarity in describing the components and compositions herein and are not intended to limit the claimed invention.

As used herein, the term "Anchor" refers to a protein sequence (or nucleic acid sequence encoding same) that comprises: (a) an extracellular region polypeptide which binds to, and forms a complex with, the Linker; (b) an optional polypeptide tag; and (c) a transmembrane amino acid sequence derived from an integral membrane protein. In still a more specific embodiment, the Anchor is encoded by the nucleic acid sequence of SEQ ID NO: 1.

In one embodiment of an Anchor, an "extracellular region polypeptide" is a single chain antibody variable region (scFv) that is able to specifically recognized and bind to a sequence on a Linker. In another embodiment, an extracellular region polypeptide is a tandem scFv formed of from 2, 3, 4, 5, or up to 6 or more scFvs, which may be separated from each other by a suitable "spacer" polypeptide, in which each scFv is designed to bind to a sequence on a Linker. In still another embodiment, an "extracellular region polypeptide" is a Fab having one or two free Fv regions when the Fab is expressed on the cell surface. In yet another embodiment, an "extracellular region polypeptide" is an antibody with one or two free Fv regions when expressed on the cell surface. In another embodiment, the extracellular region polypeptide of the Anchor is a single domain antibody. In another embodiment, the extracellular region polypeptide of the Anchor is a camelid antibody. In still another embodiment, the extracellular region polypeptide of the Anchor is an aptamer. In a specific embodiment, the extracellular domain polypeptide of the Anchor comprises alternating heavy chain Fv and light chain Fv sequences of each scFv, and "spacers" interposed between each chain. In another specific embodiment, the extracellular domain of the Anchor comprises alternating heavy chain Fv and light chain Fv sequences of each scFv, suitable spacers interposed between each chain.

By "polypeptide tag" is generally meant a short amino acid sequence incorporated into a heterologous polypeptide sequence that facilitates the identification and/or purification of the polypeptide sequence to which it is attached. A polypeptide tag is an optional component of the Anchor. In one example, a useful polypeptide tag for the Anchor is a Myc tag. In another example, a polypeptide tag is a FLAG Tag. In another embodiment, a polypeptide tag is a NE Tag. In still another embodiment, a polypeptide tag is a HA-Tag. In still another example, a polypeptide tag is a His or poly-His Tag. Other suitable tags include without limitation, a His Tag or poly-His tag, or a tobacco etch virus (TEV) protease recognition site. Still other suitable polypeptide tags may be used in the compositions and methods described herein.

By "cleavage tag" is generally meant a short amino acid sequence incorporated into a heterologous polypeptide sequence that allows the polypeptide to be cleaved at that site by an enzymatic or other mechanism. In one example, a useful cleavage tag is the 3C PreScission protease or PSP cleavage tag. In another example, a tag is an EKT (Enterokinase) cleavage tag. In another embodiment, a tag is a FXa (Factor Xa) cleavage tag. In still another embodiment, a tag is a TEV (tobacco echovirus) cleavage tag. In still another example, a tag is a thrombin cleavage tag. Still other suitable cleavage tags may be used in the compositions and methods described herein.

Another component of the Anchor is a transmembrane amino acid sequence derived from an integral membrane protein. An integral membrane protein generally has one or more segments that are embedded in the phospholipid bilayer of the cell. Most integral proteins contain residues with hydrophobic side chains that interact with fatty acyl groups of the membrane phospholipids, thus anchoring the protein to the membrane. Most integral proteins span the entire phospholipid bilayer.

The transmembrane spanning domains of these integral membrane proteins, which are from four to several hundred residues long, extend into the aqueous medium on each side of the bilayer. The membrane-spanning domains are α helices or multiple β strands. Examples of useful transmembrane proteins are selected domains from the integral membrane proteins that include, without limitation, type I transmembrane receptor molecules, such as platelet derived growth factor receptor (PDGF-R), epidermal growth factor receptor (EGF-R), integrins, insulin receptor, vascular endothelial growth factor receptor (VEGF-R) or other integral proteins.[5, 6] As an explicit example, see the sequence encoded by nucleotides 1603-1752 of SEQ ID NO: 1 (see Table I below).

As used herein, the term "spacer" refers to at least one to about 24 amino acids used to separate portions of the Anchor. Thus in various embodiments, the spacer is formed of a sequence of at least 2, 3, 4, 5, 6, 7, 8, 9, 10, 11, 12, 13, 14, 15, 16, 17, 18, 19, 20, 21, 22, 23, up to about 24 amino acids.

By "Linker" is meant an amino acid sequence (or polynucleotide sequence encoding same) that is designed to form a first complex with the Anchor, and a second complex with a target protein, which target protein is not recognized by the Anchor. The function of the Linker is thus to form a bridge (or link) between the Anchor that is expressed on the surface of the cell and the Target Protein that is secreted by the cell, thereby immobilizing the Target Protein and allowing identification of the cell that secretes that Target Protein as well as characterization of the Target Protein secreted by that cell. By "Immunoglobulin Linker" or "Ig Linker" is meant an amino acid sequence of an antibody or a fragment thereof (or polynucleotide sequence encoding same) that is designed to form a first immune complex with the Anchor, and a second immune complex with a target protein (the target protein not being recognized or bound by the Anchor). The function of the Ig Linker is thus to form a bridge (or link) between the Anchor that is expressed on the surface of the cell and the Target Protein that is secreted by the cell, thereby immobilizing the Target Protein and allowing identification of the cell that secretes that Target Protein as well as characterization of the Target Protein secreted by that cell. In one embodiment, the Linker can bind to both the Anchor and the Target Protein, under conditions wherein the Target Protein and the Anchor do not bind to each other in the absence of the Linker. In one embodiment, the Ig Linker is an antibody or antibody fragment. In specific examples shown herein, the Ig linker is the antibody fragment is Fv fragment, Fab fragment, Fv or a single chain Fv, or a single domain antibody, and recombinant versions thereof. In one embodiment, the Ig Linker is of a species heterologous to that of the Target Protein secreted by the cell on which the Ig Linker will form the first complex with the Anchor. In one embodiment Linker is a rabbit FAb.

As used herein, an "antibody or fragment" is a monoclonal antibody (mAb), a synthetic antibody, a recombinant antibody, a chimeric antibody, a humanized antibody, a human antibody, a CDR-grafted antibody, a multispecific binding construct that can bind two or more targets, a dual specific antibody, a bi-specific antibody or a multi-specific antibody, or an affinity matured antibody, a single antibody chain or an scFv fragment, a diabody, a single chain comprising complementary scFvs (tandem scFvs) or bispecific tandem scFvs, an Fv construct, a disulfide-linked Fv, a Fab construct, a Fab' construct, a F(ab')2 construct, an Fc construct, a monovalent or bivalent construct from which domains non-essential to monoclonal antibody function have been removed, a single-chain molecule containing one $V_L$, one $V_H$ antigen-binding domain, and one or two constant "effector" domains optionally connected by linker domains, a univalent antibody lacking a hinge region, a single domain antibody, a dual variable domain immunoglobulin (DVD-Ig) binding protein or a nanobody. Also included in this definition are antibody mimetics such as affibodies, i.e., a class of engineered affinity proteins, generally small (~6.5 kDa) single domain proteins that can be isolated for high affinity and specificity to any given target, and aptamers, polypeptide molecules that bind to a specific target. Wherever in this specification in the description of compositions or methods, the term "mAb" is used, it should be understood that this term may be replaced by any other form of antibody or antigen-specific/antigen-binding fragment to achieve the same or similar results. An antibody or a mAb might be an IgG, IgA, IgM, or IgE.

As used herein, "Target Protein" or "Target" refers to any naturally occurring or synthetic or recombinant amino acid sequence that is secreted by a cell. In one embodiment, the target is an antibody or a fragment thereof. In the examples below, the targets are monoclonal antibodies or a fragment thereof. In still other embodiments, the target protein can be any protein or polypeptide secreted by a cell. In one embodiment, Target protein is a mAb. In a further embodiment, Target protein is a Immunoglobin. In another embodiment, Target protein is a IgG. In yet another embodiment, Target protein is a IgA. In certain embodiments, Target protein is a human Ig.

By "cell" as used herein is meant a mammalian or non-mammalian cell that secretes a Target Protein. Thus, in one embodiment, the cell is a primary cell. In another embodiment, a cell is an immortalized cell. In certain embodiment, the cell is a mammalian cell. In other embodiments, the cell may be an insect cell, avian cell, bacterial cell, yeast cell or other non-mammalian cell. In one embodiment, the mammalian cell is a human cell.

By "B lineage cell" or "B cell" is meant a cell of the mammalian immune system capable of producing an immunoglobulin (e.g., an antibody or a fragment thereof). In the context of the inventions described herein, the B lineage cell produces and secretes a Target Protein, that is an antibody or a fragment thereof.

By "immortalized" cell is meant a cell that is capable of unlimited replication when maintained under suitable conditions. In one embodiment, an immortalized cell is a mammalian cell that is capable of being maintained in a proliferative state indefinitely in a laboratory. In one embodiment, an immortalized cell is a fusion partner cell, which can be fused to another cell (e.g., an non-immortalized cell) to generate a resulting immortalized cell. In another embodiment, a fusion partner cell can be an immortalized cell carrying a nucleic acid molecule expressing the Anchor (e.g., a BGS fusion partner). In another embodiment, the fusion partner cell does not express the BGS. As still another example, an immortalized cell is a hybridoma cell line which is generated by fusion between a B cell and a fusion partner cell.

In one embodiment, the selected cell contains a nucleic acid molecule expressing the Anchor. By "contains" in this context is meant that the nucleic acid molecule is carried stably or episomally in the cell due to its delivery by infection, retroviral transduction, electroporation or transfection. In another embodiment, the cell is transduced with a replication incompetent recombinant retrovirus that expresses the Anchor and becomes stably integrated into the host cell genome. In still other embodiments, the cell contains the Anchor due to electroporation with the nucleic acid molecule. A cell expressing the Anchor as described herein is referred to as a "BGS" (B-cell Globulin Scaffold) or OCMS cell line. In certain embodiments, the term "BGS" or "OCMS" refers to an Anchor. However, even where the Anchor and complex formed is not an immune complex, the term "BGS" "BGS+", "OCMS", or "OCMS+" nevertheless indicates that the cell is one expressing the Anchor and useful in forming the complexes to capture the secreted target. In certain embodiments, the terms "BGS−", or "OCMS−" indicates that the cell is one not expressing the Anchor.

Where the term "species" or "heterologous species" is used to define the origin of the Target Protein or the Linker or Ig Linker, the species may be selected, without limitation, from human, mouse, rat, goat, donkey, rabbit, guinea pig, cow, sheep, pig, camelid species, and chicken. Still other species of non-mammalian origin may be used depending upon the Target Protein selected. It is understood that the Ig Linker, Anchor and Target Protein, in certain embodiments are each of a heterologous species origin from each other.

As used herein, "complexing with", "binding to" or any grammatic variation thereof refers to forming an entity from association of components through specific interactions rather than random association of the components. The interactions included within a particular complex are limited to certain specific types of interactions that are defined by the components or parts of the components that are involved in the interaction as well the types of interactions or bonds formed. As would be understood by a skilled person, such specific interaction may include covalent bond (e.g., disulfide bond) and non-covalent bond (e.g., electrostatic interactions, hydrogen bonds, van der Waals forces and hydrophobic interactions). In a further embodiment, an "immune complex" as used herein refers to a complex comprising at least one interaction of antibody to its antigen. These definitions apply for both the use of these terms as nouns, verbs or adjectives, in this specification.

Figure 20:
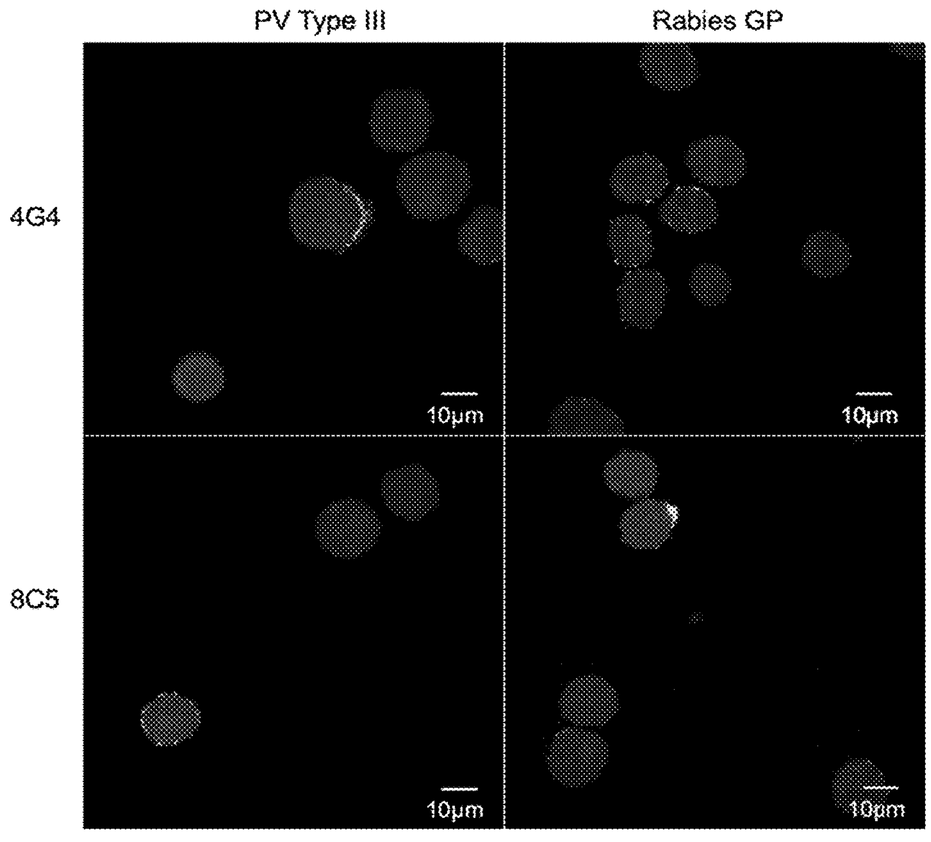
FIG. 20 shows 4 panels illustrating the universal anti-viral human mAb discovery method described herein and in more detail in Example 16. CAP-LIKE immune complex formation demonstrates anti-viral mAb expression. These OCMS hybridomas were incubated overnight with the rabbit anti-human Ig FAb, and either type 3 poliovirus (PV; left upper panel shows results with hybridoma cell line 4G4 BGS; left lower panels shows results with hybridoma cell line 8C5 BGS) or rabies virus glycoprotein (right upper panel shows results with 4G4 BGS; right lower panel shows results with 8C5 BGS). Hybridoma 4G4 BGS produces a human mAb that is specific for PV. Hybridoma 8C5 BGS produces a human mAb that binds rabies GP. The virus particles nucleate the formation of CAP-LIKE immune complexes on the cell surface, which are detected with FITC-labeled anti-human IgG secondary antibodies. In the absence of virus binding, cells display IgG spots evenly distributed over the cell membrane. The 4G4 BGS hybridoma forms a CAP-LIKE immune complex in the presence of PV, but not RABV GP. The 8C5 BGS hybridoma forms a CAP-LIKE immune complex in the presence of RABV GP, but not PV.

By the term "CAP-like immune complex" as used herein is meant that when a virus particle is present and is bound to a mAb on the surface of an OCMS hybridoma, additional mAbs secreted by that cell or other cells will also coat the virus particle. This creates tell-tale immune complexes (Anchor-Linker-mAb-virus-additional mAbs) that can be detected simply by observing the distribution of the mAbs on the hybridoma surface. In one embodiment, the virus is a multivalent antigen which has more than one epitopes which are able to be bound by an antibody. In certain embodiments, one of such epitopes might occur more than once on the virus. In one embodiment, the mAb as the Target protein is recognized and binds to an epitope different from those of the additional mAb. In another embodiment, the mAb as the Target protein is recognized and binds to an epitope same as the additional mAb but at different part of the virus. As used herein, the term "epitope" or any grammatic variations thereof refers to an antigenic determinant, which is part of an antigen that is recognized by the immune system, e.g., antibodies, B cells or T cells. Note that the diameter of viruses such as poliovirus (30 nm) is larger than the diameter of a mAb (about 15 nm). In CAP-like immune complexes, virions nucleate the formation of a large immune complex that sequesters all of the mAbs bound by the extracellular region polypeptide of the Anchor (e.g., tandem scFv) on one pole of the cell (see FIG. 20). Thus a CAP-LIKE complex can be identified by its size and position. In one embodiment, the tell-tale, virus dependent, CAP-LIKE structures are identified on the surface of OCMS hybridoma cells on the basis of their width (number of adjacent pixels labeled), fluorescent intensity, and distance from a stained (e.g., DAPI-stained) nucleus. In one embodiment OCMS hybridomas displaying virus-dependent CAP-like immune complexes are imaged in black-bottom CellCarrier plates in the Perkin-Elmer Operetta High Content Imaging System. Images are analyzed using PerkinElmer's Harmony High Content Imaging and Analysis Software data processing software and a spot detection algorithm. In one embodiment, CAP-LIKE complex formation is facilitated by aggregating the extracellular region polypeptide of the Anchor (e.g., tandem scFvs) prior to virus binding. In another embodiment, CAP-LIKE complex formation is facilitated by adding a polyclonal anti-mouse serum, in order to aggregate the murine Tandem scFvs prior to virus binding.

By the term "LAYERED immune complexes" refers to such complexes which may predominate when the mAb secretion level is low. The Anchor remain distributed across the cell membrane, but mAb (e.g., human IgG) is visible far from the plasma membrane, attached to the virion distal to the cell membrane. In LAYERED complexes, the virus binds mAbs in a layer that can be observed >30 nm from the cell surface. At this distance, fluorescent labels for mAb and Anchor will not merge, so the complexes can be assayed using the techniques described above for CAP-like complexes, e.g., by labeling the Anchor (e.g., Tandem scFv) with PE rabbit IgG, and the human mAb with a FITC secondary mAb. LAYERED structures are identified on the basis of green FITC signal, which only exists when the human mAbs are separated from the cell by a virus particle.

Figure 19:
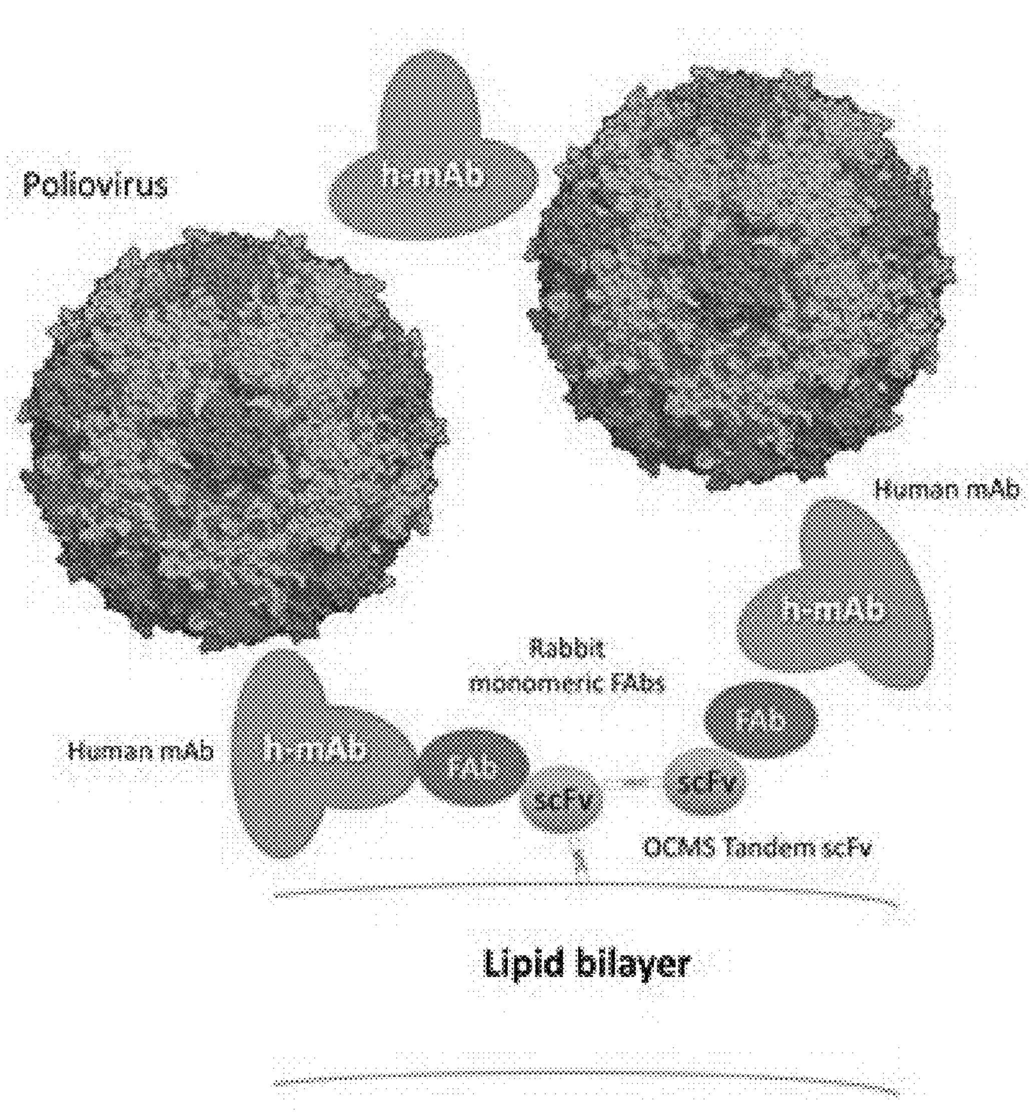
FIG. 19 is a schematic depicting a universal anti-viral mAb assay platform and discovery method. Virus binding is detected by the formation of tell-tale immune complexes on the hybridoma cell surface. Hybridoma cells express the BGS Anchor (in the schematic labeled as "OCMS Tandem scFv") and can be visualized with red fluorescent signal via conventional methods under a microscope, e.g., as described in Examples 4 to 7), which binds to a monovalent rabbit FAb (labelled as FAb in the schematic). Human IgG (labelled as h-mAb in the schematic can be visualized with green fluorescent signal under microscope, e.g., as described in Example 14) secreted by the hybridoma is captured by the Linker, in this case, it is a monovalent linker, such as rabbit FAb. Because the Linker depicted in this schematic is monovalent, immune complexes containing multiple h-mAbs will not form, unless a multivalent antigen is present. If the mAb is able to bind virus particles, then one of events occur. In one embodiment, the virions nucleate the formation of large immune complexes (CAP-LIKE complex). In another embodiment, mAbs bind the virions at sites separated from the plasma membrane by the virion (~30 nm) (LAYERED complex). This is a distance over which, for example, red and green fluorescent signals will not fuse to give a yellow signal, if the mAbs are labeled.

By the term "Universal anti-viral mAb discovery" or "Universal anti-viral mAb method or platform" refers to the ability to identify mAbs that bind diverse viruses using whole virions and a single, common set of diagnostic reagents, e.g., using OCMS hybridoma technology and automated High-Content Imaging. The principle of the assay is shown in FIG. 19. OCMS hybridoma technology immortalizes human B cells by fusing them to a laboratory-adapted fusion partner cell line, LCX, thereby creating hybridoma cells that express monoclonal antibodies derived from the human B cell. In one embodiment, the human B cells contain the Anchor. In another embodiment, the fusion partner cells contain the Anchor. The OCMS hybridomas display an Anchor (e.g., Tandem scFv) on their outer plasma membrane, which is able to bind to a Linker (e.g., rabbit IgG). When Linker (e.g., rabbit IgG) is added to the culture medium, it is captured by the Anchor (e.g., Tandem scFv). In one embodiment of the current OCMS method, a rabbit FAb specific for human IgG (Target Protein) is used, so that the human IgG secreted by a hybridoma is captured on the surface. In certain embodiments, these assays are performed with excess rabbit FAb in the medium, so that hybridomas only bind the human IgG they secrete. For example, excess rabbit FAb in the culture can capture human IgG secreted by other cells in the culture while that IgG is further in distance from the secreting hybridoma of interest. Alternatively, the Linker bound by the Anchor on a hybridoma can be selected to bind only to the mAb or IgG that the hybridoma secretes. The reagents are non-toxic, so the experiments are performed on live cells; cells expressing the desired mAbs can be isolated using flow cytometry or other common methods. In an optimal Universal anti-viral mAb discovery platform, the input is a sample of convalescent B cells and a sample of the pathogenic virus. The output is a hybridoma RNA sample that can be used to manufacture the mAb for clinical, diagnostic, therapeutic, or research application. In one embodiment, the overriding goal is epidemic interruption: to identify mAbs from those who have survived a viral infection and deliver those to military or other personnel and populations in the form of RNA therapeutics, fast enough to halt the spread of an epidemic[40]. It would be understood by one of skill in the art that in certain embodiments, "mAb", "IgG" and "human IgG" can be used interchangeably.

By "Stabilized Hybridoma Expression Library or SHEL™" as used herein is meant a library of hybridoma cells that only secrete mAbs. In one embodiment, the SHEL population does not include substantial or significant numbers of non-secreting cells populations. In one embodiment, the SHEL population does not include non-secreting cells populations. In contrast, conventional hybridoma libraries cannot be maintained in polyclonal culture, because the hybridomas that secrete mAbs tend to be overgrown by the non-secreting hybridoma cells, which proliferate faster. A SHEL library is created by use of the OCMS methods. The OCMS method permits polyclonal hybridoma populations to be analyzed and sorted to create populations that only secrete mAbs and can therefore be maintained in culture indefinitely and cryopreserved as necessary. SHEL populations thus do not need to be discarded after screening and have the advantage of increasing the number of tests that can be performed on each hybridoma. See Example 12.

As used herein, the term "in operative association" or "operably linked" describes the relationship of the components of the nucleic acid molecule to enable expression of the desired gene or nucleic acid sequence that encodes a selected protein, e.g., the Anchor, or any recombinant protein, etc., in the desired location on a plasma membrane of a mammalian cell. For simplicity, the encoding nucleic acid sequence is referred to as the "transgene". The Anchor transgene is operatively linked to regulatory components in a manner which permits transcription of the transgene encoding the Anchor, translation, appropriate intracellular trafficking, and/or expression in a host cell. As used herein, "in operative association" or "operably linked" sequences include both expression control sequences that are contiguous with the transgene of interest, e.g., the Anchor or any recombinant protein intended for expression, and expression control sequences that act in trans or at a distance to control the gene of interest.

Expression control sequences for use in the nucleic acid sequences described herein include appropriate transcription initiation, termination, promoter and enhancer sequences; efficient RNA processing signals such as splicing and polyadenylation (polyA) signals; sequences that stabilize cytoplasmic mRNA; sequences that enhance viral transduction efficiency and nuclear-cytoplasmic translation efficiency (i.e., Kozak consensus sequence); sequences that enhance RNA translation efficiency, sequences that engender improved protein processing, expression yields, and stability; and when desired, sequences that enhance secretion of the encoded product. A great number of expression control sequences, including promoters which are native, constitutive, inducible and/or tissue-specific, are known in the art and may be utilized.

Suitable constitutive or inducible promoter sequences for use in the nucleic acid sequences are available from a variety of commercial sources, including, without limitation, Invitrogen, Clontech and Ariad. Many other systems, e.g., native promoters, tissue-specific promoters, etc., have been described[7, 8, 9] and can be readily selected by one of skill in the art. In a specific embodiment, the BGS-encoding nucleic acid sequences are amenable to regulation through the operative association with nucleic acid sequences that can control their expression level through promoter/enhancer activation, promoter/enhancer repression, or epigenetic factors (such as expression of specific non-coding RNA molecules).

In one embodiment, a vector may be used to deliver the Anchor coding sequence as well as the regulatory sequence operably linked thereto into a cell, e.g., a fusion partner cell, a B cell, or a hybridoma cell. As used herein, a vector may include any genetic element including, without limitation, naked DNA, a phage, transposon, cosmid, episome, plasmid, bacteria, virus or nanoparticle. By "virus vector" is meant a non-pathogenic virus or a non-replicating virus. In one embodiment, a desirable viral vector may be a retroviral vector, such as a lentiviral vector. In another embodiment, a desirable vector is an adenoviral vector. In still another embodiment, a suitable vector is an adeno-associated viral vector. A variety of useful lentivirus vectors, as well as the methods and manipulations for generating such vectors for use in transducing cells and expressing heterologous are described[10]. Many known vectors may be employed by one of skill in the art to create components of the compositions and methods described herein given the teachings of this specification. Use of any such vector or components is encompassed by these teachings.

By "selectable marker protein" is meant a protein conventionally used for detection of components of recombinant sequences. In one embodiment, such selectable markers are antibiotic resistance proteins. In one embodiment the selectable marker confers resistance to puromycin. In one embodiment the selectable marker confers resistance to blasticidin. Another suitable marker is a kanamycin resistance (KanR), which confers mammalian cells with resistance to the antibiotic G418. Still other selectable markers are known to one of skill in the art and suitable for use as described herein.

As used herein, "labels" or "reporter molecules" or "detectable label components" are chemical or biochemical moieties useful in association with the Anchor, the Linker, the secondary antibody, the Target (e.g., mAb), the molecular (e.g, antigen) recognized by the Target, or other binding partner protein of the Target Protein, that alone or in concert with other components enable the detection of a target. Such labels or components include, without limitation, fluorescent agents, chemiluminescent agents, chromogenic agents, quenching agents, radionucleotides, enzymes, enzymatic substrates, cofactors, inhibitors, radioactive isotopes, magnetic particles, and other moieties known in the art. In certain embodiment, the "labels" or "reporter molecules" are covalently or non-covalently associated with the ligand. Such labels are capable of generating a measurable signal alone, e.g., radioactivity, or in association with another component, e.g., an enzymatic signal in the presence of a substrate. Methods of attaching the labels to the antigens are conventional.

The methods used to construct any embodiment the compositions (nucleic acid molecules or cells) are known to those with skill in nucleic acid manipulation and include genetic engineering, recombinant engineering, and synthetic techniques. Such techniques include conventional cloning techniques of cDNA such as those described in texts[11], use of overlapping oligonucleotide sequences of the virus genomes, polymerase chain reaction, and any suitable method which provides the desired nucleotide sequence. Standard transfection and co-transfection techniques are employed, e.g., $CaPO_4$ precipitation techniques. Other conventional methods employed include homologous recombination, methods of measuring signal generation, and the like.

By "4G4" is meant a hybridoma cell line that secretes a human mAb that binds all three Sabin PV serotypes. In certain embodiments, "4G4" refers to the mAb secreted by the 4G4 cells. In one embodiment, a 4G4 cell may express OCMS, BGS or another Anchor.

By "8C5" is meant a hybridoma cell line that secretes a human mAb that binds the rabies glycoprotein. In certain embodiment, "8C5" refers to the mAb secreted by the 8C5 cells. In one embodiment, an 8C5 cell may express OCMS, BGS or another Anchor.

The terms "a" or "an" refers to one or more. For example, "an expression cassette" is understood to represent one or more such cassettes. As such, the terms "a" (or "an"), "one or more," and "at least one" are used interchangeably herein.

As used herein, the term "about" means a variability of plus or minus 10% from the reference given, unless otherwise specified.

The terms "first" and "second" are used throughout this specification as reference terms to distinguish between various forms and components of the compositions and methods.

The words "comprise", "comprises", and "comprising" are to be interpreted inclusively rather than exclusively, i.e., to include other unspecified components or process steps.

The words "consist", "consisting", and its variants, are to be interpreted exclusively, rather than inclusively, i.e., to exclude components or steps not specifically recited.

As used herein, the phrase "consisting essentially of" limits the scope of a described composition or method to the specified materials or steps and those that do not materially affect the basic and novel characteristics of the described or claimed method or composition. Wherever in this specification, a method or composition is described as "comprising" certain steps or features, it is also meant to encompass the same method or composition consisting essentially of those steps or features and consisting of those steps or features.

II. THE COMPOSITIONS

As described in more detail below and in the examples, the various compositions and components are useful in preparing certain cells that secrete a Target Protein, and useful in methods to capture the Target Protein on the outer plasma membrane of the cells as part of a multi-part complex. The multi-part complex includes a "first" complex between the cell-bound Anchor and a Linker, and a "second" complex formed between the bound Linker and the Target Protein. Still other complexes can be part of the multi-part complex bound to the cell. For example, as described below, where the Target is an antibody, a "third" complex can be formed between the bound Target Protein and its antigen. Also, a "fourth" complex can be form between the bound antigen with additional Targets. By utilizing the teachings herein, it is possible to physically attach a cell to the Target Protein, e.g., mAb, IgG, IgA, or human Ig, that it secretes. That Target will adhere to the cell that secretes the Target only it if the Linker of the appropriate specificity is bound to the cell via the Anchor by forming the first and second complexes.

Thus, one composition is a nucleic acid molecule useful for construction of the desired cells for use in the methods described below. This nucleic acid molecule encodes an Anchor in operative association with regulatory sequences that direct expression of the Anchor on the surface of a cell containing the nucleic acid molecule. The Anchor is designed to form a first complex with a selected Linker; and the Linker is designed to form a second complex with the selected Target Protein. It is a requirement of this nucleic acid molecule that the Anchor it expresses does not bind substantially to the Target Protein.

Because the Anchor comprises an extracellular region polypeptide that binds the Linker, that polypeptide must form a complex only with the Linker. For example, where the extracellular region polypeptide comprises a single chain antibody variable region (scFv) that specifically binds a sequence on the Linker (or any of the other extracellular peptides identified in the definition above), that polypeptide must not bind in any way with the Target Protein. As indicated in the examples, the scFv of the Anchor can identify only certain species of immunoglobulins, e.g., rabbit immunoglobulin. Thus, provided that the Linker is a rabbit antibody (or a rabbit species antibody specific for the Target Protein), and the Target Protein is not a rabbit species antibody, then the Anchor will bind the Linker and not the Target Protein. As noted in the examples and above, the Anchor's extracellular region can comprise alternating heavy chain Fv and light chain Fv sequences of each scFv, and spacers interposed between each chain. Sec, e.g., FIG. 1.

Also part of the nucleic acid molecules described herein are the regulatory sequences including a promoter, a leader sequence, an optional enhancer, and/or an optional sequence encoding a selectable marker protein, which are in operative association with the nucleic acid sequence encoding the Anchor and permit the Anchor to be expressed in a selected cell and optionally identified by the marker protein. The marker protein can be associated with the same regulatory sequences used to express the Anchor or additional regulatory sequences, as a design preference.

In certain embodiments, the promoter controlling expression of the Anchor is an inducible promoter or a repressible promoter. This embodiment permits the Anchor expression to be controlled by use of conventional inducer or repressors where such control is desired for use in the methods below.

The regulatory sequences, polypeptide tag, cleavage tag, transmembrane sequence, spacers and other portions of the Anchor may be selected from the lists provided in the definitions of these components or associated citations provided above and assembled as instructed herein and in the examples below. Thus, in one embodiment, the nucleic acid molecule comprises the Anchor components described in Table 1 below. For example, the Anchor comprises a tandem scFv separated by Gly-Ser spacers which are capable of binding to an Ig Linker which is a rabbit anti-human antiglobulin, the polypeptide tag is a Myc Tag, the transmembrane protein is derived from the PDGF integral membrane protein.

It may also be advantageous to be able to remove from the surface of the cell, the complex formed on the surface of the cell that expresses the Anchor sequence, by the interaction of the Linker, and the mAb secreted by the cell. In one embodiment, removal of the complex is desirable, especially if the secreted mAb is bound to an antigen. For example, if a cell is exposed to a population of different antigens, and one of the antigens is noted to bind to the mAb, then separating the entire complex from the surface of the cell and analyzing the composition of the molecules in the complex (for example, by mass spectroscopy methods) enables identification of the antigen bound by the mAb. For this reason, the incorporation of a cleavage tag on the Anchor molecule is useful. In one embodiment, the Anchor comprises a tandem scFv separated by Gly-Ser spacers which are capable of binding to an Ig Linker which is a rabbit anti-human antiglobulin; the affinity tag is a Myc Tag; the transmembrane protein is derived from the PDGF integral membrane protein; and a TeV cleavage tag is located between the tandem scFv and the transmembrane domain.

In certain embodiments, the Linker is an antibody or antibody fragment. While the antibody or fragment can be any of those described above, in one embodiment, the antibody fragment is Fv fragment. In another embodiment, it is a Fab fragment. In still additional embodiments, the Ig Linker is an Fv or a single chain Fv, or a single domain antibody, and/or a recombinant version of any of these examples.

In still other embodiments, the Anchor is designed with the Linker and Target Protein in mind so that the Linker is of a mammalian species heterologous to the species of the Anchor; and the Target Protein is of a species heterologous to the Linker and to the Anchor.

As can readily be seen from this teaching, a wide variety of Anchors and nucleic acid molecules that express the Anchors can be constructed depending upon the selection of the Target Protein, the cell and the other components useful in the methods described herein.

Specifically, it is evident that, in certain embodiments of the invention, the species-binding specificity of the Anchor protein could in practical terms be directed against any species of Linker antibody, as long as the species of the Linker antibody is different from the species of the antibody that is secreted by the cell expressing the Anchor. In still another embodiment, the Linker antibody is not specific for the species of antibody incorporated into the Anchor protein. In one embodiment, the scFv moieties in the Anchor domain are of murine origin and the Linker Ig is of rabbit origin and exhibited strong binding to human Ig but little or no binding activity against the murine scFv moieties. This set of reagents is suitable to inducibly adhere a secreted human Ig to the surface of a cell line that secretes it. In another embodiment, the Anchor antibody domains are murine scFv domains that are specific for a camelid antibody, and the camelid antibody is specific for a bovine antibody, but with no reactivity for murine Ig. This set of reagents is suitable to inducibly adhere a secreted bovine Ig to the surface of a cell that secretes it. In another embodiment, rabbit scFvs specific for a camelid antibody are incorporated into an Anchor polypeptide, and the camelid antibody is specific for murine Ig. This set of reagents is suitable to inducibly adhere a secreted murine Ig to the surface of a cell that secretes it. An additional set of reagents includes an Anchor protein expressing murine scFv sequences specific for a camelid antibody, the camelid Ig specifically binding rabbit Ig but not murine Ig. This set of reagents is suitable to inducibly adhere a secreted murine Ig to the surface of a cell that secretes it. Additional examples are readily apparent to anyone skilled in the art.

Yet another component useful in the methods described below is a vector comprising a nucleic acid molecule encoding an Anchor in operative association with regulatory sequences that direct expression of the Anchor on the surface of a cell containing the nucleic acid molecule. The Anchor is designed to form a first complex with a selected Linker; and the Linker is designed to form a second complex with a target protein that is not recognized by the Anchor. In certain embodiments, the vector carries any of the nucleic acid molecules described herein or the construction of which is taught generally or specifically by the specification and examples. The vector is a plasmid in one embodiment. In other embodiments, a recombinant virus vector, such as a lentivirus is preferred. The vectors are selected from among many commonly used vectors for transportation of the nucleic acid molecule into a cell and may include a selectable marker protein. Such vectors are transfected or infected into the selected cell at the election of the person of skill in the art. Electroporation to insert the nucleic acid molecule into cells is another embodiment for use in providing the cells useful in the methods described herein.

Thus the compositions provided herein are a variety of cells that each have expressed on its outer plasma membrane surface an Anchor designed to form a first complex with a selected Linker; and the Linker is designed to form a second complex with a target protein that is not recognized by the Anchor. In certain embodiments, these cells contain any of the nucleic acid molecules described herein. In other embodiments, these cells contain any of the vectors described herein. In still other embodiment, the compositions include a SHEL population of hybridomas substantially enriched for secretion of mAbs. In one embodiment, the population is created by use of the OCMS methods described herein.

In one embodiment, before the cell is used in some of the methods for isolating or identifying the Target Protein, the cell comprises on its cell surface the extracellular portion of the Anchor. In another embodiment, the cell, which has been exposed to the Linker comprises on its outer plasma membrane surface the first complex formed between the Anchor and Linker. As an example, the cell expresses as Anchor a murine anti-rabbit antibody or just the scFv thereof.

In another embodiment, the cell contains on its cell surface the Anchor's scFv bound in a complex with sequences on the Linker, which is a heterologous antibody or antibody fragment to that of the Anchor. For example, the Linker is a rabbit anti-human antibody in one embodiment. Thus the cell has bound to its surface the murine scFv Anchor construct bound to the rabbit Linker, which is, for example, an Fv fragment, Fab fragment, Fv or a single chain Fv, or a single domain antibody, and recombinant versions of a rabbit anti-human antibody.

In still another embodiment, a cell comprises on its outer plasma membrane surface a multiple complex comprising the Anchor bound to the Linker, and when in the presence of the secreted Target Protein, e.g., an antibody, the complex further contains the Linker also bound to the Target Protein.

As stated above, in certain embodiments, the Linker is of a species heterologous to the species of the Anchor; and the Target Protein is of a species heterologous to the Linker and to the Anchor. As shown in the examples, the Anchor is derived from a murine antibody; the Linker is derived from a rabbit anti-human antibody; and the Target Protein is a human antibody.

In yet a further embodiment, a cell contains on its surface an even more layered complex, e.g., that formed by the interactions between the Anchor-Linker-Target Protein (antibody), which can be further linked to the antigen to which the antibody is directed, e.g., a naked antigen or an antigen that is labeled for further use in isolating, quantifying or identifying the Target Protein and the cell from which it was secreted. Thus, an additional embodiment is a cell-based immune complex that comprises the following components: a cell, an Anchor protein on the cell surface, a Linker bound to the Anchor protein, and a mAb that has been secreted by the cell.

Yet another embodiment is a cell-based immune complex that comprises the following components: a cell, an Anchor protein on the cell surface, a Linker bound to the Anchor protein, a mAb that has been secreted by the cell, and an antigen to which the secreted mAb binds. In still other embodiments, the antigen within this complex is associated with or contains a label (a molecular structure or modification, such as a biotin, fluorescent molecule, or magnetic bead) that enables identification of cell-based immune complexes of the present invention that contain an expressed mAb specific for the labeled antigen. Alternatively, in other embodiments, the complex contains a similarly labeled molecule that has affinity for the antigen bound by the mAb and thus enables identification of cell-based immune complexes described herein that contain an expressed mAb specific for the labeled antigen.

In still other embodiments, any of these cells are cells immortalized by use of conventional immortalization techniques performed on the cell expressing the Anchor. Alternatively, an already immortalized cell is manipulated to contain the nucleic acid molecules or vectors described above, so that the resulting immortalized cell expresses the Anchor, and/or any of the additional components of the multi-immune complexes described herein. Where the cell is immortalized and expresses a selected Anchor and is suitable for fusing to primary cells to create an immortal hybrid cell, it is referred to as a fusion partner cell line.

In still other embodiment, any of the above cells may be a B lineage cell. Other embodiments of the cells differ in the species of the cell, e.g., human, other mammalian, or non-mammalian. Similarly, in some embodiments, the cells contain nucleic acid molecules in which the regulatory sequences permit the Anchor expression in the cell to induced or repressed during performance of any of the methods.

In still another embodiment, any of the cells described above is a recombinant mammalian cell which was manipulated by genetic engineering techniques to recombinantly express and secrete any desired Target Protein that has therapeutic, research or diagnostic use. In certain embodiments, the Target Protein is not an antibody, but can be used in the methods described below for high level production or analysis of any selected protein.

In one specific embodiment, the compositions and components described herein provide a hybridoma cell comprising an Anchor anchored on its outer plasma membrane, the Anchor designed to form a first immune complex with a selected immunoglobulin (Ig) Linker; the Linker designed to form a second immune complex with a monoclonal antibody secreted by the cell, which monoclonal antibody is not recognized by the Anchor. In another embodiment, the hybridoma cell further comprises on its cell's outer plasma membrane surface a first immune complex comprising the Anchor and the Ig Linker. This cell is provided when the original cell expressing the Anchor is in the presence of the Ig Linker. In one more specific embodiment, the Ig Linker is an antibody or antibody fragment, or a Fv fragment, Fab fragment, Fv or a single chain Fv, or a single domain antibody, and/or a recombinant version thereof.

In another embodiment, a hybridoma cell is provided that further comprises on its cell's outer plasma membrane surface a multi-component immune complex comprising the Anchor bound to the Linker, with the Linker bound to the monoclonal antibody that is secreted by the hybridoma. The cell can be isolated when the original cell expressing the Anchor is in the presence of the Linker and the hybridoma is secreting the mAb. As described above, these hybridoma cells are those in which the Linker is of a mammalian species heterologous to the species of the Anchor; and wherein the monoclonal antibody is of a species heterologous to the Linker and to the Anchor.

In still another embodiment, the hybridoma cell comprises on its cell's outer plasma membrane surface an immune complex comprising the Anchor bound to the Linker, which is bound to the monoclonal antibody secreted by the cell line, which further forms an immune complex with the antigen specifically recognized by the monoclonal antibody. This cell can be isolated when the original cell expressing the Anchor is in the presence of the Linker; the hybridoma is secreting the mAb; and the cells are in the presence of the antigen.

In a specific embodiment of the compositions useful in the methods described below is a mammalian cell line that secretes a mAb and captures that mAb on its outer plasma membrane in an immune complex that includes (1) as Anchor an antibody attached to the outer plasma membrane of the hybridoma cell line, which is specific for a species of antibody different than the species of antibody secreted by the hybridoma and (2) and the Linker, which is an antibody of the species recognized by the Anchor, and is itself specific for the species of the mAb secreted by the hybridoma. For example, the monoclonal antibody secreted by the hybridoma is a human antibody; the Anchor comprises a murine anti-rabbit scFv specific for a rabbit immunoglobulin and the Linker is a rabbit anti-human species antibody or binding fragment.

As described herein, in one embodiment a cell line that is used to generate a fusion partner is a cell line that expresses a mutant glycoprotein 130 (gp130), a cytokine receptor molecule that constitutively activates the signal transducer and activator of transcription-3 (STAT3) protein and can induce cytokine independent proliferation of cytokine-dependent cell lines. Significantly, gp130 is the shared element of a family of heterodimeric class I cytokine receptors for diverse cytokines, such as IL-6 and IL-11, but also include cardiotrophin 1 (CT-1), leukemia inhibitory factor (LIF), ciliary neurotrophic factor (CNTF), and oncostatin M (OSM). The mutant form of gp130 has deleted 5 amino acids from Y-186 to Y-190 (YSTVY deleted), termed gp130 ΔYY.[19]

In certain aspects of the compositions and methods described herein, a fusion partner cell line that constitutively expresses gp130 ΔYY and expresses an Anchor is useful in a number of methods. The amount of gp130 ΔYY expressed by a living cell or cell population can be readily assessed by standard immunofluorescence methods and fluorescence activated cell sorting (FACS), and cells within a population that have lost expression of the gp130 ΔYY can be readily identified and removed by the same method. As a result, by a simple test, it can be readily determined prior to a cell fusion experiment whether all of the fusion partner cells in a population express the required constitutive cytokine signaling activity.

The level of gp130 ΔYY-induced signaling is not expected to change substantially as culture conditions change, which will reduce the stress on the cultured cells, because the amount of cytokine activity will not depend on the accumulation of secreted cytokine in the culture medium. Furthermore, hybridoma cell populations created by fusion of a gp130 ΔYY-expressing fusion partner cell line with a B-cell is readily analyzed by standard immunofluorescence methods, even in the earliest stages of hybridoma cell creation and expansion, for example, by adding a fluorescently-labeled gp130 antibody to the culture medium and analyzing with fluorescence microscopy. This has immediate benefit, because it will allow cells that express important mAbs, but not the autonomous cytokine activity that is critical for stable mAb expression, to be identified and provided with special handling.

One of the most substantial benefits of expressing IL-6 or IL-11 in fusion partner cell lines is that cytokine expression can stabilize expression of human mAbs in hybridomas that have been formed through cell fusion with primary human B cells.[13, 22] This effect is especially strong when the cytokine is expressed in heteromyeloma cell lines that also express an ectopic hTERT gene. A fusion partner cell line expressing hTERT and gp130 ΔYY, but without IL-6 or IL-11, is also be useful for human mAb cloning.

In one embodiment, the LCX cell line is provided, which is a K6H6/B5 cell line transduced with a retroviral hTERT gene and a retroviral gp130 ΔYY gene. The LCX cell line, strain designation 03.06.17, was deposited on Mar. 24, 2017 under Accession No. PTA-124063 with the American Type Culture Collection (ATCC), located at 10801 University Boulevard, Manassas, VA 20110 USA. The level of gp130 ΔYY is easily monitored in this cell line and its progeny. The LCX cell line is effective in cloning human mAbs through cell fusion with primary human B cells. When this LCX cell line is used to also express the Anchor as described in Example 1, it is a novel fusion partner cell line, referred to as LCX-BGS. An exemplary LCX-BGS cell line, strain designation 03.06.17, was deposited on Mar. 24, 2017 under Accession No. PTA-124062 with the American Type Culture Collection (ATCC), located at 10801 University Boulevard, Manassas, VA 20110 USA. LCX BGS is suitable for use as a fusion partner to clone human mAbs. LCX BGS can be fused with B-lymphocytes to generate hybridomas that secrete human mAbs and are able capture those mAbs on their outer plasma membrane using the methods described herein.

As both the gp130 ΔYY and BGS moieties can be assessed simultaneously on the surface of the LCX-BGS cell line by flow cytometry, this cell line is particularly suited for adaptation to high throughput, industrial scale application of the hybridoma method for human mAb cloning. LCX is an example of a cell line that expresses a constitutively active cytokine receptor, gp130 ΔYY, which enables efficient cloning of human mAbs in the presence of hTERT and in the absence of ectopically expressed IL-6 or IL-11. LCX-BGS is an example of a cell line that constitutively expresses gp130 ΔYY and a suitable Anchor. The cell line is an embodiment of a cell that overcomes important limitations in the use of fusion partner cell lines that express secreted cytokines and is ideal for adaptation to industrial scale, high throughput human mAb cloning methods.

The embodiment of cell lines, LCX and LCX-BGS enables better standardization of cytokine signaling activity expressed by fusion partner cell lines because the amount of gp130 ΔYY can be assessed by flow cytometry on populations of living cells. Additionally, this cell lines permits assessment of the preservation of fusion partner cell line gp130 ΔYY expression on live cell cultures for quality control monitoring. It further permits fusion partner cell line optimization, such as by titrating the amount of gp130 ΔYY expression (and the magnitude of cytokine signaling) or by assessing the proportion of hybridoma cells that maintain expression of the gp130 ΔYY transgene.

Cells similar to LCX-BGS or LCX permit real-time assessment of the cytokine activity (as a result of gp130 ΔYY expression) in polyclonal cell cultures, including small cultures (fewer than 100 cells) as are often the case in typical hybridoma experiments. These cells are also useful in real time identification of hybridoma that do not possess constitutive cytokine signaling, which is a surrogate for instability of mAb expression, in order to give those cells special handling. Finally LCX-BGS enables use of more consistent growth conditions for fusion partner cell lines and hybridomas derived from them, for example, more stable levels of cytokine signaling that do not vary significantly depending on the density of cells in the culture medium, the time that the cells have been in the culture, and when culture medium has been refreshed or replaced.

Still other cell lines and fusion partner cell lines can be developed according to the teachings described herein.

Still other aspects include a hybridoma mAb expression library comprising two or more hybridoma cell lines described herein, a population of hybridoma cells derived from the methods described below, a population of fusion partner cells derived from the method described below, or a population of hybridoma cells derived from the fusion partner cells. In one aspect, a fusion partner cell expresses hTERT and gp130 ΔYY. In another aspect, a fusion partner cell expresses hTERT, the Anchor, and gp130 ΔYY.

III. METHODS

Any or all of these nucleic acid molecules, vectors and cell types described above can be used in any number of methods for the analysis and/or generation or production of selected secreted target proteins, for the generation and/or identification of cells with desirable characteristics, e.g., high target protein producers, as well as for the high throughput screening and evaluation of hybridomas. Diverse methods for introducing nucleic acids into cells under conditions that result in the stable or transient expression of genes encoded by those nucleic acids are in common use and well known to those skilled in the art. The compositions described herein can be employed in the following methods, as well as in other similar methods.

In one aspect, a method for generating a cell expressing an Anchor as described herein involves stably or transiently delivering to a selected cell (mammalian, non-mammalian, primary or immortalized) a nucleic acid molecule or vector expressing the Anchor. For example, ectopic expression of the Anchor protein in an immortal cell line may be achieved through transduction of the cells with the replication-defective retroviruses or lentiviruses that contain a nucleic acid sequence that encodes the Anchor protein. Examples of methods and plasmid vectors and methods that can be used to create useful replication-defective retroviruses or lentiviruses include pMSCV and pLION II vectors and plasmids are described.[12,13,14]

In certain embodiments, retroviral or lentiviral particles created using these methods infect cells and provide them with a nucleic acid sequence capable of expressing an Anchor protein in the recipient cell. The transgene encoding the Anchor is operationally linked to nucleic acid sequences that enable stable or inducible expression in the recipient cells. Alternative methods of introducing a nucleic acid containing Anchor-encoding sequences and necessary regulatory elements are also well-known to practitioners of the art, and include calcium phosphate transfection, electroporation, and cationic lipid-mediated transfection.

Ectopic expression of the Anchor is confirmed using a variety of methods. In one embodiment, the Anchor contains murine scFv domains, which are bound by anti-sera specific for murine Ig, which is labeled with a fluorescent moiety. Contacting a population of cells that contain nucleic acid sequences that encode the Anchor protein with such an antiserum, if the cell expresses the Anchor protein, causes the fluorescent antiserum to bind to the surface of the cell. By this means, cells that express the Anchor protein are identified on the basis of their fluorescent signaling through microscopy, flow cytometry, or other methods. In other embodiments, additional antigens are incorporated into the Anchor protein, which is bound by molecules that are used to assess Anchor expression. In one embodiment, where the Anchor protein has a Myc tag, an antibody specific for the Myc tag is used to assess Anchor expression. The use and detection of other polypeptide tags, such as the FLAG Tag, NE Tag, HA-Tag, or a His Tag or poly-His tag, which are fused to proteins of interest in order to enable confirmation of protein expression through the use of antibodies that bind the tags, is well known in the art.

The method permits the creation of a variety of such cells as components useful for further modification to create hybridoma cell lines or other stable cell lines that express and secrete recombinant proteins. These methods have broad utility for assessing characteristics of the cells and the proteins that they secrete, including quantitative, structural, functional, antigenic, catalytic, and interactive characteristics.

As constituted, cells that secrete antibodies or other proteins, whether autochthonous or recombinantly expressed, in combination with the Anchor protein, possess the capability that the secreted protein can be inducibly adhered to the surface of the cell by contacting the cell with a suitable Linker protein. The general utility of this type of cell, compared to cells that do not express the Anchor Protein, is that the secreted protein can be analyzed while physically linked to the cell that expresses it. This is especially useful when one is analyzing secreted proteins that are expressed by a heterogeneous population of cells, in which the cells secrete different molecules, and the object is to identify and/or isolate individual members of the cell population that secrete molecules with specific characteristics.

In one embodiment, a cell population secreting a polyclonal population of mAbs and expressing the Anchor protein is contacted with a Linker molecule specific for the mAb, in suitable culture conditions, in which the secreted mAb adheres to the cell. This cell population is optionally contacted with a fluorescent-labeled antigen. Cells that secrete a mAb specific for the antigen are readily identified on the basis of the fluorescent signal adhered to their membranes. By this means, a hybridoma secreting a mAb with desirable antigen binding specificity, and residing among a polyclonal population of hybridomas from which it could not otherwise be readily distinguished, is readily be identified and isolated.

Another application for the cell expressing the Anchor protein is to facilitate the analysis of a diverse population of cells that all secrete the same molecule, but at different rates. In this embodiment, the object is to identify and/or isolate individual members of the cell population that secrete molecules at a specific rate. In one such embodiment, a cell population secreting a cytokine or mAb, and expressing the Anchor protein is contacted with a Linker molecule specific for the cytokine or the mAb, in suitable culture conditions, in which the secreted protein adheres to the cell in proportion to its rate of production. By this means, a high-expressing member of the population is identified and isolated.

Where the original cell is not immortalized, another embodiment of this method includes immortalizing the cell now carrying the nucleic molecule or vector by conventional methods. Thus, this method can be adapted to create a desirable immortalized cell that expresses the Anchor for the purposes of immobilizing a secreted target protein. Such an immortalized cell can be a fusion partner cell for generation of hybridomas, as described in the examples below.

In certain embodiments of the methods and compositions described herein, the Anchor is introduced into a cell at any time before or after the initiation of secretion of a molecule by that cell. For example, the Anchor protein is expressed on an immortalized cell that does not secrete a particular protein, such as a CHO or 293T cell, which cells are commonly used for the industrial production of proteins and other biologic molecules. Following the establishment of Anchor protein expression on those cells, an additional nucleic acid is provided to a population of those cells that would induce the secretion of a Target, such as an immunoglobulin or a cytokine, by those cells. The amount of Target secreted by those cells is assessed by contacting the population of cells with a Linker specific for the secreted Target, and cells specifically secreting the desirable quantity of the Target are identified. This method, in one example of industrial utility, can rapidly and efficiently identify the cell among the population that secretes the largest amount of a commercially valuable protein.

In still another embodiment, the Anchor is introduced into a cell intended to be fused to another cell to create a hybrid cell (or hybridoma). Such a cell is called a fusion partner cell. Following the establishment of Anchor protein expression on the fusion partner cells, the cells could be fused to another cell population, comprised of cells that secrete diverse isoforms of a desired Target protein. This embodiment of the methods creates a polyclonal population of cells that express both the Anchor protein and diverse isoforms of the desired Target protein. Hybridomas secreting the ideal isoform of the desirable protein are readily identified and isolated using the methods provided by this invention.

Thus, in another aspect, a method of making a hybridoma cell comprises fusing a B lineage cell with such a fusion partner cell, e.g., an immortalized cell having expressed on its outer plasma membrane surface an Anchor designed to form a complex with a selected Linker; the Linker designed to bind the antibody secreted by the B cell or a cell derived from a B cell, which antibody (e.g., monoclonal antibody) is not recognized by the Anchor.

In additional to the methods of making the cell lines, there are a variety of different methods in which the resulting cells can be used. As one example, a method for detecting or measuring a characteristic of a target protein secreted by a cell can employ the novel cells which express the Anchor. In one such method a population of cells is provided, each cell of the population having expressed on its outer plasma membrane surface an Anchor designed to form a first complex with a Linker. That population of cells is then contacted with the Linker designed to form the first complex and to form a second complex with a target protein that is not recognized by the Anchor. Exposure of the population of cells to the Linker permits the Linker to adhere to the outer plasma membrane of the cells by binding in the first complex with the Anchor. This resulting population of cells is maintained in the presence of the Linker under conditions in which the cells secrete the target protein. The target protein binds to the cell-adhered first complex via formation of the second complex, i.e., the bound Linker-Target Protein complex. Thus, the Target Protein is bound to the cell which secreted it. In certain embodiments, the bound Target Protein is then subjected to a variety of assays directed to identifying the existence, antigen specificity, antigen binding affinity, titer, amount, or biological activity of the target protein bound onto the cell by the first and second immune complexes.

In this method, the requirements specified above for the generation of the components and cells apply. That is, the Linker is of a species heterologous to the species of the Anchor; and the target protein is of a species heterologous to the Linker and to the Anchor. In certain embodiments, the use of heterologous species Anchors, Linkers and Target Proteins is essential to the methods and compositions herein described. In one embodiment, the compositions and methods are reduced to practice with an Anchor molecule that is of murine origin and is able to specifically bind an Ig Linker of rabbit origin. In this case, the rabbit Ig Linker is, e.g., a rabbit mAb or Fab specific for the secreted Target protein.

Therefore, specific embodiments of the present invention can be expressed more specifically as: (1) The Anchor protein has the following characteristics: minimal affinity for the secreted protein and binds an Ig Linker protein. (2) The Ig Linker protein has the following characteristics: It binds to the Anchor protein and to the secreted Target protein.

The Linker or Ig Linker has a role that can be fulfilled in many configurations, considering that the key attribute of the Linker is that it has affinity for two distinct moieties under conditions in which neither of the two moieties would associate, and that, when in the presence of the two moieties, the Ig linker creates an immune complex incorporating the two moieties into one molecular complex. In certain embodiments, the Anchor protein binds the Fc or Fab domain of the Ig Linker protein, through canonical binding (i.e., in which the antigen binding site of the Anchor protein scFv domains recognize specific antigens on the Ig Linker), or non-canonical binding. In certain embodiments, the antigen recognized on the secreted mAb is the same as an antigen expressed by the scFv on the surface of the cell. In this case, an Ig-Linker specific for one binding site on the secreted Target protein and another binding site on an Anchor protein links the secreted protein to the Anchor on the secreting cell. For example, a hybridoma expressing the Anchor molecule of the present embodiment and secreting a murine Ig, when contacted with an Ig-Linker consisting of a rabbit polyclonal anti-murine Ig antiserum, adheres the secreted murine Ig to the cell surface. In this embodiment, the essential feature of the Anchor is not that it binds an Ig of a heterologous species. Rather, it is a molecule that does not bind to the secreted molecule but can be bound by the Ig-linker. It is clear from this description that the Anchor can be highly similar or different from the molecule secreted by the cell.

It further is clear that the Anchor molecule can function equivalently in the present invention whether it is a molecule that binds other molecules (e.g. possesses an antigen-binding domain derived from an immunoglobulin) or if it is simply a protein that can be specifically bound by a functional Linker. In the present invention, the Anchor contains a MYC tag, which itself could be recognized by an Ig-Linker that recognizes a MYC tag. If a cell expressing the Anchor secretes a recombinant protein that also possessed a MYC tag, then a suitable Ig-linker is a polyclonal anti-MYC tag antiserum, which is commercially available. Any of the tags described herein are useful for this purpose, e.g. a FLAG Tag, NE Tag, HA-Tag, or a His Tag or poly-His tag. In other embodiments, it is clear that any molecule could be used as a tag.

Still another aspect of the methods described herein is a method for the rapid and efficient creation of recombinant cell lines expressing optimally large amounts of a commercially valuable protein. In the production of recombinant proteins in cell-based systems, it is common to incorporate a polypeptide tag into the sequence of the molecule in order to facilitate isolation of the produced protein. In one embodiment of the present invention, a 293T cell line is created that expresses the Anchor protein (293T-Anchor). The 293T Anchor cells are provided by calcium phosphate transfection with a nucleic acid that encodes a secretory protein containing a MYC tag, thereby creating a population of cells secreting diverse levels of the MYC-tagged protein. Contacting this cell population with a polyclonal anti-MYC Ig-Linker adheres the secreted protein to the cells by creating molecular complexes that join the MYC tag on the secreted protein to the MYC tag on the Anchor protein.

Measurement of the amount of secreted protein that is adhered to the surface of the expressing cells by this method allows direct measurement of the amount of protein secreted by each cell individually. In certain embodiment, this method is useful to identify the cell rapidly and efficiently among the population that secretes the largest amount of a commercially valuable protein.

In methods of the present invention in which proteins secreted by cell populations that express the Anchor protein are assessed, it is advantageous to be able to maintain the polyclonal cell populations in a single vessel, for example, containing tens or thousands or more of individual clones. In order to ensure that secreting cells maintained in the presence of the Linker preferentially bind to the molecules that they themselves secreted and bind relatively less to molecules that they did not secrete; the method can be modified to include the following step. The contacting step can involve contacting the cells with an excess concentration of the Linker. The excess increases the specificity of the binding between the first complex on the cell surface and the target protein secreted by the cell, relative to the binding of the target protein to other cells in the population that do not secrete it. Under these conditions the Anchor molecules are mostly or completely bound to Linker proteins. If a secreted molecule is not captured by a Linker adherent to the cell that secretes it, it is bound to a soluble Linker protein that only binds to a non-secreting cell if (1) the cell produced a new, un-bound Anchor molecule or (2) if it replaced a Linker molecule already bound to a cell. This improves the accuracy of the results obtained by the assays directed to identifying the existence, antigen specificity, antigen binding affinity, titer, amount, or biological activity of the target protein. Furthermore, it is advantageous because these method steps simplify the analysis of individual members within large cell populations by mitigating the need to analyze cells as isolated clones or oligoclonal populations. This method is particularly suitable when most or all of the cells within a population are secreting Target proteins.

Still another modification of the basic method is useful when some of the cells within a population are not secreting any Target protein, and therefore have binding sites available to bind Target proteins secreted by other cells. This embodiment of the method involves contacting the cells with the Ig-Linker in combination with a competitor protein of the same species or type as the secreted target protein. In this embodiment, secreted molecules that do not adhere to the cells that produced them enter the cell culture medium and complex with Linker protein. They join a pool of Linker molecules in which some of the Linker molecules are bound to a protein similar to the secreted molecule but can readily be distinguished from the secreted molecule by the assay being performed. In this variation of the method, the competitor protein has a distinct structure, activity, or antigen binding specificity.

In one embodiment, the Target Protein is a human monoclonal antibody specific for a specific human antigen; the competitor protein is a human antibody that binds a different antigen; and the antibodies bound to the cells are assayed for their ability to bind the specific human antigen. In another embodiment, the Target Protein is an Ig molecule, the Linker binds the Fc domain of the Ig molecule; the competitor is an Ig Fc domain, and the assay detects the presence of the Ig FAb domain contained in the Target Protein. This embodiment illustrates a general process whereby the quantities of a Target Protein secreted by individual cells is assessed within a polyclonal population in which some of the cells express the Target Protein and some of the cells do not. This particular embodiment is specifically suitable for measuring the amounts of Ig secreted by a population of hybridomas or recombinant cells; but it can be readily adapted for the detection of any secreted Target Protein, through the selection of suitable Ig-Linker proteins and Target-like competitor molecules. The converse embodiment is suitable for this purpose as well: the Linker binds an Ig FAb domain; the competitor is an Ig FAb domain; and the assay detects the presence of the Fc domain of the Target Protein. In these embodiments, the presence of the competitor protein increases the specificity of the binding between the first complex on the cell surface and the Target Protein secreted by the cell, relative to the binding of a Target Protein to a cell that did not secrete it. The competitor protein does so, by occupying Target Protein binding sites (i.e. Linker molecules) on the non-secretor cells that would otherwise be available to bind Target Protein molecules. This "competition" limits the amount of Target Protein bound by binding sites on Linker molecules bound to Anchor molecules on non-secreting cells.

Another modification of the methods described herein, includes contacting the cells which have been previously or concurrently exposed to Linker and Target Protein with a detectably labelled antigen to which the Target Protein specifically binds in a third complex binding reaction. Thus, cells having on their outer membrane surface the multi-part complex comprising the Anchor bound to the Linker bound to the Target Protein contact the antigen and bind it to the cell via its immune complex with the Target Protein. The presence of the labeled antigen on the cell in this bound multi-part complex permits rapid identification of cells that secrete Target Protein that binds the antigen by identifying or quantifying the detectable label associated with cell-bound multi-part complex.

The antigen for use in this modification of the methods is selected from antigen(s) to which the Target Protein, e.g., antibody or antibody fragment, naturally binds. In one embodiment, where the Target Protein is a monoclonal antibody, the antigen selected for labeling is a single antigen. Where the Target Protein is an antibody capable of binding multiple antigens or a rare epitope shared by multiple homologous molecules, a number of antigens to which that Target Protein binds can be labeled for this use.

Yet another method employing the cells described herein is a method of identifying a hybridoma cell that secretes a monoclonal antibody that has a pre-selected characteristic, said cell residing among a population of cells that do not secrete a monoclonal antibody with said characteristic. In this method a population of hybridoma cells is prepared by fusing B lineage cells with immortalized cells having expressed on their outer plasma membrane surface an Anchor designed to form a first complex with a selected Linker as described herein. This population of cells is contacted with the Linker designed to participate in two binding events to form a multi-part complex, i.e., the Linkers forms the first complex with the Anchor and a second complex with a single monoclonal antibody secreted by a single hybridoma cell in the population. The monoclonal antibody can be a species heterologous to that of the Linker. The monoclonal antibody is not recognized by the Anchor. The contacting of the Linker with the population of cells permits the Linker to adhere to the outer plasma membrane of the hybridoma cells by binding in the first complex with the Anchor. These cells are maintained in the presence of the Linker under conditions in which hybridoma cell secretes its monoclonal antibody. When the mAb is secreted, the Linker bound to the Anchor forms a second complex with the monoclonal antibody secreted by a hybridoma cell. In this manner, the monoclonal antibody binds to the hybridoma cell that secretes it via the adhered immune complex. The presence of a population of hybridoma cells having adhered thereon their secreted mAbs permits the identification of the existence, antigen specificity, antigen binding affinity, titer, amount, or biological activity of that monoclonal antibody. This method also permits the identification of hybridoma cells that produce a particular mAb having desirable characteristics, such as expressing and secreting the cells more highly than other cells in the population. Therefore, an optional step of this method includes isolating the hybridoma cells at any time after the cells are contacted with the Linker.

In yet a further embodiment of this method, the population of cells is contacted with an excess concentration of the Ig Linker. The excess Ig Linker increases the specificity of the binding between the first immune complex on the cell surface and the monoclonal antibody secreted by its hybridoma cell, relative to the binding of the monoclonal antibody to other cells that do not secrete it. In various embodiments, the Ig Linker has different levels of binding valency. For example, an Ig Linker is a monomeric scFv, camelid antibody, or single domain Fab. In this case, every Ig Linker binds only one Target Protein. In other embodiments, if the Ig Linker is a conventional IgG (with two antigen binding sites), or a polyclonal anti-serum specific for the Target Protein, then, in the presence of excess Ig Linker, multimeric complexes form on the surface of the cell that comprise a concatenation of multiple Ig Linker molecules binding to Target molecules, which can themselves recruit more Ig Linker molecules from the culture medium, and these molecules in turn can bind more Target molecules. It is evident that such complexes are stabilized by avidity effects.

Furthermore, the assembly of concatenated Ig molecules creates complexes that can be assessed for biological effects that result from the presence of multiple immunoglobulin molecules in an immune complex. For example, it is well known that mAbs that bind to stimulatory molecules on T cells frequently depend on cross-linking or surface immobilization for their optimal stimulatory activities.[15, 16] In addition, IgG immune complexes activate the classical complement system, which can have potent anti-microbial, anti-viral, pro-inflammatory, and anti-neoplastic effects.[17, 18]

Immune complexes assembled on the surface of hybridoma cells through the reagents and methods described herein are, in other embodiments, assessed for their ability to exert effects limited to those immune complexes. This is advantageous compared to existing methods for assessing the immune-complex-dependent activities of mAbs expressed by hybridomas of the prior art.

In another modification of this method, the cells are contacted with a competitor antibody of the same species or type as the secreted monoclonal antibody. The competitor antibody has a different or non-specific antigen binding specificity. The presence of the competitor antibody increases the specificity of the binding between the first complex on the cell surface and the monoclonal antibody secreted by the cell, relative to the binding of that monoclonal antibody to a cell that does not secrete it, by binding excess unbound Linker.

Yet another modification is akin to that described above for the more general method. The population of hybridoma cells is further contacted with a detectably labelled antigen to which the monoclonal antibody specifically binds in another immune complex binding. By providing labeled antigen to which the secreted mAb specifically binds, a labeled multi-immune complex is formed on the outer surface membrane of the hybridoma secreting a desired mAb. The multi-immune complex is formed by the first immune complex Anchor-Linker, with the Linker also bound to the secreted monoclonal antibody, which is also bound to the labeled antigen. After these labeled cells are provided, hybridoma cells that secrete monoclonal antibody specific for a selected antigen are rapidly identified by detecting and/or quantifying the detectable label associated with cell-bound multi-part complex.

In certain specific embodiments of this method, and as illustrated in the examples below, the monoclonal antibody is a human antibody; the Anchor comprises an scFv of one species (e.g., murine); the Ig Linker is an anti-human-Ig antibody that is neither human nor murine (e.g., an anti-human rabbit antibody) or an antibody binding fragment of the human antibody.

Various modifications of these methods can be made based on the selection of the components of the nucleic acid molecule, vectors, cells and method components, such modifications are believed to be within the skill of the art given the teachings of this specification. Such variations provide for other optional modifications of these methods.

In one modification of the methods of generating and identifying the characteristics of hybridomas and their secreted antibodies, the Linker specifically binds the Fc portion of the Target Protein, i.e., monoclonal antibody. Thus another optional step of the method involves contacting the hybridoma cells which have been exposed to the Linker and secreted Target Protein with an IgG Fc domain competitor of the same species as that of the Target monoclonal antibody. Also added to the contacting reaction is a detectably labeled antibody specific for the Ig Fab domain of the same mammalian species as that of the Target monoclonal antibody. The various elements of the contact mixture form immune complexes, i.e., Anchor with Linker, bound or free Linker with Target mAb, bound or free Target mAb with IgG Fc domain competitor and bound or free Target mAb with detectably labeled antibody. Some of the Target monoclonal antibody secreted by the hybridoma cell is bound to the cell in an immune complex with the Anchor-Linker, while some of the Target mAb is bound in the medium by excess unbound Linker. The Ig Fc domains compete to reduce binding of intact Target mAb to hybridoma cells that do not secrete Target mAb; and the anti-Ig FAb antibody binds to the secreted Target mAb bound to the cell surface. Unbound complexes are separated from cells with bound multi-immune complexes, and the labeled antibody used to identify hybridoma cells and their bound Target mAbs and permit the analysis and quantification thereof.

In a similar manner, the methods are modified in the following manner. The Linker is selected that specifically binds the FAb portion of the Target monoclonal antibody. The hybridoma cells which have been exposed to the Linker and secreted Target mAb are also exposed to an Ig FAb domain competitor of the same species of the Target mAb, and a detectably labeled antibody specific for the Fc domain of the same mammalian species of the Target mAb. Target monoclonal antibody secreted by the hybridoma cell is bound to the cell in an immune complex with the Anchor-Linker and is bound in the medium by excess Linker. The Ig FAb domains compete to reduce binding of intact Target mAb to hybridoma cells that do not secrete monoclonal antibody. Labeled anti-Ig FAb antibody binds to the secreted Target mAb bound to the cell surface. Unbound complexes are separated from cells with bound multi-immune complexes, and the labeled antibody used to identify hybridoma cells and their bound Target mAbs and permit the analysis and quantification thereof.

Yet another method that uses these described components is a method for producing a selected recombinant target protein. In such a method, a cell as described above is generated to express a suitable Anchor under the control of an inducible or repressible promoter and associated regulatory sequences. However, the cell is not a hybridoma but is a cell that has been modified by genetic engineering methodologies to express and secrete any desired Target Protein, e.g., a desirable therapeutic protein. The selection of a suitable expression cassette with regulatory sequences to express and secrete the Target Protein are well known and a suitable gene cassette with appropriate sequences and a selected recombinant transgene can be inserted by electroporation, infection by viral vectors or transfection by plasmid into a cell which has been generated to express the Anchor. The manipulation of the cell to express the Target Protein and the described manipulations of the cell to express an Anchor may occur in any order. The cell is cultured to enable expression of the Target Protein and its secretion from the mammalian cell. The cell is also concurrently or sequentially contacted with a compound that induces or turns on expression of the Anchor. This method then involves contacting the cells with the designed Ig-Linker, wherein the Ig-Linker binds to the Anchor on the cell and to the expressed recombinant Target Protein, and permits the Target Protein to adhere to the surface of the cell via the Anchor-Ig Linker immune complex. The inducing compound is then withdrawn. In this method, cells that express high quantities of Target Protein can be identified, isolated and analyzed based upon quantitative detection of the immune complex. The use of the inducing compound permits the Anchor to be transiently or controllably expressed.

In a further modification of this method, the cells are contacted with an excess concentration of the Linker. The excess Linker increases the specificity of the binding between the Anchor-Linker complex on the cell surface and the Target Protein secreted by the cell, relative to the binding of the Target Protein to other cells that do not secrete it. In a manner similar to other methods described above, the cells can also be contacted with a competitor protein of the same species or type as the secreted Target protein. The competitor protein is of the same species or type as the Target Protein. The presence of the competitor protein increases the specificity of the binding between the first immune complex on the cell surface and the Target Protein secreted by the cell, by binding excess unbound Linker.

In another aspect, a method for maintaining a hybridoma mAb expression library described herein, comprises the steps of:

(a) contacting
 (i) a population of hybridoma cells, prepared by fusing B lineage cells with immortalized cells having expressed on their outer plasma membrane surface an Anchor designed to form a first complex with a selected Linker; with
 (ii) the Linker designed to form the first complex with the Anchor and a second complex with a single monoclonal antibody secreted by a single hybridoma cell, wherein the monoclonal antibody is not recognized by the Anchor; the contacting permitting the Linker to adhere to the outer plasma membrane of the hybridoma cells by binding in the first complex with the Anchor;

(b) maintaining the cells of (a) in the presence of the Linker under conditions in which the Linker forms a second complex with the monoclonal antibody secreted by a hybridoma cell and the monoclonal antibody binds to the hybridoma cell that secretes it via the adhered first and second complexes; and (c) identifying the existence, antigen specificity, antigen binding affinity, titer, amount, or biological activity of the monoclonal antibody secreted by the hybridoma cells and bound thereto by the cell bound multiple immune complex formed by Anchor-Linker-monoclonal antibody;

(d) isolating the population of hybridoma cells that secrete monoclonal antibody with a desired antigen specificity, antigen binding affinity, titer, amount, or biological activity; and (e) culturing the population resulting from (d) above.

In another aspect, a method for maintaining the hybridoma mAb expression library described herein wherein the characteristic of the cells and isolated and isolated is the amount, quantity, or rate of expression of the monoclonal antibodies expressed by the hybridoma cells.

Another method for monitoring and optimizing ectopic cytokine signaling activity in a population of the above-described fusion partner cells or an oligoclonal population of hybridomas derived therefrom, comprises the steps of, (a) contacting the cells with a detectable monoclonal antibody specific for the gp130 ΔYY Receptor molecule;

(b) isolating the cells bound to the detectable monoclonal antibody; and (c) culturing the cells resulting from (b) above.

In one aspect, the On-Cell mAb Screening (OCMS™) method for human anti-viral mAb discovery involves generating cells to produce a BGS scaffold as described above, and that can specifically adhere their secreted mAbs to the surfaces of the cells that produce the mAbs. If the cells (e.g., hybridoma cells generated from B cells of a patient that has recovered from a viral infection of known or unknown origin) produce anti-viral antigen-specific mAbs, they can be readily identified and screened by this method.

Thus as another embodiment, is a universal assay for anti-viral mAb discovery is provided. Currently to identify a mAb that binds to a viral surface antigen, tests need to be performed in which a panel of mAbs are tested for binding to the viral antigen. For this purpose, viral antigens must be incorporated into mAb binding assays, such as ELISA, flow cytometry, or High Content Imaging. Per the current state of the art, each of these assay formats is specific for the antigen (or antigens) to be tested and can include recombinant viral antigen molecules or purified virions, fluorescent labels, biotin, epitope tags, and/or capture or secondary antibodies specific for the viral antigens. Therefore, the process of preparing a viral antigen test for mAb cloning is complex and can be an important barrier to success in obtaining anti-viral mAbs. The universal anti-viral mAb binding test provided by the present invention allows mAbs to be obtained without the need to create a specific binding assay for each viral antigen.

The cells of the current invention enable screening for mAbs using common reagents for different viral antigens, i.e. universal assay for anti-viral mAb discovery. A population of BGS/OCMS cell lines or hybridoma are generated, on which the Anchor/Linker binds the secreted mAb (or secreted protein) to the cell surface. When multivalent viral antigens (such as purified viral antigens, virions or Virus-like Particles (VLPs)) are added to cells displaying these complexes, the viral antigen is thereafter bound to a mAb on the surface of a hybridoma. Additional mAbs secreted by that cell will coat the virus particle. The position and arrangement of these additional mAbs on the hybridoma cell surface is different than for mAbs that are bound closely to the cell through the Linker molecules. As a result, the presence of viral antigens bound to the surface of a hybridoma cell can be inferred by observing the arrangement of human mAbs relative to the hybridoma plasma membrane. The differences in mAb localization on the hybridoma surface in the presence or absence of a viral antigen can be amplified by using a monovalent Linker protein, such as a FAb. As described in Example 16 below, the OCMS method was used to create a universal assay using high-throughput screening using High-Content Imaging (essentially, confocal microscopy accompanied by powerful image analysis software). See FIG. 20.

If the mAb bound to the cell surface via the BGS is an anti-viral mAb, the mAb will capture the virus or viral antigen, forming a detectable CAP-like immune complex. If the secreted mAb is not antiviral, it will not bind to the viral antigen, and no complex will be formed. In another embodiment, if the viral antigen is multivalent, it will further form a large complex by binding with the bound mAb and also binding or cross-linking with other Ig produced by the cell or added human IgG reagents that do not bind to the cell, forming an even larger CAP-like immune complex adhered to the cell. Alternatively, where the whole virus is used, and as viruses are larger than antibodies, e.g., on the order of about 30 nm or more, an even larger complex will be produced adhering to the cell. Thus, when hybridomas expressing anti-viral mAbs come into contact with the virus, tell-tale immune complexes form on the surface of the hybridomas. This OCMS method enables identification of the cells secreting the anti-viral antibody by imaging the shape and size of the immune complex formed on the cell. Thus detection of CAP-like or LAYERED immune complexes formed on the cell surface allows the relevant useful anti-viral mAb to be identified and obtained without gene cloning and expression. In another embodiment, the OCMS method may be modified by engineering cells for use in screening mAbs for viral neutralization, in addition to virus binding.

In another embodiment, of the OCMS method, mAb structure and function are optimized through Directed Evolution (creating a diversified population of mAbs and selecting the one with the desired characteristics)[38]. The human mAbs isolated from patients who have survived a viral illness are likely to be useful as therapeutics, but they may not be ideal with regards to mAb stability, expression levels, binding kinetics, or binding specificity. Expression of Activation-Induced Cytidine Deaminase (AID) in a cell activates natural mechanisms of antibody diversification through somatic hypermutation[39]. Using a Directed Evolution system for human mAbs, AID is transiently activated in hybridomas and the resultant populations are screened for variants with improved binding activities. These experiments are not practical with conventional hybridoma methods, but are uniquely enabled by the high throughput capabilities of OCMS.

It is anticipated that these methods have great value for rapid evaluation and diagnosis and treatment of a viral epidemic, even of an unknown virus. By being able to use intact virions in the OCMS method, one would perform the method, monitor for detection of tell-tale immune complexes and select the cells that express the anti-viral antibody without first knowing the identity of the virus. One would directly go to cloning of the antibody without further analysis to create a therapeutic composition.

In yet another embodiment, similar strategies can be performed with cells other than hybridoma cells. By making a BGS-expressing cell and transiently transfecting such a cell with recombinant human heavy chain sequence and light chain sequence, one may rapidly identify those cells expressing antibody. Briefly, the BGS-expressing cell that also expressed human IgG contacts rabbit anti-human IgG and a fluorescently labeled secondary antibody specific for human IgG. After this contact, the expressed human IgG is captured on the cell surface by the RAH and labelled with fluorescence secondary antibody. In only a few hours, such an assay enables identification of the cells expressing the recombinantly expressed antibody or antibody (antigen-binding) fragment, by identifying its binding onto the cell surface, and allows such antibody or fragments to be separated from cells that express little or no IgG. See Example 14.

It is anticipated that other modifications of these methods and compositions can be designed by use of the teachings provided herein combined with knowledge in the art. Such modifications are encompassed by this invention.

IV. EMBODIMENTS

Given the number of variations that one can generate in the constructs using the teachings provided herein, many other methods employing these compositions can be used for rapid and complex target identification or other uses. For example, the compositions and methods may be used in methods for tracking any molecular (e.g., protein) secreted by a cell, e.g., for quality control. In another embodiment, a monoclonal antibody bound to its hybridoma cell can be assessed for bind to its antigen or activities it may only express when incorporated into an immune complex, such as T cell activation.

These compositions and methods can be used for bulk culture and screening of diverse hybridomas secreting mAbs for identification and isolation of mAbs with selected desired features. In this embodiment, the compositions and methods described herein create a system to facilitate high throughput screening of antibodies secreted by hybridoma cells.

In another embodiment, a cell-Anchor-Linker (e.g., Ig Linker)-Target (e.g., mAb) complex enables rapid screening of populations of cells (e.g., mammalian cells, insect cells, or yeast cells) that produce diverse molecules (e.g., polypeptides) which may be recognized and bound by a Target. Even more simply these methods provide a simple means of creating immune complexes that can be assessed for immune-complex mediated functions.

As described in the examples below, an exemplary fusion partner cell line LCX BGS is generated by the teachings of this specification. LCX BGS is fused with B-lymphocytes to generate hybridomas that secrete human mAbs and express the Anchor. Two exemplary hybridoma cell lines generated by the methods described herein are referred to as hybridoma 8C5 BGS and hybridoma 9H2 BGS.

V. EXAMPLES

The following examples provide evidence of the generation of mammalian cells that capture target molecules secreted by those cells on their outer plasma membrane when contacted by a linker molecule. Also disclosed are certain fusion partner cells and hybridomas according to these teachings. The following examples disclose specific embodiments of the methods and compositions described herein. These examples should be construed to encompass any and all variations that become evident as a result of the teaching provided herein.

Example 1: Generation of Nucleic Acid Molecule Encoding an Anchor

A nucleic acid molecule encoding an Anchor is constructed using the following elements in the table below. Briefly, a nucleic acid sequence encoding a variable domain of murine anti-rabbit antibody heavy chain ($V_H$) was linked to a variable domain of the antibody light chain ($V_L$) via a spacer encoding $(Gly_4Ser)_3$, resulting in a sequence encoding single chain variable fragment (scFv). Further, two nucleic acid sequences encoding scFv were linked together by a spacer described above and resulted in a tandem scFv coding sequence. Additional sequences in the nucleic acid molecule included a sequence encoding an N-terminal leader sequence (AKA, a signal peptide) from a kappa light chain immunoglobulin protein to ensure the expression of scFv on the cell surface. The sequence is provided in the NCBI database under NCBI Reference Sequence: XP_003753129.1 (Ig kappa chain V-III region MOPC 63 isoform X2; species *Rattus norvegicus*). Additional sequences in the nucleic acid molecule or construct are a sequence encoding an epitope tag or protease tag sequence (i.e., c-Myc), and a platelet-derived growth factor receptor (PDGF receptor, PDGFR) transmembrane (TM) domain. The nucleic acid molecule/construct was further optimized for murine cell expression having 1781 nucleotides with a 58.92% of cytosine and guanine. The sequence of the nucleic acid molecule/construct encoding an embodiment of an Anchor is provided as SEQ ID NO: 1. The corresponding protein sequence is SEQ ID NO: 2. The nucleic acid molecule was ligated into the retroviral transfer plasmid pMSCV and into the lentiviral transfer plasmid pLION II according to described protocols. 13,14,15

TABLE 1

Elements of SEQ ID NO: 1.

| Nucleotides of SEQ ID NO: 1 | Element | Total Base Prs | Total Amino Acids | Amino Acids of SEQ ID NO: 2 |
|---|---|---|---|---|
| 1-12 | 5' restriction domain | 12 | n/a | n/a |
| 13-75 | Kappa Ig leader | 63 | 21 | 1-21 |
| 76-432 | scFv heavy chain | 357 | 119 | 22-140 |
| 433-477 | $(Gly_4Ser)_3$ spacer | 45 | 15 | 141-155 |
| 478-807 | scFv light chain | 330 | 110 | 156-265 |
| 808-852 | $(Gly_4Ser)_3$ spacer | 45 | 15 | 266-280 |
| 853-1209 | scFv heavy chain | 357 | 119 | 281-399 |
| 1210-1254 | $(Gly_4Ser)_3$ spacer | 45 | 15 | 400-414 |
| 1255-1584 | scFv light chain | 330 | 110 | 415-524 |
| 1585-1614 | c-myc tag | 30 | 10 | 525-534 |
| 1615-1764 | PDGF receptor TM domain | 150 | 50 | 535-584 |
| 1765-1767 | Stop codon | 3 | n/a | n/a |
| 1768-1781 | 3' restriction domain | 14 | n/a | n/a |

Example 2: Establishment of the LCX Fusion Partner Cell Line

Figure 14:
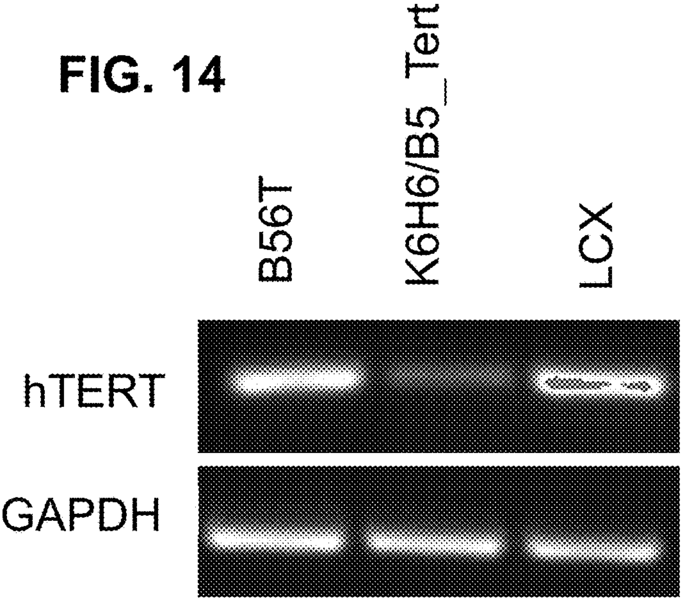
FIG. 14 is a RT-PCR gel result showing that LCX cells express hTERT.

Signaling from ectopic expression of IL-6 is critical for stable secretion of human immunoglobulins by hybridomas that also express hTERT. Optimization and standardization of hybridoma protocols therefore require that IL-6-stimulatory activity of individual cells in a bulk cell population be efficiently assessable in real time. Yet, the secretion rates of IL-6 by individual cells in a polyclonal population is difficult to measure. The LCX cell line was created to express ectopic hTERT and to provide IL-6 signaling activity which can be monitored by assessing surface expression of a molecule that transduces an IL-6-like signal. Parental K6H6/B5 cells were modified to express hTERT in addition to the gp130 ΔYY protein (a constitutively active member of the IL-6 receptor family) by retroviral transduction and RT-PCR was performed to confirm the expression of the ectopic hTERT gene in LCX cells (see FIG. 14) as described.[13]

Conventional immunofluorescent staining for detecting cell-surface antigen using flow cytometry was performed to confirm the expression of gp130 as described.[19]

Figure 15:
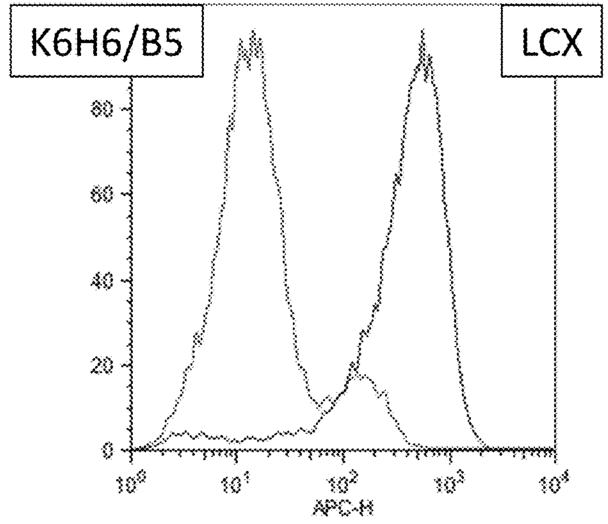
FIG. 15 is a graph of flow cytometry demonstrating surface expression of the constitutively active gp130 ΔYY mutant protein by LCX cells as described in Example 2.
Figure 16:
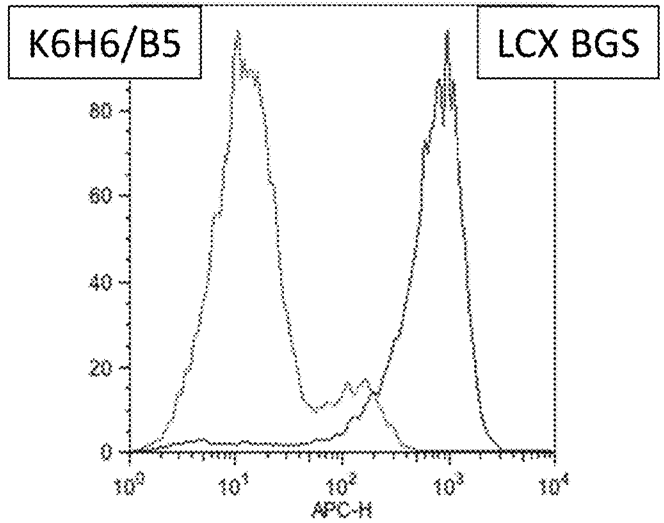
FIG. 16 is a graph of flow cytometry demonstrating surface expression of the constitutively active gp130 ΔYY mutant protein by LCX BGS cells, which express the tandem murine scFv (BGS).
Figures 17A, 17B, 17C, 17D:
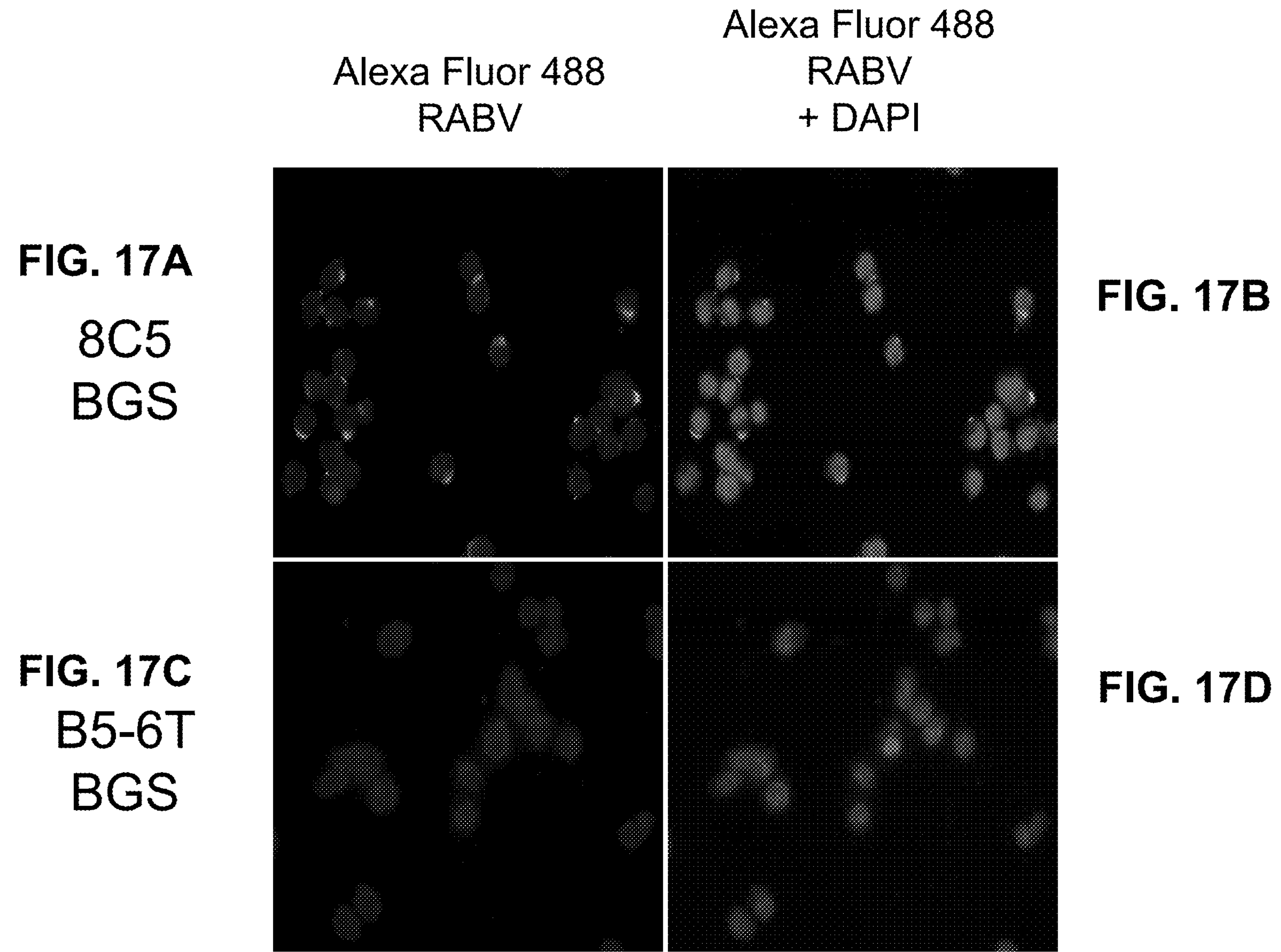
FIGS. 17A through 17D are fluorescence photomicrographs of two examples of hybridoma cells lines: the 8C5 BGS hybridoma cell line and the B5-6T BGS hybridoma cell line, each incubated with an excess of RAH Ig Linker, biotinylated RABV GP, and Alexa 488 labeled streptavidin and then fixed with paraformaldehyde and stained with DAPI.

Monoclonal murine anti-gp130 antibody was incubated with LCX cells and K6H6/B5 cells, which do not express gp130, as negative control. After washing, APC conjugated anti-mouse IgG was incubated with tested cells. Flow cytometry was then performed to detect whether the tested cells expressed gp130 on their cell surface. The result as shown in FIG. 15 demonstrates that gp130 was observed on the LCX cells but not on the parental K6H6/B5 cells.

Example 3: Establishment of Stable Hybridomas Secreting Human Monoclonal Antibodies with Potent Poliovirus Neutralizing Activity The LCX cell line was used to generate hybridomas that stably secreting human Ig following fusion with primary human B cells. Following protocols standardized with the use of the B5-6T fusion partner cell line, we fused the LCX cell line to B cells from an individual immune to poliovirus (PV) (types 1-3) according to protocols described.[20] This created a population of hybridoma secreting human that were assessed for the expression of human IgG immunoreactive with poliovirus. The hybridoma supernatants were assessed by ELISA, enabling the identification and subcloning of hybridomas that stably secrete human mAbs capable of PV binding. The PV-reactive mAbs were tested for neutralization in vitro using the microneutralization tests listed in Table 2. Many mAbs were identified to have high neutralization potency (such as LX-2D6, LX_5G5, LX_4A4, LX_3E9, LX_1A7, LX_10C6 and LX_2E1), and four mAbs were identified that neutralized more than one strain.

Thus, a cell line that expresses constitutively active IL-6 receptor gp130 ΔYY, the LCX cell line, was created and demonstrated to be effective as a fusion partner with human B cells to create stable hybridomas secreting useful human monoclonal antibodies.

TABLE 2

Poliovirus neutralization titers of antibodies secreted by hybridomas made with LCX cells (values are given as the reciprocal of the highest dilution of a 1 mg/ml mAb solution giving 50% protection of cultures of the indicated Sabin and wild type PV strains).

| | Type 1 | | Type 2 | | Type 3 | |
|---|---|---|---|---|---|---|
| Antibody | Sabin | WT | Sabin | WT | Sabin | WT |
| 1 LX_2D6 | 204800 | 289631 | | | | |
| 2 LX_5G5 | 579262 | 409600 | | | | |
| 3 LX_4A4 | 102400 | 144815 | 12800 | 25600 | | |
| 4 LX_3E9 | 141 | 566 | 18102 | 102400 | | |
| 5 LX_1A7 | 141 | 9051 | 566 | 4525 | | |
| 6 LX_10C6 | | | | | | |
| 7 LX_2E1 | | | | | 2317048 | 3276800 |

Example 4: Creation of Fusion Partner Cell Lines Expressing an Anchor Protein

To create and establish mammalian cell line expressing an Anchor protein capable of interacting with an Ig-linker protein on the outer plasma membrane of a cell, the following experiments were performed. In the current experimental setting, the Anchor comprised a tandem murine anti-rabbit scFv moiety, which was designed to bind to rabbit anti-human IgG (RAH) as an Ig Linker as described in Example 1 and form a first immune complex. LCX and B5-6T cells were cultured and maintained as described.[21] LCX cells were cultured and maintained in ATCC-formulated RPMI-1640 Medium with 10% of fetal bovine serum under the atmosphere with 5% $CO_2$ at 37° C.

The second immune complex was formed by the RAH captured by Anchors and human immunoglobulins as target proteins. An optional third immune complex was formed by human immunoglobulins and their corresponding antigens. The existence, specificity, affinity, titer, amount, and biological activity of the binding in the three immune complexes described above were analyzed. LCX and B5-6T cells were transduced with replication defective lentiviral particles generated with the DNA with the construct described in Example 1 via conventional methods.[12,13]

The expression of the tandem scFv on the outer plasma membrane was detected by immunostaining of the transduced cells with a primary biotinylated anti-mouse IgG, followed by Streptavidin APC. Cells expressing the tandem scFv were isolated by flow cytometry four times to generate stable high-expressing, homogeneous populations of cells. Comparison of anti-mouse IgG staining of the parental (LCX, B5-6T) vs. transduced cell lines (LCX BGS, B5-6T BGS) by flow cytometry establishes the existence of two fusion partner cell lines that express tandem scFv.

These results were plotted in FIG. 2A for B5-6T cells and FIG. 2B for LCX cells respectively. These experiments also establish that the expression of the Anchor protein on the outer surface of a mammalian cell endows the outer surface with murine immunoglobulin antigens that could be recognized by an Ig-linker reactive with murine immunoglobulin antigens.

Example 5: Creation of Immune Complexes Containing Human IGG on the Surface of LCX BGS and B5-6T BGS Cells Anchors can interact with Linkers in one of two ways. In one embodiment, Anchors can be recognized or bound by Linkers. For example, the Anchor may contain an antigen, such as a c-myc tag or the scFv sequences themselves (as in the present embodiment), which is recognized by the Linker protein (e.g. and antibody specific for the myc tag or the scFv moieties). For example a cell is contacted with a goat antibody specific for the c-myc tag sequence, or with a goat antibody specific for murine scFv antigens, washed, and further incubated with an APC-labeled anti-goat secondary antibody, and then is analyzed by flow cytometry, demonstrating the ability of the c-myc tag or murine Ig epitopes to be recognized by antibodies that may be used as Linkers. Alternatively, the Anchor may itself contain an antigen binding domain that is able to bind an epitope on the Linker protein.

Figures 3A, 3B, 4A, 4B:
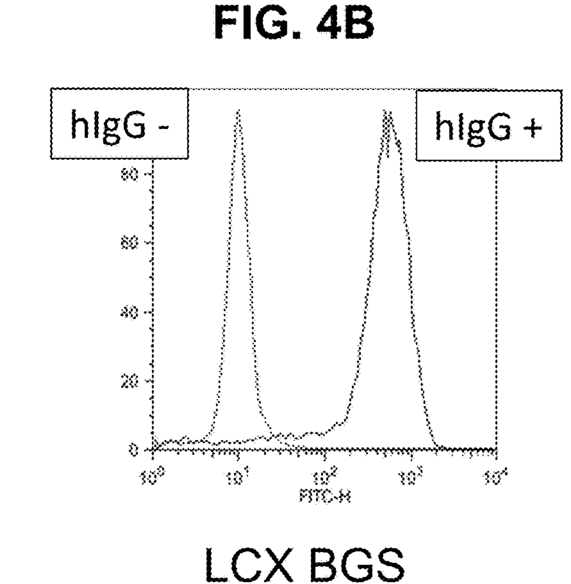
FIGS. 3A and 3B are graphs of flow cytometry showing that the tandem murine scFv (BGS) mediates binding of rabbit IgG (RAH, Linker) to B5-6T and LCX fusion partner cell lines as described in Example 3.
FIGS. 4A and 4B are graphs of flow cytometry showing that fusion partner cell lines that are bound to rabbit Igs specific for human Ig (RAH, Linker) bind to polyclonal human IgG (hIgG, target protein).

In the present embodiment, this domain is a tandem scFv that specifically binds rabbit Ig. We tested the ability of the Anchor expressed by LCX BGS and B5-6T BGS to bind to bind an Ig Linker composed of rabbit IgG specific for human Ig (RAH) via immunostaining of cell surface proteins followed by flow cytometry. Live LCX, LCX BGS, B5-6T, and B5-6T BGS cells were incubated with biotinylated RAH. After washing, APC conjugated Streptavidin was applied to the tested samples. Fluorescent signal from APC was then assessed by flow cytometry and the data was plotted in FIGS. 3A and 3B. LCX BGS and B5-6T BGS fusion partner cells significantly bound the RAH, compared to the LCX and B5-6T cells (FIGS. 3A and 3B). These results demonstrate that the expressed tandem murine scFv domain of the Anchor maintains its predicted affinity for rabbit Ig, and is therefore about to adhere rabbit Ig on the outer plasma membrane of the LCX BGS and B5-6T BGS fusion partner cell lines.

Figure 5A:
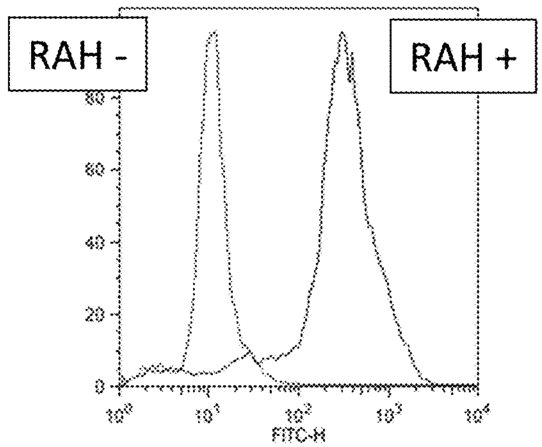
FIGS. 5A and 5B are graphs of flow cytometry showing that the binding of human Ig to the B5-6T BGS and LCX BGS fusion partner cell lines depends on the presence of rabbit Igs specific for human Ig (RAH, Linker).
Figure 5B:
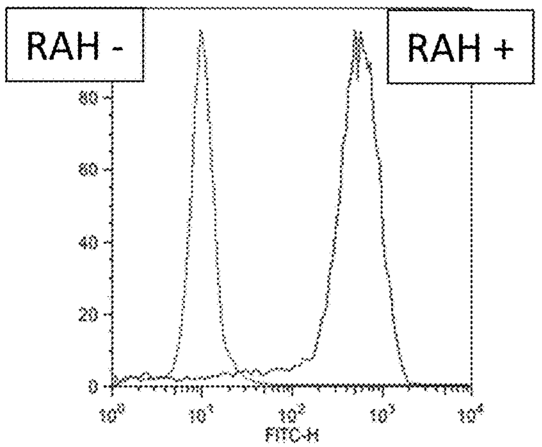
Figure 6A:
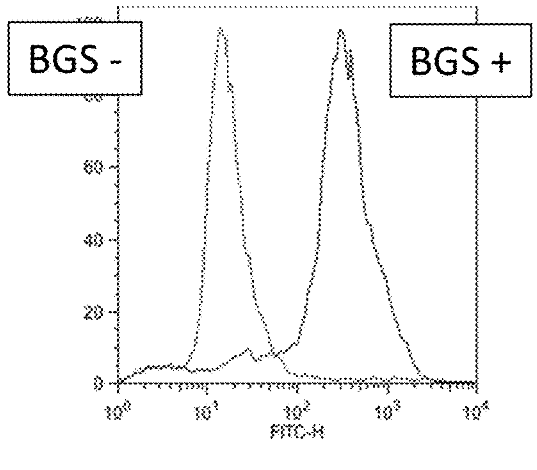
FIGS. 6A and 6B are graphs of flow cytometry showing that the tandem murine scFv (BGS) is required for RAH-mediated capture of human IgG by fusion partner cells.
Figure 6B:
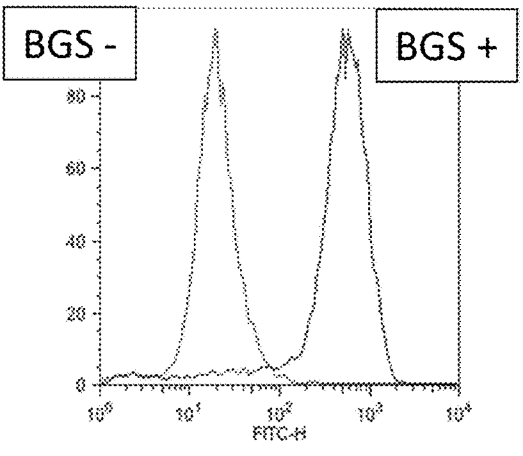
Figures 7A, 7B, 8A, 8B:
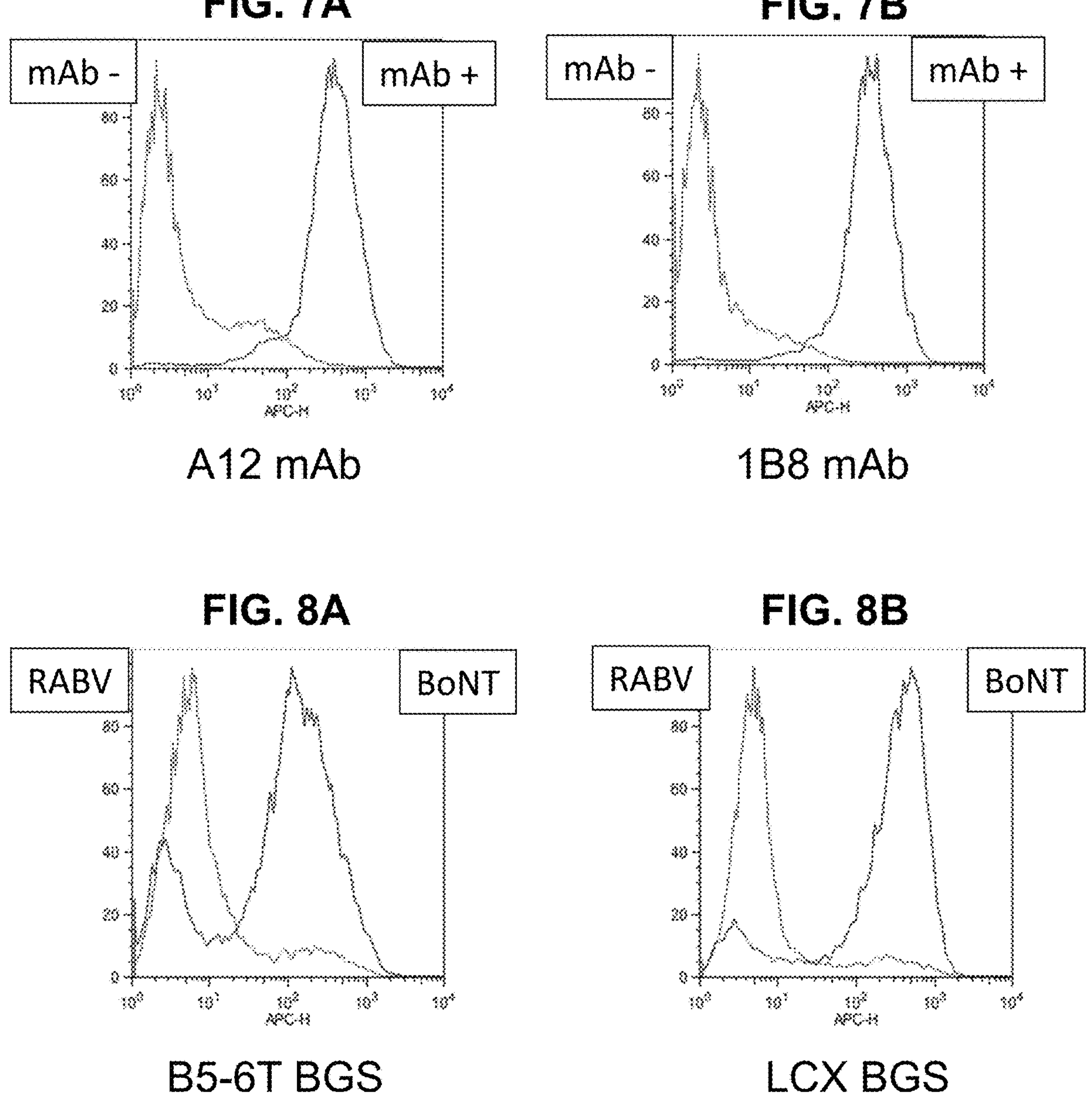
FIGS. 7A and 7B are graphs of flow cytometry showing that B5-6T BGS cells in the presence of RAH capture human IgG mAbs, A12 (FIG. 7A) and 1B8 (FIG. 7B), as target proteins.
FIGS. 8A and 8B are graphs of flow cytometry demonstrating that B5-6T BGS and LCX BGS cells complexed with a BoNT-specific mAb (as a target protein) bind to a biotinylated BoNT antigen, but not to a biotinylated rabies virus glycoprotein (RABV GP).

Anchor expression on the surface of the LCX BGS and B5-6T BGS cell lines enables the inducible adherence of human IgG. The LCX BGS and B5-6T BGS cell lines were incubated with RAH, washed, then incubated with or without polyclonal human IgG following RAH. Alexa 488 conjugated goat anti-human IgG was then applied for detection by flow cytometry. In both B5-6T BGS (FIG. 4A) and LCX BGS (FIG. 4B) fusion partner cells, polyclonal human IgGs were observed on the cell surface. To confirm that the binding of the human IgG to the surface of the LCX BGS and B5-6T BGS cell lines was dependent on the presence of the RAH Ig-Linker, we compared binding of human IgG to these cell lines in the presence and absence of the RAH, under the same conditions as described above (FIG. 5A, 5B). These data demonstrate that RAH is required for adherence of human IgG to the surface of both B5-6T (FIG. 5A) and LCX (FIG. 5B) fusion partner cells.

In an additional experiment, we tested whether expression of the Anchor protein (tandem murine scFv) by the LCX and B5-6T cell lines was essential for RAH-mediated binding of human IgG. Binding of human IgG, in the presence of RAH, to the LCX, LCX BGS, B5-6T, and B5-6T BGS cell lines was assessed by incubating RAH, human IgG and Alexa 488 conjugated goat anti-human IgG with the tested cells as described above. Flow cytometry was performed, demonstrating binding of human IgG to the LCX BGS and B5-6T BGS cell lines, but not to the LCX and B5-6T cells that did not express the Anchor. Therefore, fusion partner cell lines exhibited successful capture of human IgG only when the Anchor was present.

These data establish the existence of a functional Anchor protein expressed on the outer plasma membrane of a mammalian cell, which is able to bind RAH, indicating that the Anchor protein is able to form a first immune complex with an Ig Linker; that the immune complex forms on the exterior portion of the cell; that the Ig linker is able to form a second immune complex with a human IgG; and that the human IgG would not be adherent to the cell in the absence of either the Anchor or the Ig Linker protein. Furthermore, it establishes the existence of a novel immune complex that consists minimally of four components: a cell, an Anchor protein expressed on its outer plasma membrane, a Linker protein bound by the Anchor protein, and a heterologous IgG bound by the Anchor protein to the complex, and which requires the presence of the Ig Linker for interaction of the heterologous IgG with the cell and cell-containing immune complex.

Example 6: Expression of the Anchor Molecule on the Surface of Hybridoma Cells that Secrete Human IGG A novel and useful capability of the compositions and methods described herein is that they enable a protein secreted by a cell to be inducibly adhered to the surface of that cell. While adhered to the cell, the structural and/or functional features of the protein are assessed using assays that require a protein to be immobilized on a surface. In the present examples, in which the secreted protein is a mAb, such assays include, without limitation, antigen binding assays, tests for mAb glycosylation or isotype, immune-complex mediated functions such as lymphocyte stimulation or complement-dependent cytotoxicity, and catalytic activity.

Because the secreted mAb is physically associated with the cell that produces it, if a protein with desirable characteristics is found, the cell that secretes that protein can be readily identified and isolated. To demonstrate the inducible capture of secreted monoclonal antibodies on the surface of hybridoma cells that secrete them, we induced expression of the Anchor on two hybridomas that had previously been generated and found to stably secrete human mAbs, 8C5 and 9H2. 8C5 is specific for the rabies glycoprotein (RABV GP) and 9H2 is specific for poliovirus types 1, 2 and 3. The cells were transduced with retroviral particles containing the tandem murine scFv Anchor gene, resulting in the hybridomas 8C5 BGS hybridoma and 9H2 BGS. Expressions of tandem murine scFv (BGS) on the cell surface of the four hybridomas were evaluated via a method similar to the experiment described in Example 3. Biotinylated anti-mouse IgG was applied to the tested cells followed by incubation with APC conjugated streptavidin. The presence of scFv was then detected by flow cytometry. The results were plotted in FIG. 9A and FIG. 9B, respectively. The 8C5 BGS and 9H2 BGS hybridomas both displayed a positive peak of fluorescent signal compared to the parental hybridomas, 8C5 and 9H2, indicating expression of the Anchor on their cell surfaces.

Binding of RAH as an Ig Linker to the BGS hybridomas was further accessed via the protocol described in Example 3. Biotinylated RAH were incubated with 8C5, 8C5 BGS, 9H2, and 9H2 BGS cells, followed by washes and an incubation with APC conjugated Streptavidin. Flow cytometry results showed that both Anchor-expressing hybridomas (8C5 BGS, FIG. 10A and 9H2 BGS, FIG. 10B) successfully captured biotinylated RAH and formed the second immune complex, whereas the 8C5 and 9H2 hybridomas did not. We assessed the surface capture of mAbs produced by the 9H2 BGS and 8C5 BGS hybridomas in the presence of the RAH Ig linker. The 8C5, 8C5 BGS, 9H2, and 9H2 BGS hybridomas were cultured in the presence of the RAH Ig linker simultaneously with an Alexa 488 conjugated goat anti-human IgG. The peaks of fluorescent signal from both 8C5 BGS (FIG. 11A) and 9H2 BGS (FIG. 11B) hybridomas were shifted to the positive scale range compared to those of the 8C5 and 9H2 hybridomas, indicating that the tandem murine scFv (BGS) increases (Anchor), in the presence of the RAH Linker, increased adherence of the secreted monoclonal human IgG to the hybridomas that secreted them.

A further experiment was performed to assess the role of RAH Ig Linker in binding of the secreted mAbs to the hybridomas. Both 8C5 BGS (FIG. 12A) and 9H2 BGS (FIG. 12B) BGS hybridomas were incubated with Alexa 488 conjugated goat anti-human IgG with or without RAH. An increased capture of secreted human IgG was observed with the presence of RAH in both hybridomas, as indicated by a broader fluorescent peak whose center was shifted toward the positive direction of the scale as well as a larger area under the curve in the graphs of flow cytometry compared to the one without RAH.

Figure 13:
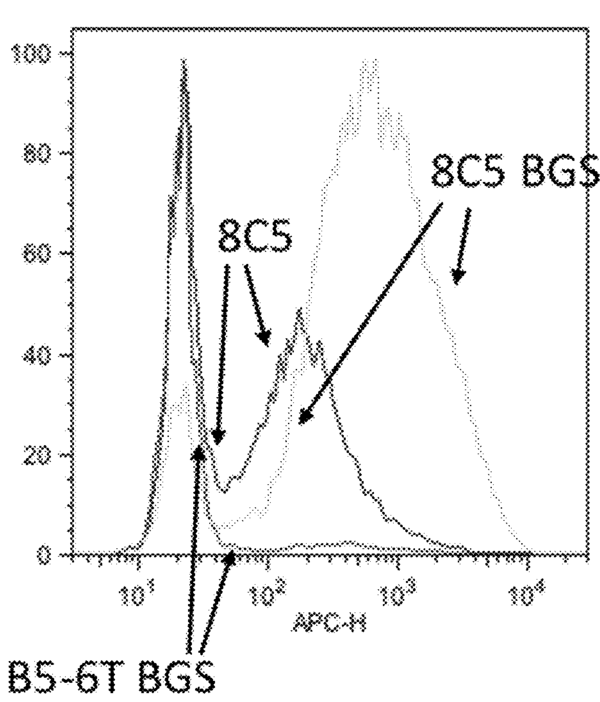
FIG. 13 is a graph of flow cytometry demonstrating the 8C5 BGS hybridoma incubated in the presence of RAH binds to the RABV GP significantly better than does the 8C5 hybridoma. In addition, the B5-6T BGS fusion partner cell line does not bind RABV GP, as described in Example 4.

Example 7: Binding of Specific Antigen by a Secreted MAB Captured on the Surface of a Hybridoma Secreting the MAB and Establishment of the First, Second, and Third Immune Complexes on the Surface of a Hybridoma Cell To establish the existence of the third immune complex formed by human IgG and antigen, a further experiment was performed. As noted above, the 8C5 mAb binds RABV GP. We cultured the B5-6T, 8C5, and 8C5 BGS cells overnight in the presence of an excess of RAH, then washed the cells and added additional RAH, biotinylated RABV GP antigen, and APC labeled streptavidin as a detection molecule. The result shown in FIG. 13 revealed a higher percentage of antigen positive cells and a stronger binding of antigen in the sample of 8C5 BGS hybridoma compared to B5-6T fusion partner cells and 8C5 hybridoma, indicating a successful and specific formation of the first, second and third immune complexes.

This experiment establishes the existence of a useful and novel cell-containing immune complex that comprises a mAb secreted by a cell and is adhered to the outer plasma membrane of the cell via a bridge that consists of a membrane bound Anchor protein and an Ig-Linker protein, in which the mAb binds to its antigen and the antigen is additionally bound to a detection molecule. By the use of the methods and compositions described herein, a cell that secretes a mAb capable of binding the antigen is readily identified and isolated.

The nature of the cell-containing immune complexes was further characterized by fluorescence microscopy (FIGS. 17A-17D). We incubated the indicated 8C5 and 8C5 BGS and B5-6T BGS cell lines with an excess of RAH Ig Linker, biotinylated RABV GP, and Alexa 488 labeled streptavidin. We fixed the cells with paraformaldehyde, stained them with DAPI and examined them with a fluorescent microscope. Many of the 8C5 BGS cells show a fluorescent signal indicating the adherence of the RABV GP, whereas the 8C5 cells do not, even though they are secreting the same mAb. This corroborates the flow cytometry data, indicating the presence of the three immune complex components form on the surface of the cell and that mAb complex containing an antibody can be analyzed for its antigen-binding specificity, which is information that in turn can be cross-referenced with the cell that secretes it.

Examination of the intensity and pattern of RABV GP staining on the 8C5 BGS cells reveals that the cells have different levels of signal. To determine whether this finding reflects differences in the level of Anchor protein expression by the clones, 8C5 BGS cells and B5-6T BGS cells were cultured with RAH and an Alexa 488-labeled goat anti-rabbit IgG secondary antibody (FIG. 18). The amount and distribution of the Alexa 488 label on the B5-6T BGS cells is essentially the same on every cell, a result that is consistent with the flow cytometry data that demonstrates homogeneity of Anchor expression on the B5-6T BGS and 8C5 BGS cell lines (FIGS. 3A and 10A).

Despite the consistent Anchor expression levels on the surface of the 8C5 BGS cells, the amount of RABV GP labeling varies widely among the cells (FIG. 17). This suggests that the individual 8C5 BGS cells in the population express different levels of mAb, and furthermore that the excess RAH in the cell culture medium is sufficient to prevent mAbs secreted by one cell from binding to another cell.

It is also instructive that the binding patterns of the RAH to the B5-6T BGS and 8C5 BGS cells observed in FIG. 18 differ. Whereas the staining on the B5-6T BGS cells is evenly distributed, the staining on the 8C5 BGS cells is highly localized, and adopts a single high-intensity "cap" structure on cell membrane. As the RAH in this experiment is a mAb, this suggests that the presence of the human mAbs secreted by the 8C5 BGS cells enable immune-complex mediated cross-linking of the Anchor domains on the surface of the cells. These immune complexes consist of Anchor domains that recognize the rabbit mAbs, which bind the human mAbs, which are in turn able to recruit additional rabbit and human mAbs, from the culture medium and cell, respectively.

The divalent nature of the rabbit mAb enables complexes to be associated with each other in a localized array on the outer plasma membrane. Binding of the RABV GP in this same pattern on the 8C5 BGS cells (FIG. 17) indicates that the mAbs in the immune complex array are not prevented from interacting with their target antigens. Thus, in the presence of a multivalent Ig Linker, immune complexes that contain multiple copies of the secreted mAb may be formed on the surface of cells expressing an Anchor protein. Furthermore, the mAbs in these immune complexes are configured in a way that enables canonical binding to their target antigen.

Example 8: Identification and Isolation of Cells Stably Secreting a Desirable Quantity of a Protein from Among a Heterogeneous Population of Cells The 8C5 BGS cell population is again subjected to the experiment shown in FIG. 17, in which 1 million cells are plated in a 10 cm culture dish. The 8C5 BGS cells are cultured with an excess of RAH Ig Linker, biotinylated RABV GP, and Alexa 488 labeled streptavidin. Following the formation of the immune complexes, the cells with the highest level of 8C5 mAb expression (as indicated by the level of Alexa 488 fluorescence) are pipetted from the plate or are isolated by flow cytometry, thereby identifying high expressor subclones that can be cultured to produce optimal amounts of the 8C5 mAb.

In a variation of this experiment, the amount of IgG expressed is measured instead of specific antigen binding. One million 8C5 BGS cells are plated in a 10 cm culture dish, cultured with an excess of RAH Ig Linker specific for the human IgG Fc domain (with or without a sub-molar quantity of isolated human IgG Fc domains), biotinylated murine IgG specific for the human IgG FAb domain, and an Alexa 488 labeled streptavidin. Following these methods, hybridomas that secrete optimal amounts of mAb are identified and isolated.

A plasmid that expresses a gene that encodes human erythropoietin (EPO) as well as a gene encoding a blasticidin resistance protein is introduced into a population of CHO cells that homogeneously express the Anchor protein. The cell population is passaged in the presence of blasticidin until a polyclonal population is derived that is resistant to blasticidin and therefore may express EPO. The cell population is washed and cultured in the presence of an excess of rabbit Ig specific for EPO and an Alexa 488 labeled, murine mAb specific for human EPO. Cells are analyzed by fluorescence microscopy or flow cytometry and those expressing the highest levels EPO expression are isolated and expanded for further study.

In a similar experiment, the expressed EPO protein incorporates a protein tag, such as a 6×HIS tag. Following blasticidin expression, the cells are cultured in the presence of an excess of rabbit Ig specific for the 6×HIS tag, and the Alexa 488 labeled, murine anti-EPO mAb. To reduce binding of secreted EPO to any cells that did not secrete it, a fraction of the amount of the anti-6×HIS-specific rabbit Ig is mixed with a heterologous polypeptide that also contains a 6×-HIS tag, but which is not recognized by the murine anti-EPO mAb.

In a further modification of this experiment, the murine anti-EPO mAb is conjugated with biotin and the CHO cells are maintained in suspension culture. Following the formation of the immune complexes, the cells are rinsed and mixed with magnetic beads conjugated to streptavidin. The cell complexes are subjected to a magnetic field that enables separation of the EPO-expressing cells from cells that do not express EPO. In an additional variant, the EPO gene is modified to join a Myc tag to the secreted EPO protein. The Ig Linker is a polyclonal antiserum immunoreactive with the Myc tag, such that it will adhere the EPO to the cell surface through its interactions with the Myc tag on both the Anchor and the secreted EPO molecules. Additionally, the detection molecule is biotinylated murine anti-EPO mAb joined with either streptavidin Alexa 488 or is streptavidin-conjugated magnetic beads.

Example 9: Optimization of a Fusion Partner Cell Line Expressing the Anchor Protein Hybridomas expressing the Anchor protein that are enabled by the methods and compositions as described herein can be established by different methods. In one example, the expression of the Anchor protein is induced by retroviral gene transduction of an existing mAb-secreting hybridoma. Alternatively, fusion partner cells that express the Anchor are fused to B cells to produce hybridomas that express both the Anchor protein and the mAb encoded by the Ig genes originating in the B cell.

As in the examples above, nucleic acids encoding the Anchor protein are introduced into fusion partner cell lines and a homogeneous population of cells that express the fusion partner cell line is established. Single cells from that population are isolated and expanded. DNA from individual clones is isolated, digested with restriction enzymes, and tested by Southern Blotting. The Southern Blotting data enables the determination of the number and nature of genomic copies of the Anchor transgene present within each cell clone and a panel of distinct clonal populations is designated. The cells are expanded for further study. Each distinct population of Anchor-expressing fusion partner cell lines is fused to a B lineage cells following standard methods, plated in 96 well plates at a suitable dilution, and then subjected to HAT selection. Following the outgrowth of clones, the cells in the wells are washed and contacted with a rabbit Ig conjugated Alexa 488, washed and examined by fluorescence microscopy.

The fusion partner cell lines that gave rise to the most consistent expression of Anchor in the new hybridomas (90% or better) are used for additional fusions. Fusion partner cell line clones that do not achieve this milestone receive an additional retroviral transduction of the Anchor gene. This second Anchor gene has a His tag in place of the Myc tag, and the construct may or may not contain an additional antibiotic resistance gene. Following transduction of the Anchor-expressing cell clone with the second Anchor construct, cells that express the second Anchor construct are identified through their expression of the His tag sequence, isolated by flow cytometry, and re-tested in the cell fusion experiment described previously.

Example 10: Creation and Screening of Hybridoma Libraries Expressing Monoclonal Antibodies Fusion partner cell lines of the present invention can be used for the creation and screening of libraries of hybridomas that express monoclonal antibodies. In principle, the method could be used with B lineage cells from any mammalian species, although the B5-6T BGS and LCX BGS cell lines are suited for creating hybridomas that stably secrete human mAbs. Methods for creation of hybridomas using cells such as the B5-6T cell line, are well known to the state of the art for use with B cells from many different species, including human B cells,[22, 23] murine B cells from wild type mice[24], from mice transgenic for human immunoglobulin gene sequences[25], and from rabbits.[26]

Human peripheral blood mononuclear cells are obtained from volunteers 8 days after they have received the inactivated poliovirus vaccine (IPV) and isolated using Ficoll centrifugation, and then stored frozen in 90% Hyclone Defined FBS (Invitrogen, Carlsbad, CA) and 10% DMSO (Sigma-Aldrich) under liquid nitrogen until use. Prior to cell fusion, CD27-positive cells are isolated with anti-CD27 magnetic beads (Miltenyi Biotec, Auburn, CA) according to the manufacturer's instructions. These cells are cultured for 8 days in the presence of multimeric CD40L (Ultra-CD40L, courtesy of Richard Kornbluth, M.D., Multimeric Biotherapeutics, Inc, La Jolla, CA, USA) in IMDM supplemented with IL-2 and other cytokines and pen/strep. The cultured cells are fused to the B5-6T BGS or LCX BGS fusion partner cell lines by electrofusion and the cells are seeded at 100-2000 primary cells per well in 96-well plates or at a density of 10,000-200,000 cells per 10 cm culture dish. The nascent hybrid cells are selected with HAT (Sigma-Aldrich) in Advanced RPMI+1% fetal calf serum.

Following the emergence of HAT resistant hybridomas, at approximately 7-17 days following fusion, the cell culture medium is removed and RAH is added, along with biotinylated poliovirus types 1, 2, and 3, and Streptavidin Alexa 488. Cells are incubated for 1-8 hours, and cells that acquire a fluorescent signal are isolated by pipetting and placed into 96 well plates. 3-10 days later, the cells are again tested for binding to PV. In an alternate method, streptavidin conjugated magnetic beads are added to the hybridomas in addition to, or in place of, the Streptavidin 488 beads. Following the cell incubation, cells expressing PV mAbs are isolated on a magnetic affinity column.

Example 11: Creation and Maintenance of Stabilized Hybridoma Expression Libraries (SHELs)

An important weakness in the current state of the art of mAb cloning by hybridoma methods is that the hybridoma libraries cannot be maintained in polyclonal culture, because the hybridomas that secrete mAbs tend to be overgrown by the non-secreting hybridoma cells, which proliferate faster. Consequently, hybridoma libraries are typically discarded after screening. This places practical limitations on the number of tests that can be performed on each hybridoma and loses potentially valuable B cell samples.

The methods and compositions described herein allow polyclonal hybridoma populations to be analyzed and sorted to create populations that only secrete mAbs and can therefore be maintained in culture indefinitely and cryopreserved as necessary. As previously described, human or murine B cells are fused to a fusion partner cell line that expresses the Anchor protein and subjected to HAT selection, are plated at a density of approximately 0.1-10 million B cells per 10 cm dish. Following the establishment of HAT-resistant clones, the cells are washed and incubated with excess of rabbit anti-human (RAH) Ig Linker, biotinylated secondary antibody specific for the secreted mAb (either a goat anti-human Ig or a goat anti-murine Ig Fc domain), and streptavidin conjugated magnetic beads. The hybridomas are gently removed from the culture dish and the mAb-secreting hybridomas are positively selected on a magnetic column.

In an alternate method, the hybridomas are contacted with Alexa 488 conjugated streptavidin and the positive cells are isolated by flow cytometry. The positively selected, Ig-expressing cultures are then expanded, maintained, and screened with additional antigens or functional assays as enabled by the expression of the Anchor according to the methods described herein. For quality control, the complexity of the mAb population is assessed and prospectively monitored by common methods, including deep sequencing of the immunoglobulin gene repertoire and the calculation of a Gini Index.[27]

In this Example shown herein, human primary B cells were fused to the LCX BGS fusion partner cell line, and HAT resistant cell populations were selected, after which cells expressing human IgG were isolated from the non-expressing cells, thereby creating a Stabilized Hybridoma Expression Library (SHEL™). In the creation of a SHEL library expressing polyclonal human IgGs, we fused a population of human B cells to the LCX BGS fusion partner cell line and plated the fused cells in five 96 well plates at a density of approximately 1000 B cells per well. Fourteen days after fusion (day 14), the plates were screened for expression of PV antibodies following conventional methods. After a panel of 6 clones were selected and removed from the 96 well plates, on day 16 after the fusion, the cells in the remaining wells were pooled and cultured for an additional 3 days in culture medium without HAT.

Figure 23A:
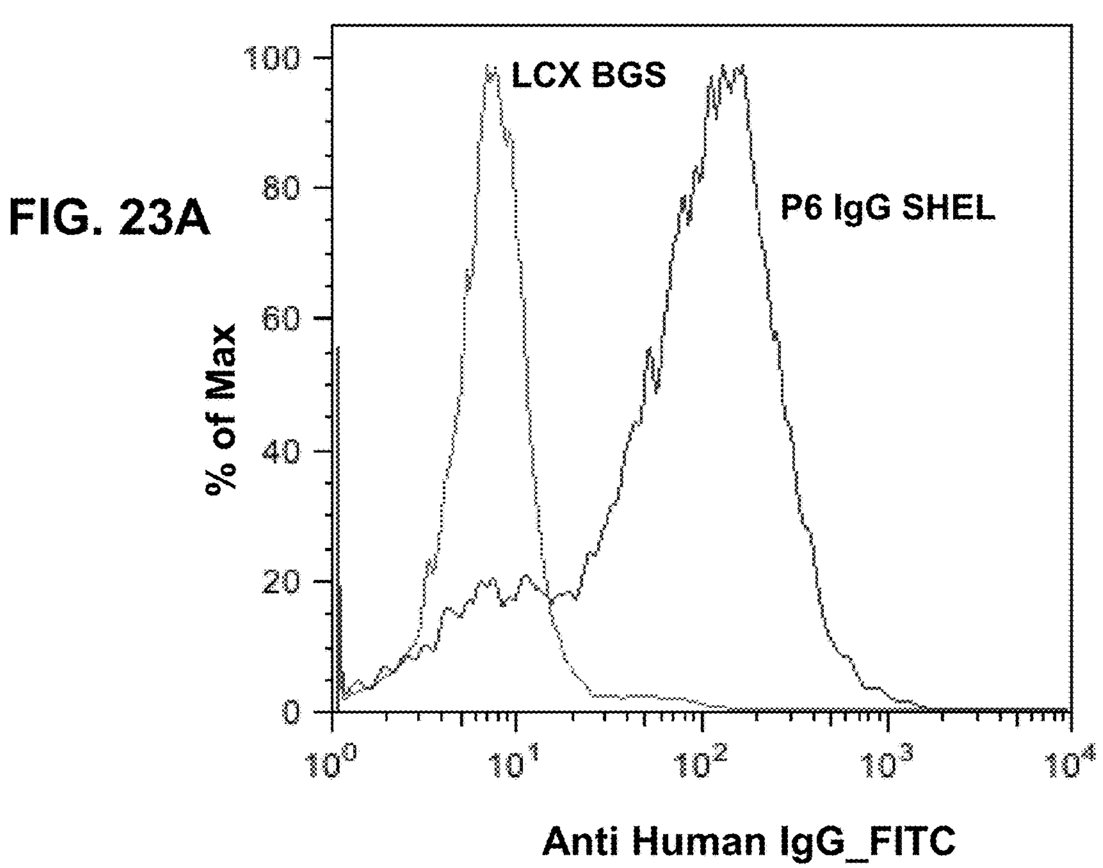
FIG. 23A provides a graph of flow cytometry showing a population of hybridomas highly enriched for expression of human IgG, defined as a Stabilized Hybridoma Expression Library (SHEL). Briefly, FACS sorting was performed for the selection. A population of hybridomas produced by fusion of the LCX-BGS cells with primary human B cells was subjected to a positive selection for those expressing human IgG by the following method: they were first washed and incubated overnight with excess of Linker, Rabbit $F(ab')_2$ fragment anti-human IgG (H+L) (Southern biotech Cat. No 6000-01) in culture medium. The cells were then washed twice with 1% PBS–BSA, mixed with biotinylated protein A (Sigma Aldrich Cat. No 2165) and incubated on ice. After one hour, the cells were washed with 1% PBS–BSA and then mixed with Alexa Flour 488 conjugated streptavidin (Jackson Immuno Research Cat No. 016-540-084) and incubated on ice for 45 min, then washed again. The population of cells expressing human IgG was then isolated by FACS on the BD FACSAriaII. This positive selection was repeated 2 more times, after which the population of cells was highly enriched for human IgG-expressing cells, as shown by flow cytometry result plotted. This polyclonal population of cells which is positively selected for those that express IgG and demonstrates stabilization of IgG expression, is a human IgG SHEL population.

Then the cells were subjected to a positive selection for those expressing human IgG by the following method: they were first washed and incubated overnight with excess of Linker, Rabbit F(ab')2 fragment anti-human IgG (H+L) (Southern biotech Cat. No 6000-01) in culture medium. The cells were then washed twice with 1% PBS–BSA, mixed with biotinylated protein A (Sigma Aldrich Cat. No 2165) and incubated on ice. After one hour, the cells were washed with 1% PBS–BSA and then mixed with Alexa Flour 488 conjugated streptavidin (Jackson Immuno Research Cat No. 016-540-084) and incubated on ice for 45 min, then washed again. The population of cells expressing human IgG was then isolated by FACS on the BD FACSAriaII. This positive selection was repeated 2 more times, after which the population of cells was highly enriched for human IgG-expressing cells, as shown by flow cytometry (See FIG. 23A).

Figure 23B:
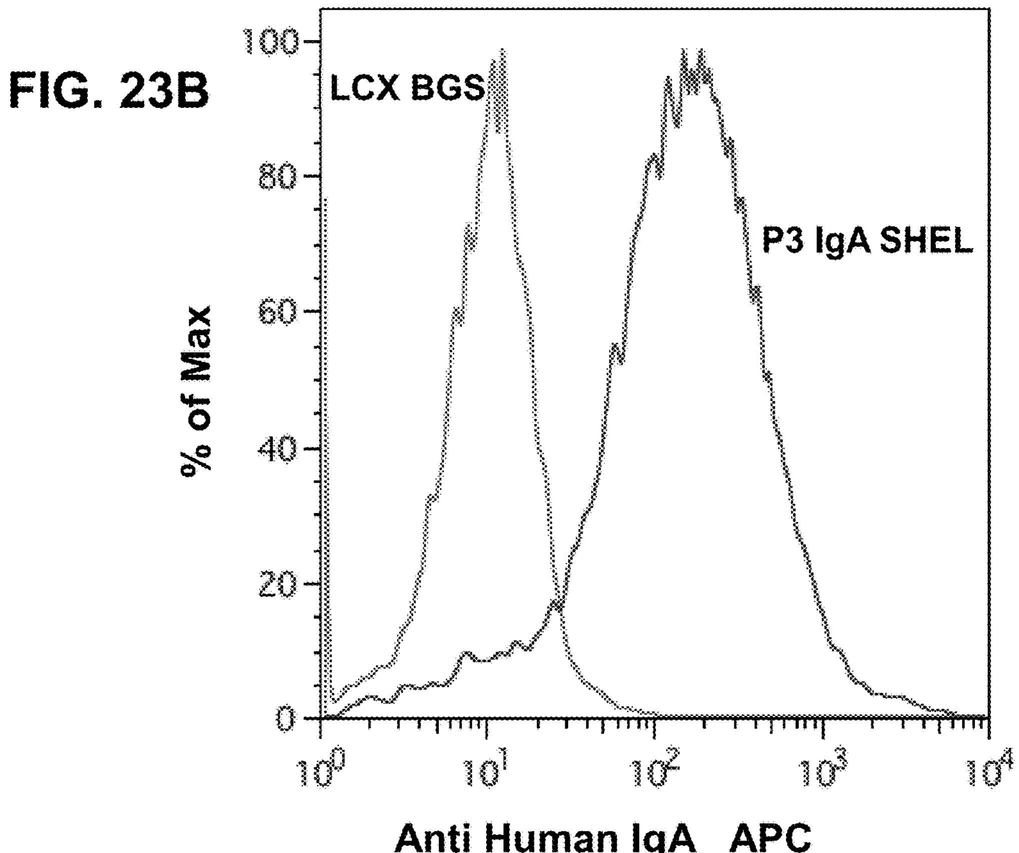
FIG. 23B provides a graph of flow cytometry showing highly enriched human IgA-expressing cells. Briefly, similar to the experiment depicted in FIG. 23A, a population of hybridomas produced by fusion of the LCX-BGS cells with primary human B cells was subjected to a positive selection for those expressing human IgA. This positive selection was repeated 2 more times, after which the population of cells was highly enriched for human IgA-expressing cells, as shown by flow cytometry result plotted. This polyclonal population of cells positively selected for those that express IgG, and demonstrates stabilization of IgG expression over, is a human IgA SHEL population.

A similar experiment was performed fusing B cells from a different donor to the LCX BGS cell line. On the 16th day following cell fusion, cells from five 96 well plates were pooled, cultured for 3 days, and then positively selected for those expressing human IgA. The cells were washed and incubated overnight with excess of Linker, Rabbit anti-human IgA (Abcam Cat No ab193189). The cells were then washed twice with 1% PBS–BSA and then mixed with Goat F(ab)2 anti-human IgA-Alexa Fluor 647 (Southern Biotech Cat No. 2052-31) and incubated on ice for 45 min. The cells expressing human IgA were then separated from non-expressing cells by FACS. The cells were subjected to this positive selection two times. The Flow Cytometry data from the second sort is shown in FIG. 23B.

Example 12: Identification of MABS with Immune Complex-Dependent Functions

It is well known that many functions exerted by antibodies depend on the formation of immune complexes. For example, immune complexes consisting of multiple IgG antibodies are able to activate the classical complement pathway, activate T cells, and, through Fc receptors, activating effector responses in macrophages, NK cells, and neutrophils.[28, 16, 29]

Methods for assessing such immune complex mediated functions are well known in the art. In the present example, hybridomas are screened for T cell activation induced by immune complexes displayed on their outer plasma membrane using the present invention using well-known tests for T-cell activation, induction of CD154 expression by T cells, following an established protocol for detection of T cell activating stimuli.[30]

Peripheral blood mononuclear cells are obtained from human subjects with rheumatoid arthritis or cancer and fused to the B5-6T BGS or LCX BGS fusion partner cell lines plated at a density of approximately 1000 B cells per well in 96 well plates and subjected to HAT selection. Following the establishment of HAT-resistant clones and conversion to HT-containing medium, the cells are washed and approximately 1,000-100,000 PBMCs or CD3+ T cells are added to the culture dish. The cells are incubated with excess of RAH Ig Linker, murine stimulatory IgGs (anti-CD28, anti-CD49d), biotinylated secondary antibody specific for the human CD154, and streptavidin Alexa 488. T cells adjacent to hybridomas expressing immune complexes will activate expression of CD154. Staphylococcal enterotoxin B are used as a positive control in some wells. Hybridoma cells associated with T cell activation are isolated from the positive wells, expanded and tested for continued Ig expression using the method described above. These cells are then re-tested for T cell activation under the same conditions, except that a negative control sample is included in which the RAH Ig Linker is substituted with a monomeric RAH Ig-Linker, which is unable to induce the concatemerized multimeric immune complexes that are made by the mAb and polyclonal Ig Linkers.

Example 13: Characterization of Antigens Bound to MAB-Secreting Hybridomas

Hybridomas prepared as described herein that secrete mAbs capture them on their outer plasma membrane in concatenated immune complexes that will be stabilized by avidity effects that remain after the Anchor has been cleaved from the cell surface, and which can be used for characterization of the bound antigen. An Anchor molecule which contains a tev protease tag substituted for the Myc tag described previously is expressed in a hybridoma cell that secretes a mAb specific for an antigen that is poorly characterized, but which is known to exist within an antigen mixture that contains multiple antigens. The antigen mixture is first biotinylated. Then, the Anchor expressing cell line is incubated with an excess of the Ig Linker, which adheres the secreted mAb to the hybridoma cells surface, to the biotinylated antigen mixture, and to streptavidin Alexa 488. Following visual confirmation that the antigen bound to the cell surface, the cells are removed from the culture medium and treated in conditions favorable for cleavage by the AcTEV protease (Thermo Fisher). Following the cleavage reaction, the cells are removed from the supernatant by centrifugation, and, if desired, the AcTEV protease is removed by size exclusion chromatography. The resultant sample is analyzed to identify the composition of the antigen bound to the mAb by mass spectrometry or other methods appropriate for characterization of the bound antigen.

Example 14: Transient Transfection of A12 in 293 OCMS Cell Line

The 293T or 293T OCMS cells were plated at $5\times10^4$ cells/well on round Corning™ BioCoat™ 12 mm #1 German Glass Coverslips (Corning, Cat. No 354087) in 24 well plate and incubated at 37° C. in 5% CO2 incubator. After overnight incubation, transient transfection was performed with 0.5 or 1 μg each of A12 heavy and light chain DNA using X-treme Gene 9 DNA gene transfection reagent. After 24 hours, the medium was removed from each well and added 500 μl of DMEM with 10% FBS with 1 μg/ml of rabbit anti-human IgG Fc specific mAb (Abcam H169-1-5) and incubated overnight. The following day (48 hours after transfection), the cells were washed thrice with PBS containing 1% BSA (PBS–BSA) and Alexa Fluor 488 conjugated F(ab)2 fragment of goat anti human IgG F(ab)2 fragment specific (Jackson Immuno Research, Cat No 109-546-097) at 1:200 in PBS–BSA and incubated for 1 hour at 37° C. in a CO2 incubator. After one hour incubation, cells were washed thrice with PBS–BSA and fixed with 4% paraformaldehyde in PBS for 15 minutes at room temperature. After fixation, cells were washed once with PBS and once with dH2O and then the coverslips were mounted with ProLong® Gold Antifade reagent with DAPI (P36935, Thermo Fisher Scientific) and imaged with a C2+ Nikon confocal microscope with 63×/1.3 NA oil objective; images were analyzed with ImageJ software (https://imagej.nih.gov/ij/). See FIG. 19.

Example 15: Establishment of Stable Hybridomas Secreting Human Monoclonal Antibodies with Potent Poliovirus Neutralizing Activity The LCX BGS cell line was used to generate hybridomas that stably secrete human IgG following fusion with primary human B cells. Following protocols standardized with the use of the B5-6T fusion partner cell line, we fused the LCX BGS cell line to B cells from two individuals immune to poliovirus (PV) (types 1-3) according to protocols described.[20] Experiments are performed with whole, unlabeled, live or UV-C-inactivated PV virions (Sabin vaccine strains)[41]. This created populations of hybridomas secreting human IgG that were assessed for the expression of IgG immunoreactive with type 3 Poliovirus. The hybridoma supernatants were assessed by ELISA, enabling the identification and subcloning of hybridomas that stably secrete human mAbs capable of PV binding. We tested the neutralization titers of 7 human mAbs (Table 3 below) in the microneutralization assay, tabulating the results as the reciprocals of the dilutions that protect 50% of the cell cultures against challenge with 100 TCID50 of the Sabin 3 and Saukett 3 PV strains. All of the mAbs had type 3 PV neutralizing activity against both strains.

TABLE 3

Neutralization activity of poliovirus (PV) mAbs derived from LCX BGS fusion partner cell lines

| | | Type 3 | |
|---|---|---|---|
| mAb | Donor | Sabin 3 | Saukett 3 |
| 4A8 | P3 | 1024000 | 861078 |
| 1A9 | P3 | 608874 | 724077 |
| 3A3 | P3 | 724077 | 861078 |
| 5E12 | P3 | 3200 | 6400 |
| 5H3 | P6 | 114487 | 34037 |
| 5F6 | P6 | 1024000 | 608874 |
| 4G4 | P6 | 323817 | 385086 |

Figure 24:
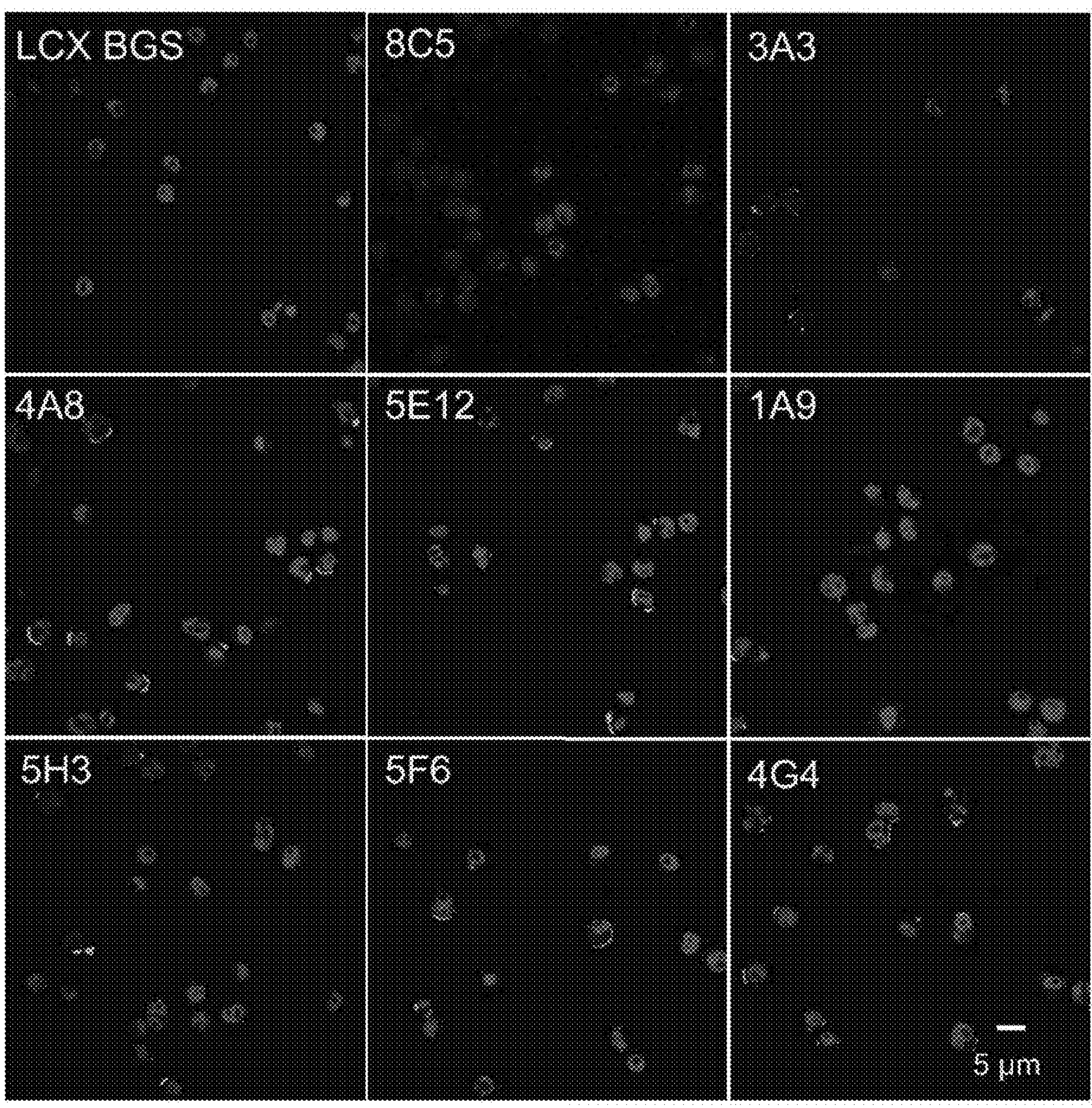
FIG. 24 shows 9 microscopy panels illustrating binding of type III PV to OCMS hybridomas secreting human anti-PV IgG mAbs as described in Example 16.

We tested these hybridomas for adherence of their secreted human IgGs. FIG. 24 shows 9 microscopy panels illustrating binding of type III PV to OCMS hybridomas secreting human anti-PV IgG mAbs. The hybridoma secreting human PV mAbs were analyzed by immunofluorescence for binding to biotin-labeled type III PV, after an overnight incubation in the presence of the RAH linker antibody. PV was detected using an Alexa-Fluor 488 streptavidin and analyzed by confocal microscopy. Nuclei were stained with DAPI. Scale bar=5 μm. All of the seven hybridoma populations isolated in this experiment demonstrated green signal on the periphery of many of their cells, except for the LCX BGS fusion partner cell line and the 8C5 BGS hybridoma (which expresses an IgG specific for rabies glycoprotein). Many of the cells adhered the PV in a cap-like structure on one pole of the cell. In each of the images of the PV some of the cells did not exhibit binding, even when they were adjacent to strongly positive cells, indicating that the conditions demonstrated (including an excess of the RAH) are sufficient to prevent hybridomas from binding mAbs they did not secrete.

Figure 25:
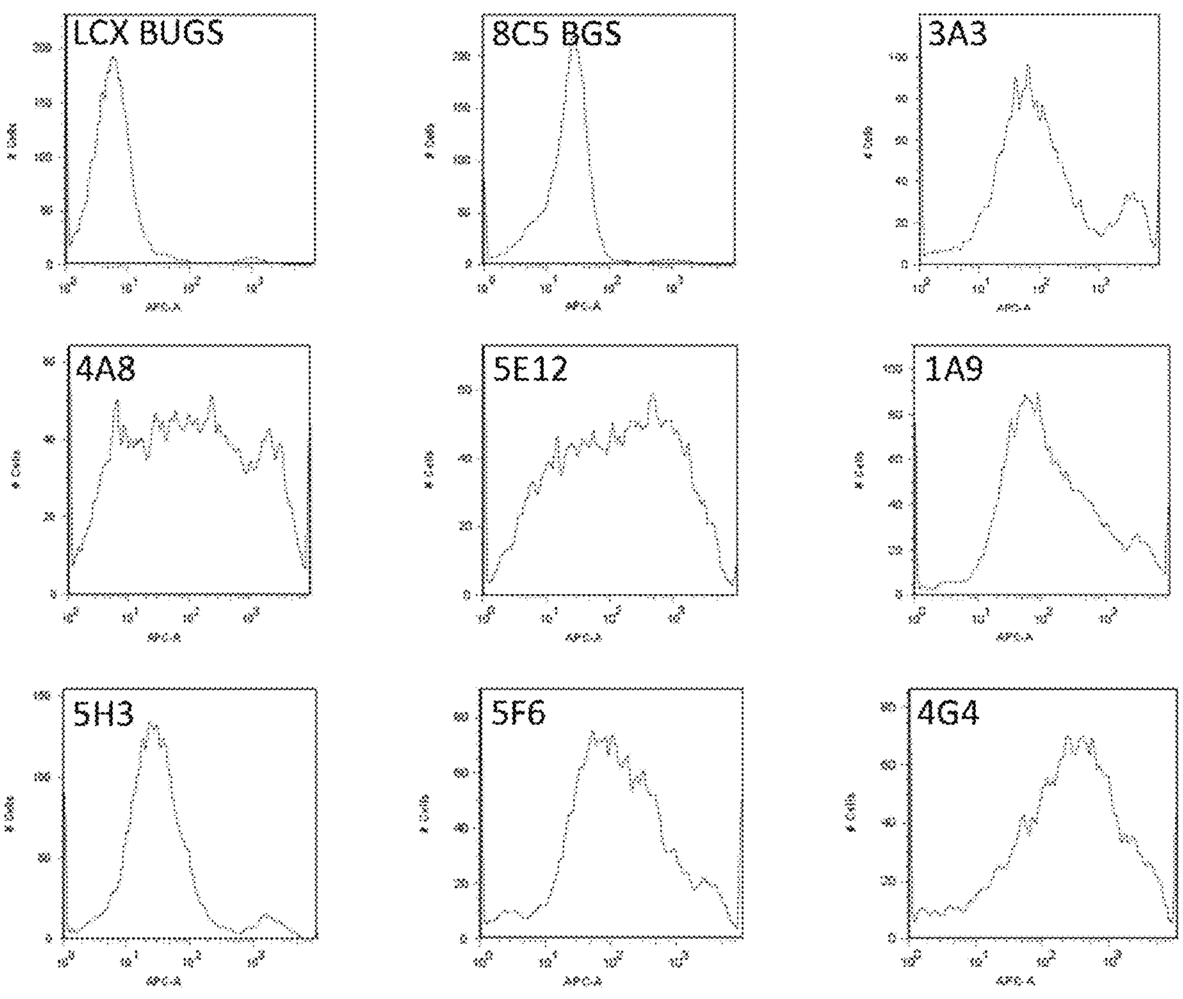
FIG. 25 illustrates 9 black and white flow cytometry histograms showing flow cytometry analysis of type III PV binding OCMS hybridoma secreting anti-PV IgG mAbs as described in Example 16.

We further analyzed these hybridomas to assess their level of PV binding by flow cytometry. FIG. 25 illustrates 9 black and white flow cytometry histograms showing flow cytometry analysis of type III PV binding OCMS hybridoma secreting anti-PV IgG mAbs. The hybridoma secreting human PV mAbs were analyzed by flow cytometry for binding to biotin-labeled type III PV. PV was detected using APC-labeled streptavidin. The majority of the cells in the PV hybridomas demonstrated some binding, compared to the negative control LCX BGS and 8C5 BGS cell lines.

Figure 26:
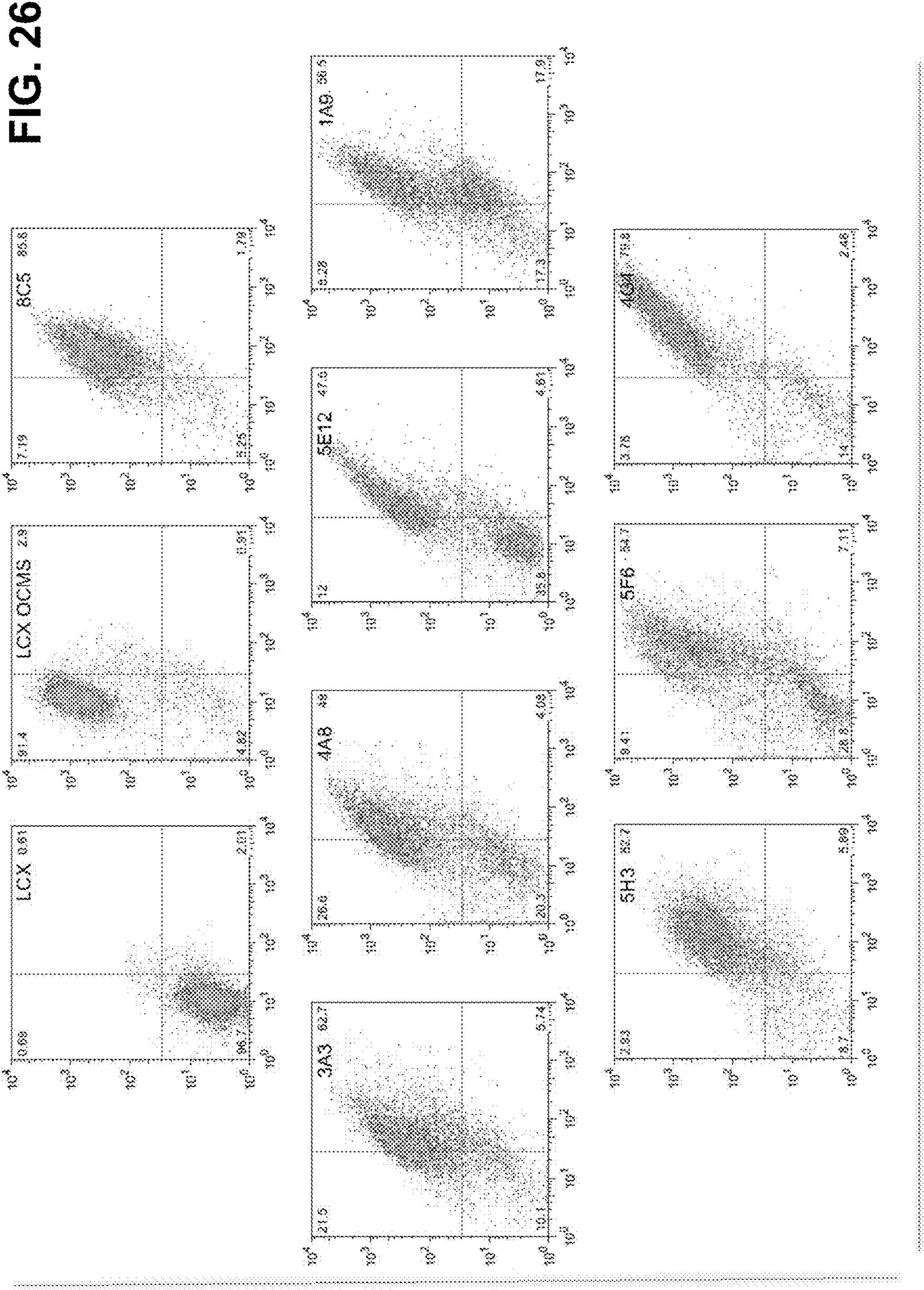
FIG. 26 shows flow cytometry graphs assessing tandem scFv and human IgG expression by hybridoma expressing anti-PV mAbs, as described in Example 16.

We next tested the hybridomas for the presence of a functional Anchor moiety, using RAH binding as a surrogate for the presence of the Anchor. Following overnight incubation of the cells with RAH, we used flow cytometry to assess human IgG and RAH binding simultaneously. FIG. 26 shows flow cytometry graphs assessing tandem scFv and human IgG expression by hybridoma expressing anti-PV mAbs. The hybridoma expressing anti PV-mAbs analyzed in FIG. 25 were assessed for binding of RAH (an indicator of functional expression of the tandem scFv fusion protein), and expression of human IgG. After incubation with RAH, cells were assessed for RAH binding using Allophycocyanin-conjugated AffiniPure F(ab')2 fragment Goat Anti Rabbit IgG (H+L) detection reagent and for human IgG binding using Biotinylated protein A and Alexa Flour 488-conjugated streptavidin reagent. The majority of the cells maintained expression of the Anchor following cell fusion, and were able to capture human IgG secreted by the cells. The percent double positive in each panel are: 3A3, 63%; 5E12, 48%; 1A9, 56%; 5H3, 82.7%; 5F6, 55%; 4G4, 80%. Note that during the cloning procedure, these cells had not been positively selected for human IgG or PV binding via the Anchor and RAH.

Thus, a cell line that expresses constitutively active IL-6 receptor gp130 ΔYY, the LCX cell line, in conjunction with the BGS Anchor protein, was created and demonstrated to be effective as a fusion partner with human B cells to create stable hybridomas secreting useful human monoclonal antibodies. In addition, even without positive selection for Anchor expression during the cloning and screening procedure, hybridomas derived from the LCX BGS fusion partner cell line maintained significant Anchor expression, making them suitable for analysis using OCMS methodologies.

Example 16: Universal Antiviral Mab Screening Method

As discussed above, the following provide examples of a universal antiviral mAb screening method. In the specific examples provided herein, two hybridomas are shown, 8C5, which secretes a human mAb specific for rabies glycoprotein GP), and 4G4, which secretes a human mAb that binds type 3 poliovirus (PV). The hybridomas were washed and incubated overnight in cell culture medium containing excess rabbit FAb fragment specific for human IgG (H+L) (Rockland, Cat No. 809-4102) and type 3 PV or rabies GP. They were washed with PBS+BSA and incubated for one hour with Alexa Fluor 488 conjugated F(ab)2 fragment of goat anti human IgG Fc specific (Jackson Immuno Research, Cat No 109-546-170) at 1:200 in PBS-BSA. One hour later, the cells were washed three times with PBS-BSA and fixed with 4% paraformaldehyde in PBS for 15 minutes at room temperature. After fixation, cells were washed once with PBS and once with $dH_2O$ and then the coverslips were mounted with ProLong® Gold Antifade reagent with DAPI (P36935, Thermo Fisher Scientific) and imaged with a C2+ Nikon confocal microscope with 63×/1.3 NA oil objective; images were analyzed with ImageJ software (https://imagej.nih.gov/ij/).

Figure 21A:
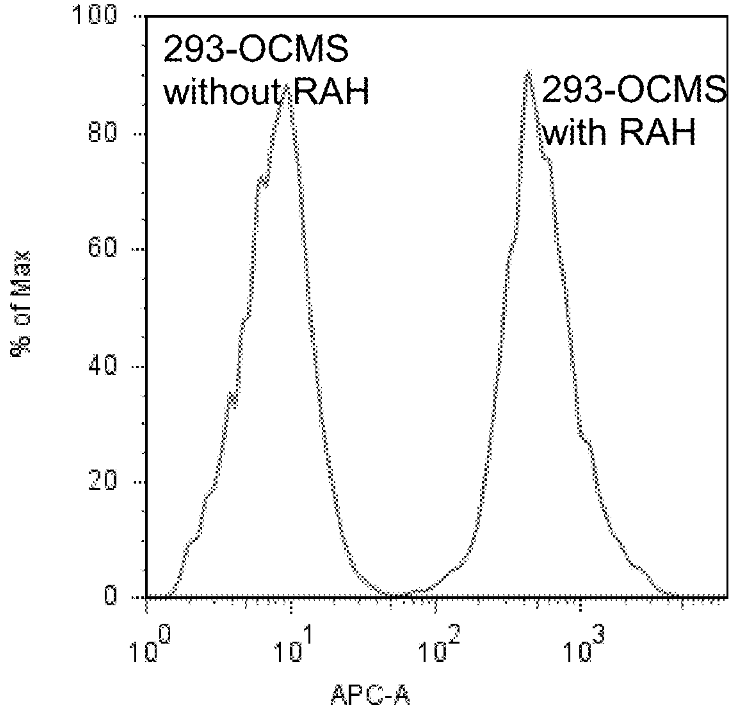
FIG. 21A provides a graph of flow cytometry showing that the binding of human Ig to the 293T OCMS cells depends on the presence of rabbit Igs specific for human Ig (RAH, Linker). The 293T OCMS cell line is a 293T cell line that expresses the BGS Anchor protein, in which OCMS is an acronym for On-Cell mAb Screening, and is also named 293T BGS. The 293T OCMS cells bind to human IgG only in the presence of RAH (Linker) and not when RAH is not present. The leftmost curve is 293T OCMS without rabbit anti-human antibody (RAH). The rightmost curve is 293T OCMS with RAH.
Figure 21B:
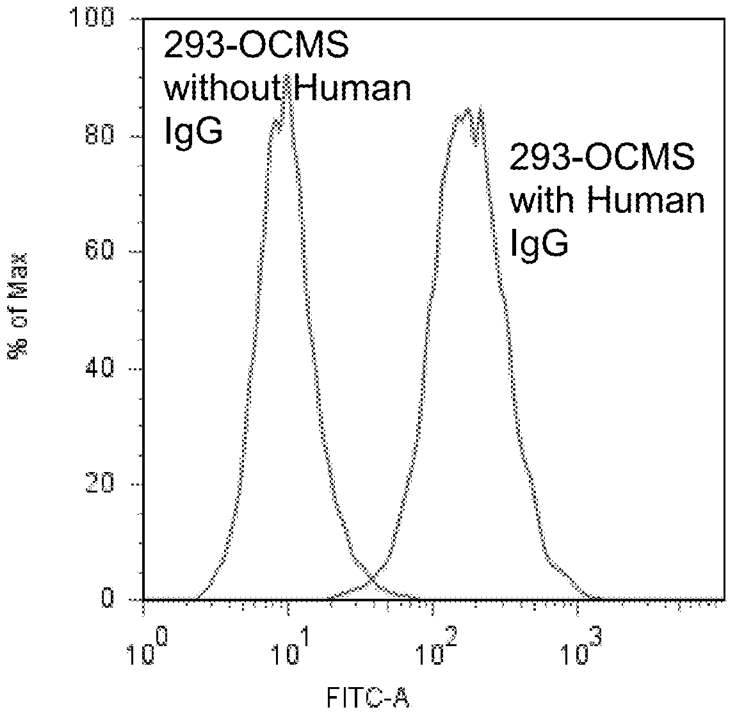
FIG. 21B provides a graph of flow cytometry showing that the 293T OCMS cells that are bound to rabbit Igs specific for human Ig (RAH, Linker) bind to polyclonal human IgG. The leftmost curve is 293-OCMS without human IgG. The rightmost curve is 293T OCMS with human IgG.
Figure 22A:
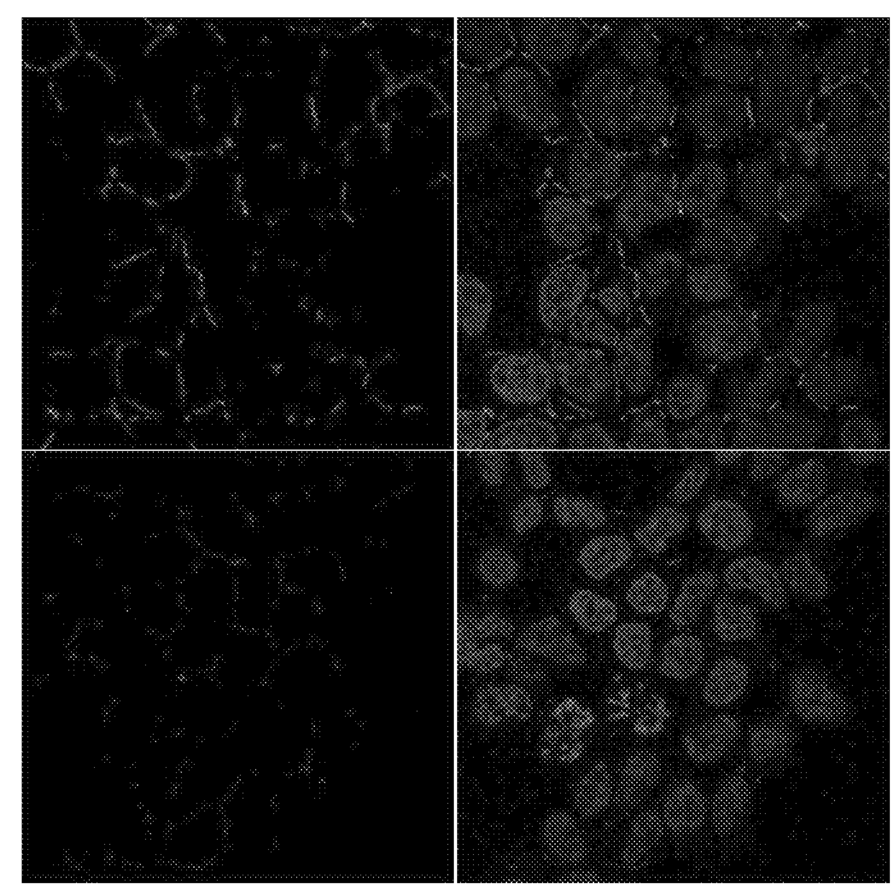
FIG. 22A shows four panels of 293T OCMS transient transfection of human IgG genes (anti-PV mAb A12), following culture in the presence of the RAH linker, and assessed for binding of human IgG. The top left panel shows 293T BGS transfected and labeled with Alexa Fluor IgG. The lower left panel shows 293T BGS untransfected and labeled with Alexa Fluor IgG. The top right panel shows 293T BGS transfected and merged with DAPI images. The lower left panel shows 293T BGS untransfected and merged with DAPI images.
Figure 22B:
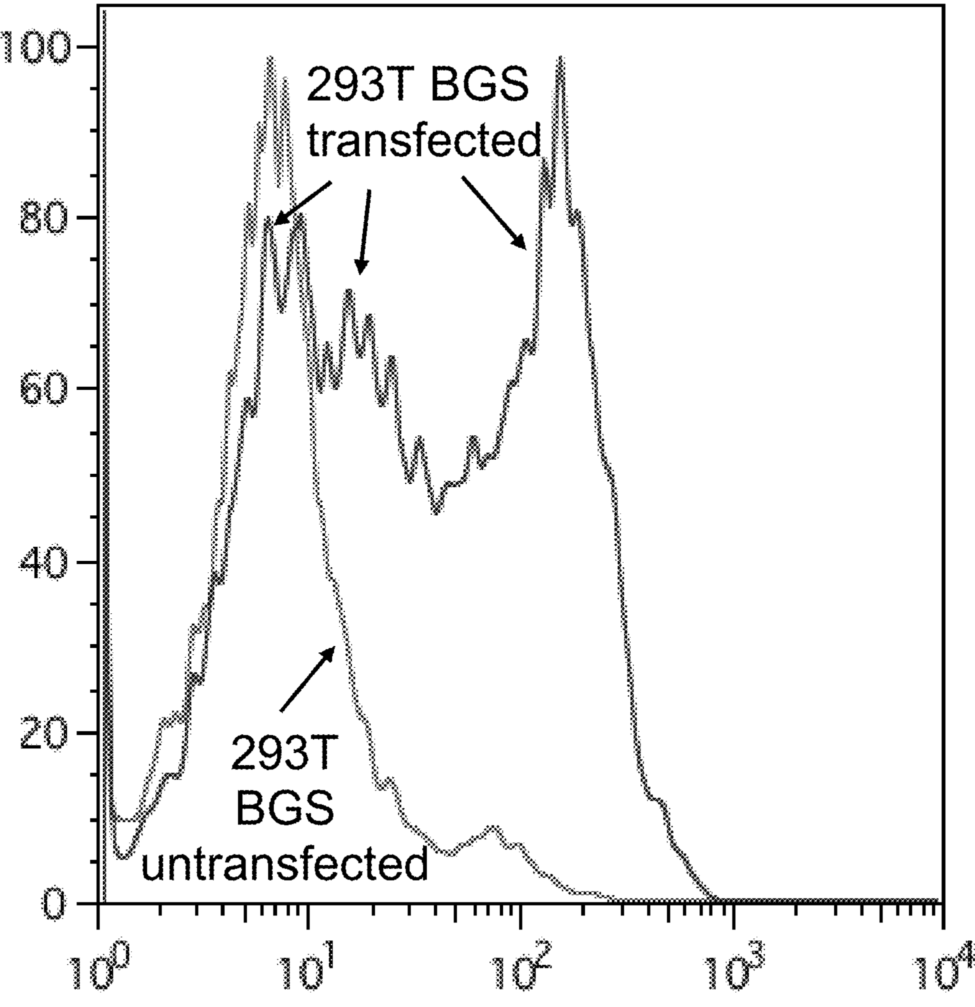
FIG. 22B shows a graph showing that transfected 293T BGS cells are successful in detecting PV. Briefly, the 293T BGS cells transfected or untransfected with human IgG gene expressing anti-PV mAb A12 were incubated with biotinylated PV type I. Such binding with PV type I was assessed and the result is plotted.

In FIG. 21, the green signal indicates human IgG attached to the hybridoma cells. For the 4G4 mAb, in the presence of PV type III, a tell-tale cap structure appears on the outer plasma membrane, which is the immune complex nucleated by the PV bound to the 4G4 IgG on the hybridoma surface. Because 4G4 does not bind the rabies GP, the IgGs on the hybridoma surface are homogeneously distributed in spots that encircle the cell nuclei. The converse situation is observed with the 8C5 hybridoma. In the presence of the GP, the cap structure is formed, a multivalent complex that includes the 8C5 IgG specific for the GP and the GP itself. No cap is seen in the 8C5 hybridoma exposed to PV.

A significant feature of this invention is that mAbs specific for both viruses were detected with a single set of reagents, neither antigen needed to be labeled or modified before use, and no additional virus-specific immune reagents were required. Thus, one embodiment of the present invention is a universal method to identify mAbs specific for viral antigens using a common set of detection reagents and protocols.

Poliovirus type 3 (PV3) specific OCMS hybridoma, 4G4-OCMS or anti-rabies glycoprotein OCMS hybridoma (8C5 OCMS) cells were plated at $5\times10^4$ cells/well on round Corning™ BioCoat™ 12 mm #1 German Glass Coverslips (Corning, Cat. 354087) in 24 well plates in 1% Advanced RPMI with 1 μg/ml Fab fragment of rabbit anti-human IgG (H+L) (Rockland, Cat 809-4102) and 10 μL of PV3 ($2\times10^3$ pfu/well) or 1 μg/ml of rabies glycoprotein (GP). The plate was incubated at 37° C. in a $CO_2$ incubator for overnight. The following day, the cells were washed thrice with PBS containing 1% BSA (PBS–BSA) added Alexa Fluor 488 conjugated F(ab)2 fragment of goat anti human IgG Fc specific (Jackson Immuno Research, Cat 109-546-170) at 1:200 in PBS–BSA and incubated for 1 hour at 37° C. in a $CO_2$ incubator. After 1 hour, cells were washed thrice with PBS–BSA and fixed with 4% paraformaldehyde in PBS for 15 minutes at room temperature. After fixation, cells were washed once with PBS and once with $dH_2O$ and then the coverslips were mounted with ProLong® Gold Antifade reagent with DAPI (P36935, Thermo Fisher Scientific) and imaged with a C2+ Nikon confocal microscope with 63×/1.3 NA oil objective; images were analyzed with ImageJ software (https://imagej.nih.gov/ij/).

Laser power and image capture times are set to give fluorescence counts between 300 and 3,000. We initially calculated local pixel intensity maxima, then drew four pixel circles around every intensity maximum. Spots were nominated as real on the basis of SpotToCell intensity (whole well calculation), its contrast (compared to adjacent pixels), and its distance from DAPI-stained pixels (nuclei). Data were confirmed by eye. For initial studies, 96-well plates were used, and the data collected are the number of positive signals in each well, compared to the number of DAPI-stained nuclei. The number of positive data points were compared for binding and non-binding hybridomas, and the significance was calculated using Student's t-test.

Other methodologies that can be used involves adapting the system using Fluorescence Resonance Energy Transfer (FRET) reagents[42], in which pairs of molecules need to be brought together to generate fluorescent light. FRET provides detailed information about whether two molecules are in proximity. In the event that non-specific viral binding to cells or mAbs occurs, which could increase the false positive rate, the culture medium can be adapted to reduce such background during the binding procedure, such as additional serum, purified albumins, or mild detergents.

Example 17: Methods for Testing Virus Micro-Neutralization on MAB-Secreting Hybridomas Therapeutic mAbs need to demonstrate viral neutralizing activity in vitro before they can be nominated for clinical development. The first such test is typically a microneutralization assay, in which cultured cell lines are infected with a virus, and the ability of a mAb to prevent a cytopathic effect is measured[20,43]. One of the advantages of the OCMS mAb cloning method is that it stably produces full-length IgGs that can be tested in micro-neutralization assays, without the need for recombinant mAb expression. An essential companion to a universal anti-viral mAb cloning assay is a panel of cell lines that can be used for testing viral neutralization. It would be advantageous if the OCMS hybridomas themselves were used to test viral neutralization.

To assess the anti-viral neutralizing activity of mAbs, their ability to protect the hybridomas that secrete them is assayed. First, we render the hybridomas susceptible to virus-induced killing. Then, mAb-secreting hybridomas are incubated with a dilution series of virus. Any living hybridomas are presumed to secrete neutralizing mAbs. This concept first arose in a study of Enterovirus 71 (a PV relative), which infects cells through a leukocyte marker, PSGL-1, which is also expressed by our hybridomas. We found that EV71 kills OCMS hybridomas over a three day incubation period, whereas PV does not. In a 24 hour experiment, comparing cytotoxicity of EV71 to PV on the LCX OCMS cell line, we detected cell death with the Fixable Viability dye eFluor 780 (eBioscience). 25% of the EV71 treated cells were killed, compared to 6% and 4% of the mock-treated and PV-exposed cells, respectively.

We introduce the PV receptor (CD155) into hybridomas that express human anti-PV mAbs, and test whether cell viability correlates with mAb neutralizing titers. We will optimize this method for detection using the Operetta High-Content Imaging System.

Example 18: Procedures to Detect Viral Cytopathic Effects

The ability of a virus to infect a cell results from multiple factors, especially the presence of a receptor for the virus on the cell surface and the cytokine responses of the infected cell[44]. The susceptibility of the LCX OCMS cell line to EV71-induced killing suggests that they would also be killed, if they expressed the human PV receptor (hPVR, CD155)[45]. We express CD155 in LCX OCMS cells using retroviral gene transduction, isolating a panel of 6 cell clones that span 2 logs of CD155 expression. We test these for PV infection using the Operetta assay described above, identifying the optimal levels of CD155 expression and PV dose (50% Tissue Culture Infective Doses, TCID50). We then test a panel of human PV mAbs with known neutralization capacity (9H2, 8H4, 7E2, and a control mAb, 6A)[22,20,46], in a dilution series from 1 mg/ml stocks as described previously, calculating the neutralization titer using the Karber formula[46,47].

We then introduce CD155 expression, at its optimal level, into the 9H2, 8H4, 7E2, and 6A hybridomas. CD155-expressing cells plated in 96-well plates are assessed for cytopathogenicity in the presence of a dilution series of virus, calculating the TCID50 for each cell line[46,47]. The TCID50 values correlate with mAb neutralization titers obtained using the traditional microneutralization test. TCID50 values are also measured for the hybridomas under different protocols, to compare (a) freshly-washed hybridomas vs. hybridomas incubated overnight (low vs. high initial mAb concentrations) and (b) hybridomas plated at low vs. high density.

Examples 17-18 illustrate whether the efficiency of the OCMS hybridoma can be maximized by using mAb-expressing hybridomas themselves for viral neutralization testing. If the hybridomas are not infected lethally by PV, despite the expression of the hPVR, we perform the same experiments with EV71 infection of the cells. The analysis of the cell killing is done with the Operetta system (PerkinElmer) or by microscopic examination.

Example 19: The OCMS Platform is Adapted to Genetically Optimize Mab Structure and Function The human mAbs identified herein are likely to be excellent candidate anti-viral therapeutics. Nonetheless, it may be important to modify human mAb to improve mAb stability, expression levels, binding kinetics, or binding specificity. Using the high-throughput screening capabilities of the OCMS platform, we perform Directed Evolution of the cloned mAbs, i.e. mutagenesis followed by selection of improved mAb variants.

Natural mechanisms of antibody diversification through somatic hypermutation can be induced in any cell through expression of the DNA-modifying protein, Activation-Induced Cytidine Deaminase (AID)[39]. We establish a system for improving the capabilities of the human mAbs referenced herein. In mAb-expressing hybridomas, we express AID as a fusion protein that can be activated by tamoxifen exposure. We then activate AID expression and analyze the binding activities of the mutated mAbs that result. We use cross-reactive mAb binding to poliovirus strains as our experimental model. In this Directed Evolution experiment, we treat the hybridoma cell populations, then mix the cell populations with labeled PV virions, and analyze them using flow cytometry to identify clones that have improved PV binding capabilities. Mutated clones are analyzed by Ig gene sequencing.

(a) A retroviral gene construct that expresses an AID-estrogen receptor fusion protein (AID-ER), which can activate antibody gene mutation in the presence of tamoxifen.

We synthesize a cDNA that expresses a published AID-ER fusion protein, which is capable of inducing somatic hypermutation in Ig genes upon tamoxifen treatment, based on the work of Doi et al.[48]. The construct contains a GFP cassette, and is introduced into fibroblast cells using the vector pBabe Puro (Addgene plasmid #1764)[22]. We determine the localization of the AID-ER fusion protein in the fibroblast cells using immunofluorescence staining with antibodies to the ER domain. We confirm that the protein is primarily located in the cytoplasm in the untreated state, and determine the optimal concentration and time course to induce movement of the protein into the nucleus.

(b) The AID-ER moves from the cytoplasm to the nucleus upon tamoxifen treatment.

We express the AID-ER gene in hybridomas expressing anti-viral mAbs and establish the kinetics of gene mutation during tamoxifen treatment. To test the activity of AID-ER in hybridoma cells expressing human mAbs, we use lentiviral gene transduction to introduce the AID-ER gene into the following hybridoma cell lines, which all make human mAbs specific for Sabin PV strains. We selected hybridomas that express IgG mAbs with distinctive binding activities that can be readily assessed for mutation-induced changes. 2H5 has low affinity binding and neutralizing activity against Sabin types 1 and 2[20]. 9H2, binds a linear epitope common to Sabin types 1, 2, and 3, but with somewhat less binding to Sabin 3[46]. 7E5 and 8H4, both bind Sabin type 1 and 2 only, and are of interest because they are highly similar, differing in only 3 AAs in their antigen binding domains. Notably, they bind the same epitope on Sabin type 1 PV, but different epitopes on Sabin type 2[46]. We use the puromycin-selectable transfer vector, pCDH-EF1-FHC (Addgene #64874)[49] to generate populations of cells, and then isolate individual clones for evaluation of AID-ER expression by immunofluorescence and Western blotting.

The hybridomas are treated with Tamoxifen at different doses and schedules and examine the population for PV binding activity using flow cytometry and purified, AlexaFluor labeled Sabin 1, 2 and 3 virions. Models for this type of experiment are shown in Bowers et al.[38]. We first test high-binding hybridomas for generation of subclones that have lost PV binding activity, measuring the number of non-binding clones arising per unit time (e.g. hours, days, cell divisions). We then perform deep sequencing of the Ig genes in those populations to calculate the rate of synonymous and non-synonymous mutations over time, and will use this rate as a baseline for future studies.

We perform a series of gain of function experiments (Directed Evolution) to model real-world drug discovery efforts and establish the mutation treatments/rates required for mAb improvement. For example, we attempt to increase the binding affinity of 2H5 for PV types 1 and 2, and of 9H2 for PV type 3. We perform similar experiments on the 7E5 and 8H4 mAbs, to identify subclones with improved type 1 and type 2 binding activities. For all of these experiments, we deep sequence the populations to determine whether the baseline mutation rate varies from the expected, and we isolate and sequence improved mAb clones. Data are analyzed using the reference Ig sequences in the IGMT database and additional with the Rep-seq (Ig sequence analysis) software suite[50].

These experiments will establish the basic parameters for Directed Evolution of human antibodies using natural somatic hypermutation processes and isolating rare, improved outliers using the OCMS mAb cloning platform. In another embodiment, we test a full-length AID. Outlier subclones are immediately subjected to Ig gene sequencing and recombinant expression. If the AID-ER is leaky, causing mutations when they are not desired, we introduce the gene in a construct under control of a doxycycline inducible promoter, giving two levels of control of AID activity.

Each and every patent, patent application, and specifications including U.S. Provisional Patent Application Nos. 62/476,599 and 62/526,608, and publications, including websites cited throughout the specification, and sequences identified in the specification and Sequence Listing, is incorporated herein by reference. While the invention has been described with reference to particular embodiments, it will be appreciated that modifications can be made without departing from the spirit of the invention. Such modifications are intended to fall within the scope of the appended claims.

REFERENCES

1. Zhou C, et al. "Development of a novel mammalian cell surface antibody display platform", *mAbs* (2010), 2:5, 508-518, DOI: 10.4161/mabs.2.5.12970.
2. Mckinney, K L et al., "Manipulation of Heterogeneous Hybridoma Cultures for Overproduction of Monoclonal Antibodies", *Biotechnol Prog.* (1991 September-October), 7(5):445-54.
3. Price, P W et al. "Engineered cell surface expression of membrane immunoglobulin as a means to identify monoclonal antibody-secreting hybridomas." *J Immunol Methods.* (2009 Mar. 31); 343(1):28-41
4. Kumar N, Borth N, "Flow-cytometry and cell sorting: an efficient approach to investigate productivity and cell physiology in mammalian cell factories", *Methods* (2012 March); 56(3):366-74. doi: 10.1016/j.ymeth.2012.03.004.

5. Dobson, L et al., "The human transmembrane proteome", *Biol Direct.* 2015 May 28; 10:31. doi: 10.1186/s13062-015-0061-x.PMID: 26018427.
6. The website for the Human Transmembrane Proteome database, database version: d. 1.4, dated Jun. 24, 2016 at address http://htp.enzim.hu.
7. U.S. Pat. No. 7,906,111
8. Khan, K H, "Gene Expression in Mammalian Cells and its Applications", Adv. Pharm Bull, (2013 December) 392): 257-263;
9. Green MR and Sambrook J, "Molecular Cloning, A Laboratory Manual", 2012 Cold Spring Harbor Laboratory Press
10. Manjunath N et al, *Adv. Drug Deliv. Rev.*, (2009) 61(9): 732-745
11. Sambrook et al, Molecular Cloning: A Laboratory Manual, Cold Spring Harbor Press, Cold Spring Harbor, NY
12. Tiscornia G et al, "Production and purification of lentiviral vectors." *Nature protocols* (2006) 1: 241-245;
13. Dessain S K et al., "High efficiency creation of human monoclonal antibody-producing hybridomas.", *J Immunol Methods* (2004) 291:109-122;
14. Garry Nolan, https://www.addgene.org/1730/.
15. Vitale L A et al., "Development of a human monoclonal antibody for potential therapy of CD27-expressing lymphoma and leukemia." *Clin Cancer Res* (2012), 18: 3812-3821 (2012)
16. Walker C et al, "T cell activation by cross-linking anti-CD3 antibodies with second anti-T cell antibodies: dual antibody cross-linking mimics physical monocyte interaction." *Eur J Immunol* (1987), 17: 1611-1618
17. Merle, N S et al. "Complement System Part I—Molecular Mechanisms of Activation and Regulation." *Frontiers in Immunology* (2015), 6: 262
18. Taylor, R P et al, "The role of complement in mAb-based therapies of cancer." *Methods* (2014) 65: 18-27
19. Sommer J et al., "Constitutively active mutant gp130 receptor protein from inflammatory hepatocellular adenoma is inhibited by an anti-gp130 antibody that specifically neutralizes interleukin 11 signaling." *J Biol Chem* (2012) 287: 13743-13751.
20. Puligedda R D et al., "Human monoclonal antibodies that neutralize vaccine and wild-type poliovirus strains." *Antiviral Res* (2014), 108: 36-43, Epub 2014 May 16.
21. U.S. Pat. No. 8,557,575
22. Adekar S P et al., "Hybridoma populations enriched for affinity-matured human IgGs yield high-affinity antibodies specific for botulinum neurotoxins." *J Immunol Methods* (2008), 333: 156-166. Epub 2008/03/04.
23. Yu X et al, "An optimized electrofusion-based protocol for generating virus-specific human monoclonal antibodies." *J Immunol Methods* (2008 Jul. 31) 336(2):142-51
24. Greenfield E A, "Antibodies: A Laboratory Manual." Cold Spring Harbor Laboratory Press, Cold Spring Harbor, NY, ed. 2nd (2014)
25. Mompo S M, A. Gonzalez-Fernandez, "Antigen-specific human monoclonal antibodies from transgenic mice." *Methods Mol Biol* (2014) 1060: 245-276
26. Spieker-Polet H et al, "Rabbit monoclonal antibodies: generating a fusion partner to produce rabbit-rabbit hybridomas." *Proc Natl Acad Sci USA* (1995) 92: 9348-9352
27. Hoehn K B et al, "The Diversity and Molecular Evolution of B-Cell Receptors during Infection." *Mol Biol Evol* (2016) 33: 1147-1157
28. Ravetch J V, Bolland S, "IgG Fc receptors." *Annu Rev Immunol* (2001) 19:275-290.
29. Chattopadhyay P K, et al, "Live-cell assay to detect antigen-specific CD4+ T-cell responses by CD154 expression." *Nature protocols* (2006) 1:1-6.
30. Kohler G, Milstein C, "Continuous cultures of fused cells secreting antibody of predefined specificity." *Nature* (1975) 256: 495-497.
31. Zhu Y, et al., "Improved fusion partners transfected with DNA fragment encoding IL-11 on generation of human B lymphocyte hybridomas." *Hum Antibodies* (1999), 9: 1-7.
32. Harris J F, et al, "Increased frequency of both total and specific monoclonal antibody producing hybridomas using a fusion partner that constitutively expresses recombinant IL-6." *J Immunol Methods* (1992), 148: 199-207.
33. Flyak A I, et al., Mechanism of human antibody-mediated neutralization of Marburg virus. Cell. 2015; 160(5):893-903. Epub 2015/02/28.
34. Jin Y, et al. Human monoclonal antibodies as candidate therapeutics against emerging viruses. Front Med. 2017; 11(4):462-70
35. Dessain S K, et al. Exploring the native human antibody repertoire to create antiviral therapeutics. Curr Top Microbiol Immunol. 2008; 317:155-83.
36. Tiller T, et al. Efficient generation of monoclonal antibodies from single human B cells by single cell RT-PCR and expression vector cloning. J Immunol Methods. 2008; 329(1-2):112-24. Epub 2007/11/13.
37. Smith S A, Crowe J E, Jr. Use of Human Hybridoma Technology To Isolate Human Monoclonal Antibodies. Microbiology spectrum. 2015; 3(1). Epub 2015/06/25. PubMed PMID: 26104564.
38. Bowers P M, et al. Mammalian cell display for the discovery and optimization of antibody therapeutics. Methods. 2014; 65(1):44-56. Epub 2013/06/25.
39. Pavri R, Nussenzweig M C. AID targeting in antibody diversity. Adv Immunol. 2011; 110:1-26.
40. Romani B, et al. Antibody production by in vivo RNA transfection. Scientific reports. 2017; 7(1):10863.
41. Lorenz C M, et al. The effect of low intensity ultraviolet-C light on monoclonal antibodies. Biotechnol Prog. 2009; 25(2):476-82.
42. Gaborit N, et al. Time-resolved fluorescence resonance energy transfer (TR-FRET) to analyze the disruption of EGFR/HER2 dimers: a new method to evaluate the efficiency of targeted therapy using monoclonal antibodies. J Biol Chem. 2011; 286(13):11337-45. Epub 2011/02/02.
43. Lee S S, et al. Development of a micro-neutralization assay for ebolaviruses using a replication-competent vesicular stomatitis hybrid virus and a quantitative PCR readout. Vaccine. 2017; 35(41):5481-6.
44. McFadden G, et al. Cytokine determinants of viral tropism. Nat Rev Immunol. 2009; 9(9):645-55.
45. Mendelsohn C L, et al. Cellular receptor for poliovirus: molecular cloning, nucleotide sequence, and expression of a new member of the immunoglobulin superfamily. Cell. 1989; 56(5):855-65.
46. Puligedda R D, et al. Characterization of human monoclonal antibodies that neutralize multiple poliovirus serotypes. Vaccine. 2017. doi: 10.1016/j.vaccine.2017.03.038. PubMed PMID: 28343771.
47. Organization W H. Manual for the virological investigation of polio. Geneva, Switzerland 1997.
48. Doi T, et al. The C-terminal region of activation-induced cytidine deaminase is responsible for a recombination function other than DNA cleavage in class switch recombination. Proc Natl Acad Sci USA. 2009; 106(8):2758-63.

49. Yousefzadeh M J, et al. Mechanism of suppression of chromosomal instability by DNA polymerase POLQ. PLOS genetics. 2014; 10(10):e1004654.

50. Lefranc MP. IMGT, the International ImMunoGeneTics Information System. Cold Spring Harb Protoc. 2011; 2011(6):595-603.

The invention claimed is:

1. A method of identifying an immortalized cell that secretes an antibody or fragment thereof among a heterogeneous population of immortalized cells, the method comprising:

(a) providing the population of immortalized cells having expressed on their outer plasma membrane surfaces an Anchor, wherein the Anchor comprises i) an extracellular region comprising an antibody or fragment thereof capable of binding a selected Linker to form a first complex, and ii) a transmembrane amino acid sequence that immobilizes the Anchor on the outer plasma membrane surfaces, wherein said Anchor cannot bind the antibody or fragment thereof; with (b) contacting the immortalized cells of (a) with an effective amount of the Linker, wherein the Linker is a soluble antibody or antibody fragment comprising a variable domain that binds and forms a second complex with a conserved domain of the antibody or fragment thereof, wherein the contacting permits the antibody or fragment thereof to be linked to the surface of the immortalized cell that secretes it upon formation of the first and second complexes; and (c) identifying the existence, antigen specificity, antigen binding affinity, titer, amount, or biological activity of the antibody or fragment thereof secreted by the immortalized cells and bound thereto by the cell-bound multiple immune complexes formed by Anchor-Linker-antibody or fragment thereof.

2. The method according to claim 1, further comprising isolating the immortalized cells at any time after step (a).

3. The method according to claim 1, wherein (a) further comprises contacting the immortalized cells with an excess concentration of the Linker, wherein the excess increases the specificity of the binding between the first complex on the cell surface of an immortalized cell and the antibody or fragment thereof secreted by that immortalized cell, relative to the binding of the antibody or fragment thereof to other immortalized cells that do not secrete it.

4. The method according to claim 1, wherein (a) further comprises contacting the cells with a competitor antibody of the same species or type as the secreted antibody or fragment thereof, the competitor antibody having a different or non-specific antigen binding specificity, wherein the presence of the competitor antibody increases the specificity of the binding between the first complex on the cell surface and the antibody or fragment thereof secreted by the cell, relative to the binding of that antibody or fragment thereof to a cell that does not secrete it, by binding excess unbound Linker.

5. The method according to claim 1, wherein step (a) further comprises contacting the immortalized cells with a detectably labelled antigen to which the antibody or fragment thereof specifically binds in a third complex; and forming cells to which are bound a multi-complex formed by the first complex Anchor-Linker, the Linker also bound to the secreted antibody or fragment thereof, which is bound to the antigen; wherein step (c) comprises identifying immortalized cells that secrete the antibody or fragment thereof specific for a selected antigen by identifying or quantifying the detectable label associated with the cell-bound multi-part complex.

6. The method according to claim 1, wherein the antibody or fragment thereof is a human antibody or fragment thereof, the Anchor molecule comprises an scFv specific for a selected non-human-originated Linker; and the Linker is an anti-human-Ig antibody or an anti-human-Ig antibody fragment thereof.

7. The method according to claim 1, wherein the Linker specifically binds an Fc portion of the target antibody or fragment thereof; and wherein step (b) further comprises contacting the immortalized cells with (i) an antibody Fc domain competitor of the same species as that of the antibody or fragment thereof, and (ii) a detectably labeled antibody specific for an FAb domain of the same mammalian species as that of the target antibody or fragment thereof, wherein target antibody or fragment thereof secreted by the immortalized cell is bound to the cell in a complex with the Anchor-Linker and is bound in the medium by excess Linker;

wherein the Fc domains compete to reduce binding of intact target antibody or fragment thereof to immortalized cells that do not secrete the target antibody or fragment thereof; and wherein the antibody specific for an FAb antibody binds to the secreted target antibody or fragment thereof bound to the cell surface.

8. The method according to claim 1, wherein the antibody or fragment thereof is a human antibody; the Anchor molecule comprises an scFv specific for a selected non-human-originated Linker; and the Linker is an anti-human-Ig antibody or an antibody binding fragment of an anti-human-Ig antibody.

9. The method according to claim 1, wherein the population of immortalized cells is a population of recombinant mammalian cells.

10. The method according to claim 9, wherein the recombinant mammalian cells are 293T cells or CHO cells.

11. The method according to claim 1, wherein the population of immortalized cells is a population of hybridoma cells.

12. A method of detecting or measuring a characteristic of a target protein secreted by an immortalized cell comprising:

(a) contacting i. a population of immortalized cells, wherein each cell of the population has expressed on its outer plasma membrane surface an Anchor, wherein the Anchor comprises i) an extracellular region comprising an antibody or fragment thereof capable of binding a selected Linker to form a first complex, and ii) a transmembrane amino acid sequence that immobilizes the Anchor on the outer plasma membrane surfaces, wherein said Anchor cannot bind the target protein; with ii. the Linker designed to form the first complex and to form a second complex with the target protein that is not recognized by the Anchor, iii. the contacting permitting the Linker to adhere to the outer plasma membrane of the cells by binding in the first complex with the Anchor;

(b) maintaining the cells of (a) in the presence of the Linker under conditions in which the cells secrete the target protein and the target protein binds to the cell-adhered first complex via formation of the second complex; and (c) identifying the existence, antigen specificity, antigen binding affinity, titer, amount, or biological activity of the target protein bound onto the cell by the first and second complexes.

13. The method according to claim 12, wherein (a) further comprises contacting the cells with an excess concentration of the Linker, wherein the excess increases the specificity of the binding between the first complex on the cell surface and the target protein secreted by the cell, relative to the binding of the target protein to other cells in the population that do not secrete it.

14. The method according to claim 12, wherein (a) further comprises contacting the cells with a competitor protein of the same species or type as the secreted target protein, the competitor protein having a different or non-specific antigen binding specificity, wherein the presence of the competitor protein increases the specificity of the binding between the first complex on the cell surface and the target protein secreted by the cell, relative to the binding of the target protein to a cell that does not secrete it, by binding excess unbound Linker.

15. The method according to claim 12, wherein step (a) further comprises contacting the cells with a detectably labelled antigen to which the target protein specifically binds in a third complex; and forming cells to which are bound a multi-part complex formed by Anchor-Linker of the first complex, wherein the Linker is also bound to the target protein, and wherein the target protein further binds the antigen; wherein step (c) comprises identifying cells that secrete target protein that specifically binds the labelled antigen by identifying or quantifying the detectable label associated with the cell-bound multi-part complex.

16. The method according to claim 12, wherein the population of immortalized cells is a population of recombinant mammalian cells.

17. The method according to claim 16, wherein the recombinant mammalian cells are 293T cells or CHO cells.

18. The method according to claim 12, wherein the population of immortalized cells is a population of hybridoma cells.

* * * * *